(12) United States Patent
Xu et al.

(10) Patent No.: US 6,887,660 B2
(45) Date of Patent: *May 3, 2005

(54) COMPOUNDS FOR IMMUNODIAGNOSIS OF PROSTATE CANCER AND METHODS FOR THEIR USE

(75) Inventors: Jiangchun Xu, Bellevue, WA (US); Davin C. Dillon, Redmond, WA (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/030,606

(22) Filed: Feb. 25, 1998

(65) Prior Publication Data

US 2002/0081580 A1 Jun. 27, 2002

Related U.S. Application Data

(63) Continuation-in-part of application No. 09/020,747, filed on Feb. 9, 1998, now abandoned, which is a continuation-in-part of application No. 08/904,809, filed on Aug. 1, 1997, now abandoned, which is a continuation-in-part of application No. 08/806,596, filed on Feb. 25, 1997, now abandoned.

(51) Int. Cl.$^7$ ................................................ C12Q 1/68
(52) U.S. Cl. ........................... 435/6; 435/91.1; 435/94; 536/23.1; 536/24.3; 536/24.31
(58) Field of Search ........................... 435/6, 91.1, 94; 436/64; 536/23.5, 24.3, 24.31, 24.33, 23.1

(56) References Cited

U.S. PATENT DOCUMENTS

| | | | |
|---|---|---|---|
| 5,786,148 A | | 7/1998 | Bandman et al. ............. 435/6 |
| 6,130,043 A | * | 10/2000 | Billing-Medel et al. ........ 435/6 |
| 6,252,047 B1 | | 6/2001 | Billing-Medel et al. .... 530/350 |
| 2002/0086301 A1 | | 7/2002 | Billing-Medel et al. ........ 435/6 |

FOREIGN PATENT DOCUMENTS

| | | |
|---|---|---|
| EP | 652 014 A1 | 5/1995 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/30758 | 11/1995 |
| WO | WO 96/21671 | 7/1996 |

OTHER PUBLICATIONS

Harris et al. J. of The Am Society of Nephrology 6:1125–33, 1995.*
Ahn et al. Nature Genetics 3(4):283–91, 1993.*
Cawthon et al. Genomics 9(3)446–60, 1991.*
MPSRCH search report, 2003, us–09–030–606–110.res, pp. 5–6, 9–10.*
Sambrook et al, eds, 1989, Molecular cloning, a Laboratory manual, 2nd ed, Cold Spring Harbor Laboratoy Press, Cold Spring Harbor, p. 11.8.*
Gelmini, S et al, 2001, Clin Chem Lab Med, 39(5): 385–391.*
Kibel, AS et al, 2000, J urol, 164(1): 192–6.*
Ren, C et al, 1998, Cancer Res, 58(6): 1285–90.*
Gingrich, JR et al, 1996, Cancer res, 56(18): 4096–4102.*
Corey E et al. Clinical Chemistry 43(3): 443–452, 1997.*
Schmidt, S., J. Comparative Neurology, 430(2): 160–171, 2001.*
Alexeyev et al., "Improved antibiotic–resistance gene cassettes and omega elements for *Escherichia coli* vector construction and in vitro deletion/insertion mutagenesis," *Gene 160*:63–67, 1995.
Blok et al., "Isolation of cDNAs That Are Differentially Expressed Between Androgen–Dependent and Androgen–Independent Prostate Carcinoma Cells Using Differential Display PCR," *The Prostate 26*: 213–224, 1995.
Database EMBL Accession No. AA453562, Jun. 11, 1997, Hillier et al., "Homo Sapiens cDNA Clone 788180."
El–Shirbiny, Prostatic Specific Antigen, *Advances In Clinical Chemistry 31*: 99–133, 1994.
Robson et al., "Identification of prostatic androgen regulated genes using the differential display technique," *Proceedings Of The American Association For Cancer Research Meeting 86, 36*: p. 266, Abstract No. 1589, 1995.
Short et al., "λZAP: a bacteriophage λ expression vector with in vivo excision properties," *Nucleic Acids Research 16*(15): 7583–7600, 1988.

* cited by examiner

*Primary Examiner*—Susan Ungar
*Assistant Examiner*—Minh-Tam Davis
(74) *Attorney, Agent, or Firm*—Seed IP Law Group PLLC

(57) ABSTRACT

Compounds and methods for diagnosing prostate cancer are provided. The inventive compounds include polypeptides containing at least a portion of a prostate tumor protein. The inventive polypeptides may be used to generate antibodies useful for the diagnosis and monitoring of prostate cancer. Nucleic acid sequences for preparing probes, primers, and polypeptides are also provided.

2 Claims, No Drawings

COMPOUNDS FOR IMMUNODIAGNOSIS OF PROSTATE CANCER AND METHODS FOR THEIR USE

REFERENCE TO RELATED APPLICATIONS

This application is a continuation-in-part of U.S. patent application Ser. No. 09/020,747, filed Feb. 9, 1998, now abandoned, which is a continuation-in-part of U.S. patent application Ser. No. 08/904,809, filed Aug. 1, 1997, now abandoned, which is a continuation-in-part of U.S. patent application Ser. No. 08/806,596, filed Feb. 25, 1997, now abandoned.

TECHNICAL FIELD

The present invention relates generally to the treatment and monitoring of prostate cancer. The invention is more particularly related to polypeptides comprising at least a portion of a prostate protein. Such polypeptides may be used for the production of compounds, such as antibodies, useful for diagnosing and monitoring the progression of prostate cancer, and possibly other tumor types, in a patient.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into diagnosis and therapy of the disease, prostate cancer remains difficult to detect and to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited diagnostic and therapeutic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved and diagnostic methods for prostate cancer.

SUMMARY OF THE INVENTION

The present invention provides methods for immunodiagnosis of prostate cancer, together with kits for use in such methods. Polypeptides are disclosed which comprise at least an immunogenic portion of a prostate tumor protein or a variant of said protein that differs only in conservative substitutions and/or modifications, wherein the prostate tumor protein comprises an amino acid sequence encoded by a DNA molecule having a sequence selected from the group consisting of nucleotide sequences recited in SEQ ID Nos: 2–3, 5–107, 109–11, 115–171, 173–175, 177, 179–224 and variants thereof. Such polypeptides may be usefully employed in the diagnosis and monitoring of prostate cancer.

In one specific aspect of the present invention, methods are provided for detecting prostate cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of prostate cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of prostate cancer.

The present invention further provides methods for detecting prostate cancer comprising: (a) obtaining a biological sample from a patient; (b) contacting the sample with a first and a second oligonucleotide primer in a polymerase chain reaction, at least one of the oligonucleotide primers being specific for a DNA molecule that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a DNA molecule having a partial sequence selected from the group consisting of SEQ ID Nos: 2–3, 5–107, 109–11, 115–171, 173–175, 177 and 179–224.

In a further aspect, the present invention provides a method for detecting prostate cancer in a patient comprising: (a) obtaining a biological sample from the patient; (b) contacting the sample with an oligonucleotide probe specific for a DNA molecule that encodes one of the above polypeptides; and (c) detecting in the sample a DNA sequence that hybridizes to the oligonucleotide probe. Preferably, the oligonucleotide probe comprises at least about 15 contiguous nucleotides of a DNA molecule having a partial sequence selected from the group consisting of SEQ ID Nos: 2–3, 5–107, 109–11, 115–171, 173–175, 177 and 179–224.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the immunodiagnosis and monitoring of prostate cancer. The inventive compositions are generally polypeptides that comprise at least a portion of a prostate tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human prostate tumor protein, or a variant thereof such a protein, wherein the prostate tumor protein includes an amino acid sequence encoded by a DNA molecule having a sequence selected from the group consisting of nucleotide sequences recited in SEQ ID Nos: 2–3, 5–107, 109–11, 115–171, 173–175, 177, 179–224, the complements of said nucleotide sequences and variants thereof. As used herein, the term "polypeptide" encompasses amino acid chains of any length, including full length proteins, wherein the amino acid residues are linked by covalent peptide bonds. Thus, a polypeptide comprising a portion of one of the above prostate proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human prostate tumor protein is a portion that is capable of eliciting an immune response in a patient inflicted with prostate cancer and as such binds to antibodies present within sera from a prostate cancer patient. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of prostate cancer patients.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For prostate tumor polypeptides with immunoreactive properties, variants may, alternatively, be identified by modifying the amino acid sequence of one of the above polypeptides, and evaluating the immunoreactivity of the modified polypeptide. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recite nucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

"Polypeptides" as used herein also include combination, or fusion, polypeptides. A "combination polypeptide" is a polypeptide comprising at least one of the above immunogenic portions and one or more additional immunogenic prostate tumor-specific sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

The prostate tumor proteins of the present invention, and DNA molecules encoding such proteins, may be isolated from prostate tumor tissue using any of a variety of methods well known in the art. DNA sequences corresponding to a gene (of a portion thereof) encoding one of the inventive prostate tumor proteins may be isolated from a prostate tumor cDNA library using a subtraction technique as described in detail below. Examples of such DNA sequences are provided in SEQ ID Nos: 1–107, 109–111, 115–171, 173–175, 177 and 179–224. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.*, 51:263, 1987; Erlich ed., *PCR Technology*, Stockton Press, NY, 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA*, 2:183, 1983).

The prostate tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known prostate antigen, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Polypeptides and/or fusion proteins of the present invention may be used to generate binding agents, such as antibodies or fragments thereof, that are capable of detecting metastatic human prostate tumors. Binding agents of the present invention may generally be prepared using methods known to those of ordinary skill in the art, including the representative procedures described herein. Binding agents are capable of differentiating between patients with and without prostate cancer, using the representative assays described herein. In other words, antibodies or other binding agents raised against a prostate tumor protein, or a suitable portion thereof, will generate a signal indicating the presence of primary or metastatic prostate cancer in at least about 20% of patients afflicted with the disease, and will generate a negative signal indicating the absence of the disease in at least about 90% of individuals without primary or metastatic prostate cancer. Suitable portions of such prostate tumor proteins are portions that are able to generate a binding agent that indicates the presence of primary or metastatic prostate cancer in substantially all (i.e., at least about 80%, and preferably at least about 90%) of the patients for which prostate cancer would be indicated using the full length protein, and that indicate the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

The ability of a polypeptide and/or fusion protein prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 20% of primary or metastatic prostate tumors by such procedures are considered to be useful in assays for detecting primary or metastatic human prostate tumors. Polypeptide specific antibodies may be used alone or in combination to improve sensitivity.

Polypeptides and/or fusion proteins capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include blood, sera, urine and/or prostate secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate prostate tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify prostate tumor-specific cDNA derived from a biological sample, wherein at least one of the oligonucleotide primers is specific for a DNA molecule encoding a prostate tumor protein of the present invention. The presence of the amplified cDNA is then detected using techniques well known in the art, such as gel electrophoresis. Similarly, oligonucleotide probes specific for a DNA molecule encoding a prostate tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule having a sequence selected from SEQ ID Nos: 1–107, 109–111, 115–171, 173–175, 177 and 179–224. Preferably, oligonucleotide probes for use in the inventive diagnostic methods comprise at least about 15 contiguous oligonucleotides of a DNA molecule having a sequence provided in SEQ ID Nos: 1–107, 109–111, 115–171, 173–175, 177 and 179–224. Techniques for both PCR based assays and hybridization assays are well known in the art (see, for example, Mullis et al. Ibid; Ehrlich, Ibid). Primers or probes may thus be used to detect prostate tumor-specific sequences in biological samples, including blood, semen, prostate tissue and/or prostate tumor tissue.

Polypeptides of the present invention that comprise an immunogenic portion of a prostate tumor protein may also be used for immunotherapy of prostate cancer, wherein the polypeptide stimulates the patient's own immune response to prostate tumor cells. In further aspects, the present invention provides methods for using one or more of the immunoreactive polypeptides encoded by a DNA molecule having a sequence provided in SEQ ID NO: 1–107, 109–111, 115–171, 173–175, 177 and 179–224 (or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides may be used to treat prostate cancer or to inhibit the development of prostate cancer. The polypeptides may be administered either prior to or following surgical removal of primary tumors and/or treatment by administration of radiotherapy and conventional chemotherapeutic drugs.

In these aspects, the polypeptide is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such as an adjuvant, biodegradable microsphere (e.g., polylactic galactide) or a liposome (into which the polypeptide is incorporated). Pharmaceutical compositions and vaccines may also contain other epitopes of prostate tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus-Calmette-Guerrin*) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

The following Examples are offered by way of illustration and not by way of limitation.

EXAMPLES

Example 1

Isolation and Characterization of Prostate Tumor Polypeptides

This Example describes the isolation of prostate tumor polypeptides from a prostate tumor cDNA library.

A human prostate tumor cDNA expression library was constructed from prostate tumor poly $A^+$ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 µg) was digested with EcoRI, NotI, and SfuI, followed by a filling-in reaction with DNA polymerase Klenow fragment. After phenol-chloroform extraction and ethanol precipitation, the DNA was dissolved in 100 µl of $H_2O$, heat-denatured and mixed with 100 µl (100 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 µl) was added and the biotinylation reaction was repeated. After extraction with butanol five times, the DNA was ethanol-precipitated and dissolved in 23 µl $H_2O$ to form the driver DNA.

To form the tracer DNA, 10 µg prostate tumor cDNA library was digested with BamHI and XhoI, phenol chloroform extracted and passed through Chroma spin-400 columns (Clontech). Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK⁺ (Stratagene, La Jolla, Calif. 92037) and transformed into ElectroMax *E. coli* DH10B cells by electroporation to generate a prostate tumor specific subtracted cDNA library(prostate subtraction 1.

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID No: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 µg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID Nos: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID Nos: 30–40, respectively. Comparison of these sequences with those in the gene bank as described above, revealed no significant homologies to three of the five most abundant DNA species, (J1-17, L1-12 and N1-1862; SEQ ID Nos: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID Nos:31, 34, 36 and 40, respectively) were found to be identical to previously identified sequences, two (J1-21 and N1-1860; SEQ ID Nos: 32 and 38, respectively) were found to show some homology to non-human sequences, and two (L1-2 and N1-1861; SEQ ID Nos: 35 and 39, respectively) were found to show some homology to known human sequences. No significant homologies were found to the polypeptides J1-13, J1-19, J1-24, J1-25, K1-58, K1-63, L1-4, L1-14 (SEQ ID Nos: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively). Further analysis of the isolated clones led to the determination of extended cDNA sequences for 1G-4736, 1 G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Example 2

Determination of Tissue Specificity of Prostate Tumor Polypeptides

Using gene specific primers, mRNA expression levels for the representative prostate tumor polypeptides F1-16, H1-1, J1-17, L1-12, F1-12 and N1-1862 were examined in a variety of normal and tumor tissues using RT-PCR.

Briefly, total RNA was extracted from a variety of normal and tumor tissues using Trizol reagent as described above. First strand synthesis was carried out using 1–2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 and L1-12 appear to be specifically over-expressed in prostate, with both genes being expressed at high levels in prostate tumor and normal prostate but at low to undetectable levels in all the other tissues examined. N1-1862 was found to be over-expressed in 60% of prostate tumors and detectable in normal colon and kidney. The RT-PCR results thus indicate that F1-16, H1-1, J1-17, N1-1862 and L1-12 are either prostate specific or are expressed at significantly elevated levels in prostate.

Further RT-PCR studies showed that F1-12 is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 is over-expressed in prostate tumors and normal prostate, while being undetectable in other normal tissues tested. J1-17 was detected in two prostate tumors and not in the other tissues tested. N1-1862 was found to be over-expressed in three prostate tumors and to be expressed in normal prostate, colon and kidney, but not in other tissues tested. F1-12 was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 was found to be over-expressed in normal prostate and prostate tumor, with some expression being detected in normal skeletal muscle. Both J1-12 and F1-12 were found to be over-expressed in prostate tumor, with expression being lower or undetectable in all other tissues tested. N1-1862 was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Example 3

Isolation and Characterization of Prostate Tumor Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' *E. coli* (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79, and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. An additional clone, referred to as P703, was found to have five splice variants. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCT as described above. Expression was examined in one sample of each tissue type unless otherwise indicated.

P9 was found to be highly expressed in normal prostate and prostate tumor compared to all normal tissues tested except for normal colon which showed comparable expression. P20 was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies using the above methodology resulted in the isolation of sixteen additional clones. The determined DNA sequences for these clones are provided in SEQ ID NO: 207–222.

Example 4

Synthesis of Polypeptides

Polypeptides may be synthesized on an Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. A method for detecting prostate cancer in a patient comprising:

(a) obtaining a biological sample from the patient;

(b) contacting the sample with at least two oligonucleotide primers in a polymerase chain reaction, wherein said oligonucleotide primers are specific for nucleotide residues 1341–2694 of SEQ ID NO:110 an full length complements of nucleotide residues 1341–2694 of SEQ ID NO:110; and (c) detecting in the sample an expressed polynucleotide sequence that amplifies in the presence of the oligonucleotide primers thereby detecting prostate cancer, wherein the biological sample is selected from the group consisting of blood and semen; wherein the oligonucleotide primers consist of fragments of nucleotide residues 1341–2694 of SEQ ID NO:110; and wherein the fragments consist of at least about 10 contiguous nucleotides of nucleotide residues 1341–2694 of SEQ ID NO:110, or full length complements of nucleotide residues 1341–2694 of SEQ ID NQ:110.

2. A method for detecting the presence of an expressed polynucleotide sequence of SEQ ID NO: 110 in a biological sample, the method comprising:

(a) contacting the sample with at least two oligonucleotide primers in a polymerase chain reaction, wherein the oligonucleotide primers are specific for nucleotide residues 1341–2694 of SEQ ID NO:110 and full length complements of nucleotide residues 1341–2694 of SEQ ID NO:110; and (c) detecting in the sample an expressed polynucleotide sequence that amplifies in the presence of the oligonucleotide primers thereby detecting prostate cancer, wherein the biological sample is selected from the group consisting of blood and semen; wherein the oligonucleotide primers consist of fragments of nucleotide residues 1341–2694 of SEQ ID NO:110; and wherein the fragments consist of at least about 10 contiguous nucleotides of nucleotide residues 1341–2694 of SEQ ID NO:110, or full length complements of nucleotide residues 1341–2694 of SEQ ID NO:110.

* * * * *

UNITED STATES PATENT AND TRADEMARK OFFICE
CERTIFICATE OF CORRECTION

PATENT NO. : 6,887,660 B2
DATED : May 3, 2005
INVENTOR(S) : Jiangchun Xu

It is certified that error appears in the above-identified patent and that said Letters Patent is hereby corrected as shown below:

Column 207,
Line 29, "an" should read as -- and --.

Signed and Sealed this

Thirteenth Day of September, 2005

JON W. DUDAS
*Director of the United States Patent and Trademark Office*

SEQUENCE LISTING (1) GENERAL INFORMATION:

(iii) NUMBER OF SEQUENCES: 224

(2) INFORMATION FOR SEQ ID NO:1:

(i) SEQUENCE CHARACTERISTICS:
      (A) LENGTH: 814 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
TTTTTTTTTT TTTTTCACAG TATAACAGCT CTTTATTTCT GTGAGTTCTA CTAGGAAATC      60

ATCAAATCTG AGGGTTGTCT GGAGGACTTC AATACACCTC CCCCCATAGT GAATCAGCTT     120

CCAGGGGGTC CAGTCCCTCT CCTTACTTCA TCCCCATCCC ATGCCAAAGG AAGACCCTCC     180

CTCCTTGGCT CACAGCCTTC TCTAGGCTTC CCAGTGCCTC CAGGACAGAG TGGGTTATGT     240

TTTCAGCTCC ATCCTTGCTG TGAGTGTCTG GTGCGTTGTG CCTCCAGCTT CTGCTCAGTG     300
```

-continued

| | |
|---|---|
| CTTCATGGAC AGTGTCCAGC ACATGTCACT CTCCACTCTC TCAGTGTGGA TCCACTAGTT | 360 |
| CTAGAGCGGC CGCCACCGCG GTGGAGCTCC AGCTTTTGTT CCCTTTAGTG AGGGTTAATT | 420 |
| GCGCGCTTGG CGTAATCATG GTCATAACTG TTTCCTGTGT GAAATTGTTA TCCGCTCACA | 480 |
| ATTCCACACA ACATACGAGC CGGAAGCATA AAGTGTAAAG CCTGGGGTGC CTAATGAGTG | 540 |
| ANCTAACTCA CATTAATTGC GTTGCGCTCA CTGNCCGCTT TCCAGTCNGG AAAACTGTCG | 600 |
| TGCCAGCTGC ATTAATGAAT CGGCCAACGC NCGGGGAAAA GCGGTTTGCG TTTTGGGGGC | 660 |
| TCTTCCGCTT CTCGCTCACT NANTCCTGCG CTCGGTCNTT CGGCTGCGGG GAACGGTATC | 720 |
| ACTCCTCAAA GGNGGTATTA CGGTTATCCN NAAATCNGGG GATACCCNGG AAAAAANTTT | 780 |
| AACAAAAGGG CANCAAAGGG CNGAAACGTA AAAA | 814 |

(2) INFORMATION FOR SEQ ID NO:2:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | |
|---|---|
| ACAGAAATGT TGGATGGTGG AGCACCTTTC TATACGACTT ACAGGACAGC AGATGGGGAA | 60 |
| TTCATGGCTG TTGGAGCAAT AGAACCCCAG TTCTACGAGC TGCTGATCAA AGGACTTGGA | 120 |
| CTAAAGTCTG ATGAACTTCC CAATCAGATG AGCATGGATG ATTGGCCAGA AATGAAGAAG | 180 |
| AAGTTTGCAG ATGTATTTGC AAAGAAGACG AAGGCAGAGT GGTGTCAAAT CTTTGACGGC | 240 |
| ACAGATGCCT GTGTGACTCC GGTTCTGACT TTTGAGGAGG TTGTTCATCA TGATCACAAC | 300 |
| AAGGAACGGG GCTCGTTTAT CACCAGTGAG GAGCAGGACG TGAGCCCCCG CCCTGCACCT | 360 |
| CTGCTGTTAA ACACCCCAGC CATCCCTTCT TTCAAAAGGG ATCCACTAGT TCTAGAAGCG | 420 |
| GCCGCCACCG CGGTGGAGCT CCAGCTTTTG TTCCCTTTAG TGAGGGTTAA TTGCGCGCTT | 480 |
| GGCGTAATCA TGGTCATAGC TGTTTCCTGT GTGAAATTGT TATCCGCTCA CAATTCCCCC | 540 |
| AACATACGAG CCGGAACATA AAGTGTTAAG CCTGGGGTGC CTAATGANTG AGCTAACTCN | 600 |
| CATTAATTGC GTTGCGCTCA CTGCCCGCTT TCCAGTCGGG AAAACTGTCG TGCCACTGCN | 660 |
| TTANTGAATC NGCCACCCCC CGGGAAAAGG CGGTTGCNTT TTGGGCCTCT TCCGCTTTCC | 720 |
| TCGCTCATTG ATCCTNGCNC CCGGTCTTCG GCTGCGGNGA ACGGTTCACT CCTCAAAGGC | 780 |
| GGTNTNCCGG TTATCCCCAA ACNGGGGATA CCCNGA | 816 |

(2) INFORMATION FOR SEQ ID NO:3:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

| | |
|---|---|
| CTTTTGAAAG AAGGGATGGC TGGGGTGTTT AACAGCAGAG GTGCAGGGCG GGGGCTCACG | 60 |
| TCCTGCTCCT CACTGGTGAT AAACGAGCCC CGTTCCTTGT TGTGATCATG ATGAACAACC | 120 |
| TCCTCAAAAG TCAGAACCGG AGTCACACAG GCATCTGTGC CGTCAAAGAT TTGACACCAC | 180 |

-continued

```
TCTGCCTTCG TCTTCTTTGC AAATACATCT GCAAACTTCT TCTTCATTTC TGGCCAATCA      240

TCCATGCTCA TCTGATTGGG AAGTTCATCA GACTTTAGTC CANNTCCTTT GATCAGCAGC      300

TCGTAGAACT GGGGTTCTAT TGCTCCAACA GCCATGAATT CCCCATCTGC TGTCCTGTAA      360

GTCGTATAGA AAGGTGCTCC ACCATCCAAC ATGTTCTGTC CTCGAGGGGG GGCCCGGTAC      420

CCAATTCGCC CTATANTGAG TCGTATTACG CGCGCTCACT GGCCGTCGTT TTACAACGTC      480

GTGACTGGGA AAACCCTGGG CGTTACCAAC TTAATCGCCT TGCAGCACAT CCCCCTTTCG      540

CCAGCTGGGC GTAATANCGA AAAGGCCCGC ACCGATCGCC CTTCCAACAG TTGCGCACCT      600

GAATGGGNAA ATGGGACCCC CCTGTTACCG CGCATTNAAC CCCCGCNGGG TTTNGTTGTT      660

ACCCCCACNT NNACCGCTTA CACTTTGCCA GCGCCTTANC GCCCGCTCCC TTTCNCCTTT      720

CTTCCCTTCC TTTCNCNCCN CTTTCCCCCG GGGTTTCCCC CNTCAAACCC CNA            773
```

(2) INFORMATION FOR SEQ ID NO:4:

(i) SEQUENCE CHARACTERISTICS:
        (A) LENGTH: 828 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CCTCCTGAGT CCTACTGACC TGTGCTTTCT GGTGTGGAGT CCAGGGCTGC TAGGAAAAGG       60

AATGGGCAGA CACAGGTGTA TGCCAATGTT TCTGAAATGG GTATAATTTC GTCCTCTCCT      120

TCGGAACACT GGCTGTCTCT GAAGACTTCT CGCTCAGTTT CAGTGAGGAC ACACACAAAG      180

ACGTGGGTGA CCATGTTGTT TGTGGGGTGC AGAGATGGGA GGGGTGGGGC CCACCCTGGA      240

AGAGTGGACA GTGACACAAG GTGGACACTC TCTACAGATC ACTGAGGATA AGCTGGAGCC      300

ACAATGCATG AGGCACACAC ACAGCAAGGA TGACNCTGTA AACATAGCCC ACGCTGTCCT      360

GNGGGCACTG GGAAGCCTAN ATNAGGCCGT GAGCANAAAG AAGGGGAGGA TCCACTAGTT      420

CTANAGCGGC CGCCACCGCG GTGGANCTCC ANCTTTTGTT CCCTTTAGTG AGGGTTAATT      480

GCGCGCTTGG CNTAATCATG GTCATANCTN TTTCCTGTGT GAAATTGTTA TCCGCTCACA      540

ATTCCACACA ACATACGANC CGGAAACATA AANTGTAAAC CTGGGGTGCC TAATGANTGA      600

CTAACTCACA TTAATTGCGT TGCGCTCACT GCCCGCTTTC CAATCNGGAA ACCTGTCTTG      660

CCNCTTGCAT TNATGAATCN GCCAACCCCC GGGGAAAAGC GTTTGCGTTT TGGGCGCTCT      720

TCCGCTTCCT CNCTCANTTA NTCCCTNCNC TCGGTCATTC CGGCTGCNGC AAACCGGTTC      780

ACCNCCTCCA AAGGGGGTAT TCCGGTTTCC CCNAATCCGG GGANANCC                  828
```

(2) INFORMATION FOR SEQ ID NO:5:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
TTTTTTTTTT TTTTTACTGA TAGATGGAAT TTATTAAGCT TTTCACATGT GATAGCACAT       60

AGTTTTAATT GCATCCAAAG TACTAACAAA AACTCTAGCA ATCAAGAATG GCAGCATGTT      120

ATTTTATAAC AATCAACACC TGTGGCTTTT AAAATTTGGT TTTCATAAGA TAATTTATAC      180
```

```
TGAAGTAAAT CTAGCCATGC TTTTAAAAAA TGCTTTAGGT CACTCCAAGC TTGGCAGTTA      240

ACATTTGGCA TAAACAATAA TAAAACAATC ACAATTTAAT AAATAACAAA TACAACATTG      300

TAGGCCATAA TCATATACAG TATAAGGAAA AGGTGGTAGT GTTGAGTAAG CAGTTATTAG      360

AATAGAATAC CTTGGCCTCT ATGCAAATAT GTCTAGACAC TTTGATTCAC TCAGCCCTGA      420

CATTCAGTTT TCAAAGTAGG AGACAGGTTC TACAGTATCA TTTTACAGTT TCCAACACAT      480

TGAAAACAAG TAGAAAATGA TGAGTTGATT TTTATTAATG CATTACATCC TCAAGAGTTA      540

TCACCAACCC CTCAGTTATA AAAAATTTTC AAGTTATATT AGTCATATAA CTTGGTGTGC      600

TTATTTTAAA TTAGTGCTAA ATGGATTAAG TGAAGACAAC AATGGTCCCC TAATGTGATT      660

GATATTGGTC ATTTTTACCA GCTTCTAAAT CTNAACTTTC AGGCTTTTGA ACTGAACAT       720

TGNATNACAG TGTTCCANAG TTNCAACCTA CTGGAACATT ACAGTGTGCT TGATTCAAAA      780

TGTTATTTTG TTAAAAATTA AATTTTAACC TGGTGGAAAA ATAATTTGAA ATNA            834

(2) INFORMATION FOR SEQ ID NO:6:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TTTTTTTTTT TTTTTTTTTT AAGACCCTCA TCAATAGATG GAGACATACA GAAATAGTCA      60

AACCACATCT ACAAAATGCC AGTATCAGGC GGCGGCTTCG AAGCCAAAGT GATGTTTGGA      120

TGTAAAGTGA ATATTAGTT GGCGGATGAA GCAGATAGTG AGGAAAGTTG AGCCAATAAT       180

GACGTGAAGT CCGTGGAAGC CTGTGGCTAC AAAAAATGTT GAGCCGTAGA TGCCGTCGGA      240

AATGGTGAAG GGAGACTCGA AGTACTCTGA GGCTTGTAGG AGGGTAAAAT AGAGACCCAG      300

TAAAATTGTA ATAAGCAGTG CTTGAATTAT TTGGTTTCGG TTGTTTTCTA TTAGACTATG      360

GTGAGCTCAG GTGATTGATA CTCCTGATGC GAGTAATACG GATGTGTTTA GGAGTGGGAC      420

TTCTAGGGGA TTTAGCGGGG TGATGCCTGT TGGGGGCCAG TGCCCTCCTA GTTGGGGGGT      480

AGGGGCTAGG CTGGAGTGGT AAAAGGCTCA GAAAAATCCT GCGAAGAAAA AAACTTCTGA      540

GGTAATAAAT AGGATTATCC CGTATCGAAG GCCTTTTTGG ACAGGTGGTG TGTGGTGGCC      600

TTGGTATGTG CTTTCTCGTG TTACATCGCG CCATCATTGG TATATGGTTA GTGTGTTGGG      660

TTANTANGGC CTANTATGAA GAACTTTTGG ANTGGAATTA AATCAATNGC TTGGCCGGAA      720

GTCATTANGA NGGCTNAAAA GGCCCTGTTA NGGGTCTGGG CTNGGTTTTA CCCNACCCAT      780

GGAATNCNCC CCCCGGACNA NTGNATCCCT ATTCTTAA                              818

(2) INFORMATION FOR SEQ ID NO:7:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TTTTTTTTTT TTTTTTTTTT TGGCTCTAGA GGGGGTAGAG GGGGTGCTAT AGGGTAAATA      60
```

-continued

```
CGGGCCCTAT TTCAAAGATT TTTAGGGGAA TTAATTCTAG GACGATGGGT ATGAAACTGT      120

GGTTTGCTCC ACAGATTTCA GAGCATTGAC CGTAGTATAC CCCCGGTCGT GTAGCGGTGA      180

AAGTGGTTTG GTTTAGACGT CCGGGAATTG CATCTGTTTT TAAGCCTAAT GTGGGGACAG      240

CTCATGAGTG CAAGACGTCT TGTGATGTAA TTATTATACN AATGGGGGCT TCAATCGGGA      300

GTACTACTCG ATTGTCAACG TCAAGGAGTC GCAGGTCGCC TGGTTCTAGG AATAATGGGG      360

GAAGTATGTA GGAATTGAAG ATTAATCCGC CGTAGTCGGT GTTCTCCTAG GTTCAATACC      420

ATTGGTGGCC AATTGATTTG ATGGTAAGGG GAGGGATCGT TGAACTCGTC TGTTATGTAA      480

AGGATNCCTT NGGGATGGGA AGGCNATNAA GGACTANGGA TNAATGGCGG GCANGATATT      540

TCAAACNGTC TCTANTTCCT GAAACGTCTG AAATGTTAAT AANAATTAAN TTTNGTTATT      600

GAATNTTNNG GAAAAGGGCT TACAGGACTA GAAACCAAAT ANGAAAANTA ATNNTAANGG      660

CNTTATCNTN AAAGGTNATA ACCNCTCCTA TNATCCCACC CAATNGNATT CCCCACNCNN      720

ACNATTGGAT NCCCCANTTC CANAAANGGC CNCCCCCCGG TGNANNCCNC CTTTTGTTCC      780

CTTNANTGAN GGTTATTCNC CCCTNGCNTT ATCANCC                              817
```

(2) INFORMATION FOR SEQ ID NO:8:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
CATTTCCGGG TTTACTTTCT AAGGAAAGCC GAGCGGAAGC TGCTAACGTG GGAATCGGTG       60

CATAAGGAGA ACTTTCTGCT GGCACGCGCT AGGGACAAGC GGGAGAGCGA CTCCGAGCGT      120

CTGAAGCGCA CGTCCCAGAA GGTGGACTTG GCACTGAAAC AGCTGGGACA CATCCGCGAG      180

TACGAACAGC GCCTGAAAGT GCTGGAGCGG GAGGTCCAGC AGTGTAGCCG CGTCCTGGGG      240

TGGGTGGCCG ANGCCTGANC CGCTCTGCCT TGCTGCCCCC ANGTGGGCCG CCACCCCCTG      300

ACCTGCCTGG GTCCAAACAC TGAGCCCTGC TGGCGGACTT CAAGGANAAC CCCCACANGG      360

GGATTTTGCT CCTANANTAA GGCTCATCTG GGCCTCGGCC CCCCCACCTG GTTGGCCTTG      420

TCTTTGANGT GAGCCCCATG TCCATCTGGG CCACTGTCNG GACCACCTTT NGGGAGTGTT      480

CTCCTTACAA CCACANNATG CCCGGCTCCT CCCGGAAACC ANTCCCANCC TGNGAAGGAT      540

CAAGNCCTGN ATCCACTNNT NCTANAACCG GCCNCCNCCG CNGTGGAACC CNCCTTNTGT      600

TCCTTTTCNT TNAGGGTTAA TNNCGCCTTG GCCTTNCCAN NGTCCTNCNC NTTTTCCNNT      660

GTTNAAATTG TTANGCNCCC NCCNNTCCCN CNNCNNCNAN CCCGACCCNN ANNTTNNANN      720

NCCTGGGGGT NCCNNCNGAT TGACCCNNCC NCCCTNTANT TGCNTTNGGG NNCNNTGCCC      780

CTTTCCCTCT NGGGANNCG                                                  799
```

(2) INFORMATION FOR SEQ ID NO:9:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

-continued

```
ACGCCTTGAT CCTCCCAGGC TGGGACTGGT TCTGGGAGGA GCCGGGCATG CTGTGGTTTG      60

TAANGATGAC ACTCCCAAAG GTGGTCCTGA CAGTGGCCCA GATGGACATG GGGCTCACCT     120

CAAGGACAAG GCCACCAGGT GCGGGGGCCG AAGCCCACAT GATCCTTACT CTATGAGCAA     180

AATCCCCTGT GGGGGCTTCT CCTTGAAGTC CGCCANCAGG GCTCAGTCTT TGGACCCANG     240

CAGGTCATGG GGTTGTNGNC CAACTGGGGG CCNCAACGCA AAANGGCNCA GGGCCTCNGN     300

CACCCATCCC ANGACGCGGC TACACTNCTG GACCTCCCNC TCCACCACTT TCATGCGCTG     360

TTCNTACCCG CGNATNTGTC CCANCTGTTT CNGTGCCNAC TCCANCTTCT NGGACGTGCG     420

CTACATACGC CCGGANTCNC NCTCCCGCTT TGTCCCTATC CACGTNCCAN CAACAAATTT     480

CNCCNTANTG CACCNATTCC CACNTTTNNC AGNTTTCCNC NNCGNGCTTC CTTNTAAAAG     540

GGTTGANCCC CGGAAAATNC CCCAAGGGG GGGGGCCNGG TACCCAACTN CCCCCTNATA     600

GCTGAANTCC CCATNACCNN GNCTCNATGG ANCCNTCCNT TTTAANNACN TTCTNAACTT     660

GGGAANANCC CTCGNCCNTN CCCCCNTTAA TCCCNCCTTG CNANGNNCNT CCCCCNNTCC     720

NCCCNNNTNG GCNTNTNANN CNAAAAAGGC CCNNNANCAA TCTCCTNNCN CCTCANTTCG     780

CCANCCCTCG AAATCGGCCN C                                                801
```

(2) INFORMATION FOR SEQ ID NO:10:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CAGTCTATNT GGCCAGTGTG GCAGCTTTCC CTGTGGCTGC CGGTGCCACA TGCCTGTCCC      60

ACAGTGTGGC CGTGGTGACA GCTTCAGCCG CCCTCACCGG GTTCACCTTC TCAGCCCTGC     120

AGATCCTGCC CTACACACTG GCCTCCCTCT ACCACCGGGA GAAGCAGGTG TTCCTGCCCA     180

AATACCGAGG GGACACTGGA GGTGCTAGCA GTGAGGACAG CCTGATGACC AGCTTCCTGC     240

CAGGCCCTAA GCCTGGAGCT CCCTTCCCTA ATGGACACGT GGGTGCTGGA GGCAGTGGCC     300

TGCTCCCACC TCCACCCGCG CTCTGCGGGG CCTCTGCCTG TGATGTCTCC GTACGTGTGG     360

TGGTGGGTGA GCCCACCGAN GCCAGGGTGG TTCCGGGCCG GGGCATCTGC CTGGACCTCG     420

CCATCCTGGA TAGTGCTTCC TGCTGTCCCA NGTGGCCCCA TCCCTGTTTA TGGGCTCCAT     480

TGTCCAGCTC AGCCAGTCTG TCACTGCCTA TATGGTGTCT GCCGCAGGCC TGGGTCTGGT     540

CCCATTTACT TTGCTACACA GGTANTATTT GACAAGAACG ANTTGGCCAA ATACTCAGCG     600

TTAAAAAATT CCAGCAACAT TGGGGGTGGA AGGCCTGCCT CACTGGGTCC AACTCCCCGC     660

TCCTGTTAAC CCCATGGGGC TGCCGGCTTG GCCGCCAATT TCTGTTGCTG CCAAANTNAT     720

GTGGCTCTCT GCTGCCACCT GTTGCTGGCT GAAGTGCNTA CNGCNCANCT NGGGGGGTNG     780

GGNGTTCCC                                                              789
```

(2) INFORMATION FOR SEQ ID NO:11:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | | | | | |
|---|---|---|---|---|---|
| CCCACCCTAC | CCAAATATTA | GACACCAACA | CAGAAAAGCT | AGCAATGGAT | TCCCTTCTAC | 60 |
| TTTGTTAAAT | AAATAAGTTA | AATATTTAAA | TGCCTGTGTC | TCTGTGATGG | CAACAGAAGG | 120 |
| ACCAACAGGC | CACATCCTGA | TAAAAGGTAA | GAGGGGGGTG | GATCAGCAAA | AGACAGTGC | 180 |
| TGTGGGCTGA | GGGGACCTGG | TTCTTGTGTG | TTGCCCCTCA | GGACTCTTCC | CCTACAAATA | 240 |
| ACTTTCATAT | GTTCAAATCC | CATGGAGGAG | TGTTTCATCC | TAGAAACTCC | CATGCAAGAG | 300 |
| CTACATTAAA | CGAAGCTGCA | GGTTAAGGGG | CTTANAGATG | GGAAACCAGG | TGACTGAGTT | 360 |
| TATTCAGCTC | CCAAAAACCC | TTCTCTAGGT | GTGTCTCAAC | TAGGAGGCTA | GCTGTTAACC | 420 |
| CTGAGCCTGG | GTAATCCACC | TGCAGAGTCC | CCGCATTCCA | GTGCATGGAA | CCCTTCTGGC | 480 |
| CTCCCTGTAT | AAGTCCAGAC | TGAAACCCCC | TTGGAAGGNC | TCCAGTCAGG | CAGCCCTANA | 540 |
| AACTGGGGAA | AAAAGAAAAG | GACGCCCCAN | CCCCCAGCTG | TGCANCTACG | CACCTCAACA | 600 |
| GCACAGGGTG | GCAGCAAAAA | AACCACTTTA | CTTTGGCACA | AACAAAAACT | NGGGGGGCA | 660 |
| ACCCCGGCAC | CCCNANGGGG | GTTAACAGGA | ANCNGGGNAA | CNTGGAACCC | AATTNAGGCA | 720 |
| GGCCCNCCAC | CCCNAATNTT | GCTGGGAAAT | TTTTCCTCCC | CTAAATTNTT | TC | 772 |

(2) INFORMATION FOR SEQ ID NO:12:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

| | | | | | |
|---|---|---|---|---|---|
| GCCCCAATTC | CAGCTGCCAC | ACCACCCACG | GTGACTGCAT | TAGTTCGGAT | GTCATACAAA | 60 |
| AGCTGATTGA | AGCAACCCTC | TACTTTTTGG | TCGTGAGCCT | TTTGCTTGGT | GCAGGTTTCA | 120 |
| TTGGCTGTGT | TGGTGACGTT | GTCATTGCAA | CAGAATGGGG | GAAAGGCACT | GTTCTCTTTG | 180 |
| AAGTANGGTG | AGTCCTCAAA | ATCCGTATAG | TTGGTGAAGC | CACAGCACTT | GAGCCCTTTC | 240 |
| ATGGTGGTGT | TCCACACTTG | AGTGAAGTCT | TCCTGGGAAC | CATAATCTTT | CTTGATGGCA | 300 |
| GGCACTACCA | GCAACGTCAG | GGAAGTGCTC | AGCCATTGTG | GTGTACACCA | AGGCGACCAC | 360 |
| AGCAGCTGCN | ACCTCAGCAA | TGAAGATGAN | GAGGANGATG | AAGAAGAACG | TCNCGAGGGC | 420 |
| ACACTTGCTC | TCAGTCTTAN | CACCATANCA | GCCCNTGAAA | ACCAANANCA | AAGACCACNA | 480 |
| CNCCGGCTGC | GATGAAGAAA | TNACCCCNCG | TTGACAAACT | TGCATGGCAC | TGGGANCCAC | 540 |
| AGTGGCCCNA | AAAATCTTCA | AAAAGGATGC | CCCATCNATT | GACCCCCCAA | ATGCCCACTG | 600 |
| CCAACAGGGG | CTGCCCCACN | CNCNNAACGA | TGANCCNATT | GNACAAGATC | TNCNTGGTCT | 660 |
| TNATNAACNT | GAACCCTGCN | TNGTGGCTCC | TGTTCAGGNC | CNNGGCCTGA | CTTCTNAANN | 720 |
| AANGAACTCN | GAAGNCCCCA | CNGGANANNC | G | | | 751 |

(2) INFORMATION FOR SEQ ID NO:13:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GAGCCAGGCG TCCCTCTGCC TGCCCACTCA GTGGCAACAC CCGGGAGCTG TTTTGTCCTT      60
TGTGGANCCT CAGCAGTNCC CTCTTTCAGA ACTCANTGCC AAGANCCCTG AACAGGAGCC     120
ACCATGCAGT GCTTCAGCTT CATTAAGACC ATGATGATCC TCTTCAATTT GCTCATCTTT     180
CTGTGTGGTG CAGCCCTGTT GGCAGTGGGC ATCTGGGTGT CAATCGATGG GGCATCCTTT     240
CTGAAGATCT TCGGGCCACT GTCGTCCAGT GCCATGCAGT TTGTCAACGT GGGCTACTTC     300
CTCATCGCAG CCGGCGTTGT GGTCTTAGCT CTAGGTTTCC TGGGCTGCTA TGGTGCTAAG     360
ACTGAGAGCA AGTGTGCCCT CGTGACGTTC TTCTTCATCC TCCTCCTCAT CTTCATTGCT     420
GAGGTTGCAA TGCTGTGGTC GCCTTGGTGT ACACCACAAT GGCTGAGCAC TTCCTGACGT     480
TGCTGGTAAT GCCTGCCATC AANAAAAGAT TATGGGTTCC CAGGAANACT TCACTCAAGT     540
GTTGGAACAC CACCATGAAA GGGCTCAAGT GCTGTGGCTT CNNCCAACTA TACGGATTTT     600
GAAGANTCAC CTACTTCAAA GAAAANAGTG CCTTTCCCCC ATTTCTGTTG CAATTGACAA     660
ACGTCCCCAA CACAGCCAAT TGAAAACCTG CACCCAACCC AAANGGGTCC CCAACCANAA     720
ATTNAAGGG                                                             729
```

(2) INFORMATION FOR SEQ ID NO:14:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
TGCTCTTCCT CAAAGTTGTT CTTGTTGCCA TAACAACCAC CATAGGTAAA GCGGGCGCAG      60
TGTTCGCTGA AGGGGTTGTA GTACCAGCGC GGGATGCTCT CCTTGCAGAG TCCTGTGTCT     120
GGCAGGTCCA CGCAGTGCCC TTTGTCACTG GGGAAATGGA TGCGCTGGAG CTCGTCAAAG     180
CCACTCGTGT ATTTTTCACA GGCAGCCTCG TCCGACGCGT CGGGGCAGTT GGGGGTGTCT     240
TCACACTCCA GGAAACTGTC NATGCAGCAG CCATTGCTGC AGCGGAACTG GGTGGGCTGA     300
CANGTGCCAG AGCACACTGG ATGGCGCCTT TCCATGNNAN GGGCCCTGNG GGAAAGTCCC     360
TGANCCCCAN ANCTGCCTCT CAAANGCCCC ACCTTGCACA CCCCGACAGG CTAGAATGGA     420
ATCTTCTTCC CGAAAGGTAG TTNTTCTTGT TGCCCAANCC ANCCCCNTAA ACAAACTCTT     480
GCANATCTGC TCCGNGGGGG TCNTANTACC ANCGTGGGAA AAGAACCCCA GGCNGCGAAC     540
CAANCTTGTT TGGATNCGAA GCNATAATCT NCTNTTCTGC TTGGTGGACA GCACCANTNA     600
CTGTNNANCT TTAGNCCNTG GTCCTCNTGG GTTGNNCTTG AACCTAATCN CCNNTCAACT     660
GGGACAAGGT AANTNGCCNT CCTTTNAATT CCCNANCNTN CCCCCTGGTT TGGGGTTTTN     720
CNCNCTCCTA CCCCAGAAAN NCCGTGTTCC CCCCCAACTA GGGGCCNAAA CCNNTTNTTC     780
CACAACCCTN CCCCACCCAC GGGTTCNGNT GGTTNG                               816
```

(2) INFORMATION FOR SEQ ID NO:15:

(i) SEQUENCE CHARACTERISTICS:
        (A) LENGTH: 783 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:15:

```
CCAAGGCCTG GGCAGGCATA NACTTGAAGG TACAACCCCA GGAACCCCTG GTGCTGAAGG         60
ATGTGGAAAA CACAGATTGG CGCCTACTGC GGGGTGACAC GGATGTCAGG GTAGAGAGGA        120
AAGACCCAAA CCAGGTGGAA CTGTGGGGAC TCAAGGAANG CACCTACCTG TTCCAGCTGA        180
CAGTGACTAG CTCAGACCAC CCAGAGGACA CGGCCAACGT CACAGTCACT GTGCTGTCCA        240
CCAAGCAGAC AGAAGACTAC TGCCTCGCAT CCAACAANGT GGGTCGCTGC CGGGGCTCTT        300
TCCCACGCTG GTACTATGAC CCCACGGAGC AGATCTGCAA GAGTTTCGTT TATGGAGGCT        360
GCTTGGGCAA CAAGAACAAC TACCTTCGGG AAGAAGAGTG CATTCTANCC TGTCNGGGTG        420
TGCAAGGTGG GCCTTTGANA NGCANCTCTG GGGCTCANGC GACTTTCCCC CAGGGCCCCT        480
CCATGGAAAG GCGCCATCCA NTGTTCTCTG GCACCTGTCA GCCCACCCAG TTCCGCTGCA        540
NCAATGGCTG CTGCATCNAC ANTTTCCTNG AATTGTGACA ACACCCCCA NTGCCCCCAA         600
CCCTCCCAAC AAAGCTTCCC TGTTNAAAAA TACNCCANTT GGCTTTTNAC AAACNCCCGG        660
CNCCTCCNTT TTCCCCNNTN AACAAAGGGC NCTNGCNTTT GAACTGCCCN AACCCNGGAA        720
TCTNCCNNGG AAAAANTNCC CCCCCTGGTT CCTNNAANCC CCTCCNCNAA ANCTNCCCCC        780
CCC                                                                     783
```

(2) INFORMATION FOR SEQ ID NO:16:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GCCCCAATTC CAGCTGCCAC ACCACCCACG GTGACTGCAT TAGTTCGGAT GTCATACAAA         60
AGCTGATTGA AGCAACCCTC TACTTTTTGG TCGTGAGCCT TTTGCTTGGT GCAGGTTTCA        120
TTGGCTGTGT TGGTGACGTT GTCATTGCAA CAGAATGGGG GAAAGGCACT GTTCTCTTTG        180
AAGTAGGGTG AGTCCTCAAA ATCCGTATAG TTGGTGAAGC CACAGCACTT GAGCCCTTTC        240
ATGGTGGTGT TCCACACTTG AGTGAAGTCT TCCTGGGAAC CATAATCTTT CTTGATGGCA        300
GGCACTACCA GCAACGTCAG GAAGTGCTCA GCCATTGTGG TGTACACCAA GGCGACCACA        360
GCAGCTGCAA CCTCAGCAAT GAAGATGAGG AGGAGGATGA AGAAGAACGT CNCGAGGGCA        420
CACTTGCTCT CCGTCTTAGC ACCATAGCAG CCCANGAAAC CAAGAGCAAA GACCACAACG        480
CCNGCTGCGA ATGAAAGAAA NTACCCACGT TGACAAACTG CATGGCCACT GGACGACAGT        540
TGGCCCGAAN ATCTTCAGAA AAGGGATGCC CCATCGATTG AACACCCANA TGCCCACTGC        600
CNACAGGGCT GCNCCNCNCN GAAAGAATGA GCCATTGAAG AAGGATCNTC NTGGTCTTAA        660
TGAACTGAAA CCNTGCATGG TGGCCCCTGT TCAGGGCTCT TGGCAGTGAA TTCTGANAAA        720
AAGGAACNGC NTNAGCCCCC CCAAANGANA AAACACCCCC GGGTGTTGCC CTGAATTGGC        780
GGCCAAGGAN CCCTGCCCCN G                                                 801
```

(2) INFORMATION FOR SEQ ID NO:17:

(i) SEQUENCE CHARACTERISTICS:
        (A) LENGTH: 740 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:17:

```
GTGAGAGCCA GGCGTCCCTC TGCCTGCCCA CTCAGTGGCA ACACCCGGGA GCTGTTTTGT      60

CCTTTGTGGA GCCTCAGCAG TTCCCTCTTT CAGAACTCAC TGCCAAGAGC CCTGAACAGG     120

AGCCACCATG CAGTGCTTCA GCTTCATTAA GACCATGATG ATCCTCTTCA ATTTGCTCAT     180

CTTTCTGTGT GGTGCAGCCC TGTTGGCAGT GGGCATCTGG GTGTCAATCG ATGGGGCATC     240

CTTTCTGAAG ATCTTCGGGC CACTGTCGTC CAGTGCCATG CAGTTTGTCA ACGTGGGCTA     300

CTTCCTCATC GCAGCCGGCG TTGTGGTCTT TGCTCTTGGT TTCCTGGGCT GCTATGGTGC     360

TAAGACGGAG AGCAAGTGTG CCCTCGTGAC GTTCTTCTTC ATCCTCCTCC TCATCTTCAT     420

TGCTGAAGTT GCAGCTGCTG TGGTCGCCTT GGTGTACACC ACAATGGCTG AACCATTCCT     480

GACGTTGCTG GTANTGCCTG CCATCAANAA AGATTATGGG TTCCCAGGAA AAATTCACTC     540

AANTNTGGAA CACCNCCATG AAAAGGGCTC CAATTTCTGN TGGCTTCCCC AACTATACCG     600

GAATTTTGAA AGANTCNCCC TACTTCCAAA AAAAAANANT TGCCTTTNCC CCCNTTCTGT     660

TGCAATGAAA ACNTCCCAAN ACNGCCAATN AAAACCTGCC CNNNCAAAAA GGNTCNCAAA     720

CAAAAAAANT NNAAGGGTTN                                                 740
```

(2) INFORMATION FOR SEQ ID NO:18:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
CCGCTGGTTG CGCTGGTCCA GNGNAGCCAC GAAGCACGTC AGCATACACA GCCTCAATCA      60

CAAGGTCTTC CAGCTGCCGC ACATTACGCA GGGCAAGAGC CTCCAGCAAC ACTGCATATG     120

GGATACACTT TACTTTAGCA GCCAGGGTGA CAACTGAGAG GTGTCGAAGC TTATTCTTCT     180

GAGCCTCTGT TAGTGGAGGA AGATTCCGGG CTTCAGCTAA GTAGTCAGCG TATGTCCCAT     240

AAGCAAACAC TGTGAGCAGC CGGAAGGTAG AGGCAAAGTC ACTCTCAGCC AGCTCTCTAA     300

CATTGGGCAT GTCCAGCAGT TCTCCAAACA CGTAGACACC AGNGGCCTCC AGCACCTGAT     360

GGATGAGTGT GGCCAGCGCT GCCCCCTTGG CCGACTTGGC TAGGAGCAGA AATTGCTCCT     420

GGTTCTGCCC TGTCACCTTC ACTTCCGCAC TCATCACTGC ACTGAGTGTG GGGGACTTGG     480

GCTCAGGATG TCCAGAGACG TGGTTCCGCC CCCTCNCTTA ATGACACCGN CCANNCAACC     540

GTCGGCTCCC GCCGANTGNG TTCGTCGTNC CTGGGTCAGG GTCTGCTGGC CNCTACTTGC     600

AANCTTCGTC NGGCCCATGG AATTCACCNC ACCGGAACTN GTANGATCCA CTNNTTCTAT     660

AACCGGNCGC CACCGCNNNT GGAACTCCAC TCTTNTTNCC TTTACTTGAG GGTTAAGGTC     720

ACCCTTNNCG TTACCTTGGT CCAAACCNTN CCNTGTGTCG ANATNGTNAA TCNGGNCCNA     780

TNCCANCCNC ATANGAAGCC NG                                              802
```

(2) INFORMATION FOR SEQ ID NO:19:

(i) SEQUENCE CHARACTERISTICS:
        (A) LENGTH: 731 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
CNAAGCTTCC AGGTNACGGG CCGCNAANCC TGACCCNAGG TANCANAANG CAGNCNGCGG    60
GAGCCCACCG TCACGNGGNG GNGTCTTTAT NGGAGGGGGC GGAGCCACAT CNCTGGACNT   120
CNTGACCCCA ACTCCCCNCC NCNCANTGCA GTGATGAGTG CAGAACTGAA GGTNACGTGG   180
CAGGAACCAA GANCAAANNC TGCTCCNNTC CAAGTCGGCN NAGGGGGCGG GGCTGGCCAC   240
GCNCATCCNT CNAGTGCTGN AAAGCCCCNN CCTGTCTACT TGTTTGGAGA ACNGCNNNGA   300
CATGCCCAGN GTTANATAAC NGGCNGAGAG TNANTTTGCC TCTCCCTTCC GGCTGCGCAN   360
CGNGTNTGCT TAGNGGACAT AACCTGACTA CTTAACTGAA CCCNNGAATC TNCCNCCCCT   420
CCACTAAGCT CAGAACAAAA AACTTCGACA CCACTCANTT GTCACCTGNC TGCTCAAGTA   480
AAGTGTACCC CATNCCCAAT GTNTGCTNGA NGCTCTGNCC TGCNTTANGT TCGGTCCTGG   540
GAAGACCTAT CAATTNAAGC TATGTTTCTG ACTGCCTCTT GCTCCCTGNA ACAANCNACC   600
CNNCNNTCCA AGGGGGGGNC GGCCCCCAAT CCCCCCAACC NTNAATTNAN TTTANCCCCN   660
CCCCCNGGCC CGGCCTTTTA CNANCNTCNN NNACNGGGNA AAACCNNNGC TTTNCCCAAC   720
NNAATCCNCC T                                                       731
```

(2) INFORMATION FOR SEQ ID NO:20:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
TTTTTTTTTT TTTTTTTTTT TAAAAACCCC CTCCATTNAA TGNAAACTTC CGAAATTGTC    60
CAACCCCCTC NTCCAAATNN CCNTTTCCGG GNGGGGGTTC CAAACCCAAN TTANNTTTGG   120
ANNTTAAATT AAATNTTNNT TGGNGGNNNA ANCCNAATGT NANGAAAGTT NAACCCANTA   180
TNANCTTNAA TNCCTGGAAA CCNGTNGNTT CCAAAAATNT TTAACCCTTA ANTCCCTCCG   240
AAAATNGTTNA NGGAAAACCC AANTTCTCNT AAGGTTGTTT GAAGGNTAAA TNAAAANCCC   300
NNCCAATTGT TTTTNGCCAC GCCTGAATTA ATTGGNTTCC GNTGTTTTCC NTTAAAANAA   360
GGNNANCCCC GGTTANTNAA TCCCCCCNNC CCCAATTATA CCGANTTTTT TTNGAATTGG   420
GANCCCNCGG GAATTAACGG GGNNNNTCCC TNTTGGGGGG CNGGNNCCCC CCCCNTCGGG   480
GGTTNGGGNC AGGNCNNAAT TGTTTAAGGG TCCGAAAAAT CCCTCCNAGA AAAAAANCTC   540
CCAGGNTGAG NNTNGGGTTT NCCCCCCCCC CANGGCCCCT CTCGNANAGT TGGGGTTTGG   600
GGGGCCTGGG ATTTTNTTTC CCCTNTTNCC TCCCCCCCCC CCNGGGANAG AGGTTNGNGT   660
TTTGNTCNNC GGCCCCNCCN AAGANCTTTN CCGANTTNAN TTAAATCCNT GCCTNGGCGA   720
AGTCCNTTGN AGGGNTAAAN GGCCCCCTNN CGGG                              754
```

(2) INFORMATION FOR SEQ ID NO:21:

(i) SEQUENCE CHARACTERISTICS:
        (A) LENGTH: 755 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:21:

ATCANCCCAT GACCCCNAAC NNGGGACCNC TCANCCGGNC NNNCNACCNC CGGCCNATCA      60

NNGTNAGNNC ACTNCNNTTN NATCACNCCC CNCCNACTAC GCCCNCNANC CNACGCNCTA     120

NNCANATNCC ACTGANNGCG CGANGTNGAN NGAGAAANCT NATACCANAG NCACCANACN     180

CCAGCTGTCC NANAANGCCT NNNATACNGG NNNATCCAAT NTGNANCCTC CNAAGTATTN     240

NNCNNCANAT GATTTTCCTN ANCCGATTAC CCNTNCCCCC TANCCCCTCC CCCCCAACNA     300

CGAAGGCNCT GGNCCNAAGG NNGCGNCNCC CCGCTAGNTC CCCNNCAAGT CNCNCNCCTA     360

AACTCANCCN NATTACNCGC TTCNTGAGTA TCACTCCCCG AATCTCACCC TACTCAACTC     420

AAAAANATCN GATACAAAAT AATNCAAGCC TGNTTATNAC ACTNTGACTG GGTCTCTATT     480

TTAGNGGTCC NTNAANCNTC CTAATACTTC CAGTCTNCCT TCNCCAATTT CCNAANGGCT     540

CTTTCNGACA GCATNTTTTG GTTCCCNNTT GGGTTCTTAN NGAATTGCCC TTCNTNGAAC     600

GGGCTCNTCT TTTCCTTCGG TTANCCTGGN TTCNNCCGGC CAGTTATTAT TTCCCNTTTT     660

AAATTCNTNC CNTTTANTTT TGGCNTTCNA AACCCCCGGC CTTGAAAACG GCCCCCTGGT     720

AAAAGGTTGT TTTGANAAAA TTTTTGTTTT GTTCC                               755

(2) INFORMATION FOR SEQ ID NO:22:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TTTTTTTTTT TTTTANGTG TNGTCGTGCA GGTAGAGGCT TACTACAANT GTGAANACGT       60

ACGCTNGGAN TAANGCGACC CGANTTCTAG GANNCNCCCT AAAATCANAC TGTGAAGATN     120

ATCCTGNNNA CGGAANGGTC ACCGGNNGAT NNTGCTAGGG TGNCCNCTCC CANNNCNTTN     180

CATAACTCNG NGGCCCTGCC CACCACCTTC GGCGGCCCNG NGNCCGGGCC CGGGTCATTN     240

GNNTTAACCN CACTNNGCNA NCGGTTTCCN NCCCCNNCNG ACCCNGGCGA TCCGGGGTNC     300

TCTGTCTTCC CCTGNAGNCN ANAAANTGGG CCNCGGNCCC CTTTACCCCT NNACAAGCCA     360

CNGCCNTCTA NCCNCNGCCC CCCCTCCANT NNGGGGGACT GCCNANNGCT CCGTTNCTNG     420

NNACCCCNNN GGGTNCCTCG GTTGTCGANT CNACCGNANG CCANGGATTC CNAAGGAAGG     480

TGCGTTNTTG GCCCCTACCC TTCGCTNCGG NNCACCCTTC CCGACNANGA NCCGCTCCCG     540

CNCNNCGNNG CCTCNCCTCG CAACACCCGC NCTCNTCNGT NCGGNNNCCC CCCCACCCGC     600

NCCCTCNCNC NGNCGNANCN CTCCNCCNCC GTCTCANNCA CCACCCCGCC CCGCCAGGCC     660

NTCANCCACN GGNNGACNNG NAGCNCNNTC GCNCCGCGCN GCGNCNCCCT CGCCNCNGAA     720

CTNCNTCNGG CCANTNNCGC TCAANCCNNA CNAAACGCCG CTGCGCGGCC CGNAGCGNCC     780

NCCTCCNCGA GTCCTCCCGN CTTCCNACCC ANGNNTTCCN CGAGGACACN NNACCCCGCC     840

NNCANGCGG                                                            849

(2) INFORMATION FOR SEQ ID NO:23:

(i) SEQUENCE CHARACTERISTICS:
    (A) LENGTH: 872 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:23:

```
GCGCAAACTA TACTTCGCTC GNACTCGTGC GCCTCGCTNC TCTTTTCCTC CGCAACCATG    60

TCTGACNANC CCGATTNGGC NGATATCNAN AAGNTCGANC AGTCCAAACT GANTAACACA   120

CACACNCNAN AGANAAATCC NCTGCCTTCC ANAGTANACN ATTGAACNNG AGAACCANGC   180

NGGCGAATCG TAATNAGGCG TGCGCCGCCA ATNTGTCNCC GTTTATTNTN CCAGCNTCNC   240

CTNCCNACCC TACNTCTTCN NAGCTGTCNN ACCCCTNGTN CGNACCCCCC NAGGTCGGGA   300

TCGGGTTTNN NNTGACCGNG CNNCCCCTCC CCCCNTCCAT NACGANCCNC CCGCACCACC   360

NANNGCNCGC NCCCCGNNCT CTTCGCCNCC CTGTCCTNTN CCCCTGTGCC CTGGCNCNGN   420

ACCGCATTGA CCCTCGCCNN CTNCNNGAAA NCGNANACGT CCGGGTTGNN ANNANCGCTG   480

TGGGNNNGCG TCTGCNCCGC GTTCCTTCCN NCNNCTTCCA CCATCTTCNT TACNGGGTCT   540

CCNCGCCNTC TCNNNCACNC CCTGGGACGC TNTCCTNTGC CCCCCTTNAC TCCCCCCCTT   600

CGNCGTGNCC CGNCCCCACC NTCATTTNCA NACGNTCTTC ACAANNNCCT GGNTNNCTCC   660

CNANCNGNCN GTCANCCNAG GGAAGGGNGG GGNNCCNNTG NTTGACGTTG NGGNGANGTC   720

CGAANANTCC TCNCCNTCAN CNCTACCCCT CGGGCGNNCT CTCNGTTNCC AACTTANCAA   780

NTCTCCCCCG NGNGCNCNTC TCAGCCTCNC CCNCCCCNCT CTCTGCANTG TNCTCTGCTC   840

TNACCNNTAC GANTNTTCGN CNCCCTCTTT CC                                 872
```

(2) INFORMATION FOR SEQ ID NO:24:

(i) SEQUENCE CHARACTERISTICS:
    (A) LENGTH: 815 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:24:

```
GCATGCAAGC TTGAGTATTC TATAGNGTCA CCTAAATANC TTGGCNTAAT CATGGTCNTA    60

NCTGNCTTCC TGTGTCAAAT GTATACNAAN TANATATGAA TCTNATNTGA CAAGANNGTA   120

TCNTNCATTA GTAACAANTG TNNTGTCCAT CCTGTCNGAN CANATTCCCA TNNATTNCGN   180

CGCATTCNCN GCNCANTATN TAATNGGGAA NTCNNNTNNN NCACCNNCAT CTATCNTNCC   240

GCNCCCTGAC TGGNAGAGAT GGATNANTTC TNNTNTGACC NACATGTTCA TCTTGGATTN   300

AANANCCCCC CGCNGNCCAC CGGTTNGNNG CNAGCCNNTC CCAAGACCTC CTGTGGAGGT   360

AACCTGCGTC AGANNCATCA AACNTGGGAA ACCCGCNNCC ANGTNNAAGT NGNNNCANAN   420

GATCCCGTCC AGGNTTNACC ATCCCTTCNC AGCGCCCCCT TTNGTGCCTT ANAGNGNAGC   480

GTGTCCNANC CNCTCAACAT GANACGCGCC AGNCCANCCG CAATTGGCA CAATGTCGNC    540

GAACCCCCTA GGGGGANTNA TNCAAANCCC CAGGATTGTC CNCNCANGAA ATCCCNCANC   600

CCCNCCCTAC CCNNCTTTGG GACNGTGACC AANTCCCGGA GTNCCAGTCC GGCCNGNCTC   660

CCCCACCGGT NNCCNTGGGG GGGTGAANCT CNGNNTCANC CNGNCGAGGN NTCGNAAGGA   720

ACCGGNCCTN GGNCGAANNG ANCNNTCNGA AGNGCCNCNT CGTATAACCC CCCCTCNCCA   780
```

```
                                   -continued

NCCNACNGNT AGNTCCCCCC CNGGGTNCGG AANGG                                 815

(2) INFORMATION FOR SEQ ID NO:25:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CCGAGATGTC TCGCTCCGTG GCCTTAGCTG TGCTCGCGCT ACTCTCTCTT TCTGGCCTGG        60

AGGCTATCCA GCGTACTCCA AAGATTCAGG TTTACTCACG TCATCCAGCA GAGAATGGAA       120

AGTCAAATTT CCTGAATTGC TATGTGTCTG GGTTTCATCC ATCCGACATT GAANTTGACT       180

TACTGAAGAA TGGANAGAGA ATTGAAAAAG TGGAGCATTC AGACTTGTCT TTCAGCAAGG       240

ACTGGTCTTT CTATCTCNTG TACTACACTG AATTCACCCC CACTGAAAAA GATGAGTATG       300

CCTGCCGTGT GAACCATGTG ACTTTGTCAC AGCCCAAGAT AGTTAAGTGG GATCGAGACA       360

TGTAAGCAGN CNNCATGGAA GTTTGAAGAT GCCGCATTTG GATTGGATGA ATTCCAAATT       420

CTGCTTGCTT GCNTTTTAAT ANTGATATGC NTATACACCC TACCCTTTAT GNCCCCAAAT       480

TGTAGGGGTT ACATNANTGT TCNCNTNGGA CATGATCTTC CTTTATAANT CCNCCNTTCG       540

AATTGCCCGT CNCCCNGTTN NGAATGTTTC CNNAACCACG GTTGGCTCCC CCAGGTCNCC       600

TCTTACGGAA GGGCCTGGGC CNCTTTNCAA GGTTGGGGGA ACCNAAAATT TCNCTTNTGC       660

CCNCCCNCCA CNNTCTTGNG NNCNCANTTT GGAACCCTTC CNATTCCCCT TGGCCTCNNA       720

NCCTTNNCTA ANAAAACTTN AAANCGTNGC NAAANNTTTN ACTTCCCCCC TTACC           775

(2) INFORMATION FOR SEQ ID NO:26:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

ANATTANTAC AGTGTAATCT TTTCCCAGAG GTGTGTANAG GGAACGGGGC CTAGAGGCAT        60

CCCANAGATA NCTTATANCA ACAGTGCTTT GACCAAGAGC TGCTGGGCAC ATTTCCTGCA       120

GAAAAGGTGG CGGTCCCCAT CACTCCTCCT CTCCCATAGC CATCCCAGAG GGGTGAGTAG       180

CCATCANGCC TTCGGTGGGA GGGAGTCANG GAAACAACAN ACCACAGAGC ANACAGACCA       240

NTGATGACCA TGGGCGGGAG CGAGCCTCTT CCCTGNACCG GGGTGGCANA NGANAGCCTA       300

NCTGAGGGGT CACACTATAA ACGTTAACGA CCNAGATNAN CACCTGCTTC AAGTGCACCC       360

TTCCTACCTG ACNACCAGNG ACCNNNAACT GCNGCCTGGG GACAGCNCTG GGANCAGCTA       420

ACNNAGCACT CACCTGCCCC CCCATGGCCG TNCGCNTCCC TGGTCCTGNC AAGGGAAGCT       480

CCCTGTTGGA ATTNCGGGGA NACCAAGGGA NCCCCTCCT CCANCTGTGA AGGAAAAANN        540

GATGGAATTT TNCCCTTCCG GCCNNTCCCC TCTTCCTTTA CACGCCCCT NNTACTCNTC        600

TCCCTCTNTT NTCCTGNCNC ACTTTTNACC CCNNNATTTC CCTTNATTGA TCGGANNCTN      660

GANATTCCAC TNNCGCCTNC CNTCNATCNG NAANACNAAA NACTNTCTNA CCCNGGGGAT      720

GGGNNCCTCG NTCATCCTCT CTTTTTCNCT ACCNCCNNTT CTTTGCCTCT CCTTNGATCA      780
```

```
TCCAACCNTC GNTGGCCNTN CCCCCCCNNN TCCTTTNCCC                         820

(2) INFORMATION FOR SEQ ID NO:27:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TCTGGGTGAT GGCCTCTTCC TCCTCAGGGA CCTCTGACTG CTCTGGGCCA AAGAATCTCT    60

TGTTTCTTCT CCGAGCCCCA GGCAGCGGTG ATTCAGCCCT GCCCAACCTG ATTCTGATGA   120

CTGCGGATGC TGTGACGGAC CCAAGGGGCA AATAGGGTCC CAGGGTCCAG GGAGGGGCGC   180

CTGCTGAGCA CTTCCGCCCC TCACCCTGCC CAGCCCCTGC CATGAGCTCT GGGCTGGGTC   240

TCCGCCTCCA GGGTTCTGCT CTTCCANGCA NGCCANCAAG TGGCGCTGGG CCACACTGGC   300

TTCTTCCTGC CCCNTCCCTG GCTCTGANTC TCTGTCTTCC TGTCCTGTGC ANGCNCCTTG   360

GATCTCAGTT TCCCTCNCTC ANNGAACTCT GTTTCTGANN TCTTCANTTA ACTNTGANTT   420

TATNACCNAN TGGNCTGTNC TGTCNNACTT TAATGGGCCN GACCGGCTAA TCCCTCCCTC   480

NCTCCCTTCC ANTTCNNNNA ACCNGCTTNC CNTCNTCTCC CCNTANCCCG CCNGGGAANC   540

CTCCTTTGCC CTNACCANGG GCCNNNACCG CCCNTNNCTN GGGGGGCNNG GTNNCTNCNC   600

CTGNTNNCCC CNCTCNCNNT TNCCTCGTCC CNNCNNCGCN NNGCANNTTC NCNGTCCCNN   660

TNNCTCTTCN NGTNTCGNAA NGNTCNCNTN TNNNNNGNCN NGNTNNTNCN TCCCTCTCNC   720

CNNNTGNANG TNNTTNNNNC NCNGNNCCCC NNNNCNNNNN NGGNNNTNNN TCTNCNCNGC   780

CCCNNCCCCC NGNATTAAGG CCTCCNNTCT CCGGCCNC                          818

(2) INFORMATION FOR SEQ ID NO:28:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

AGGAAGGGCG GAGGGATATT GTANGGGATT GAGGGATAGG AGNATAANGG GGGAGGTGTG    60

TCCCAACATG ANGGTGNNGT TCTCTTTTGA ANGAGGGTTG NGTTTTTANN CCNGGTGGGT   120

GATTNAACCC CATTGTATGG AGNNAAAGGN TTTNAGGGAT TTTTCGGCTC TTATCAGTAT   180

NTANATTCCT GTNAATCGGA AAATNATNTT TCNNCNGGAA AATNTTGCTC CCATCCGNAA   240

ATTNCTCCCG GGTAGTGCAT NTTNGGGGGN CNGCCANGTT TCCCAGGCTG CTANAATCGT   300

ACTAAAGNTT NAAGTGGGAN TNCAAATGAA AACCTNNCAC AGAGNATCCN TACCCGACTG   360

TNNNTTNCCT TCGCCCTNTG ACTCTGCNNG AGCCCAATAC CCNNGNGNAT GTCNCCCNGN   420

NNNGCGNCNC TGAAANNNNC TCGNNGCTNN GANCATCANG GGGTTTCGCA TCAAAAGCNN   480

CGTTTCNCAT NAAGGCACTT TNGCCTCATC CAACCNCTNG CCCTCNNCCA TTTNGCCGTC   540

NGGTTCNCCT ACGCTNNNTG CNCCTNNNNTN GANATTTTNC CCGCCTNGGG NAANCCTCCT   600

GNAATGGGTA GGGNCTTNTC TTTTNACCNN GNGGTNTACT AATCNNCTNC ACGCNTNCTT   660
```

| | |
|---|---|
| TCTCNACCCC CCCCCTTTTT CAATCCCANC GGCNAATGGG GTCTCCCCNN CGANGGGGGG | 720 |
| NNNCCCANNC C | 731 |

(2) INFORMATION FOR SEQ ID NO:29:

(i) SEQUENCE CHARACTERISTICS:
  (A) LENGTH: 822 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:29:

| | |
|---|---|
| ACTAGTCCAG TGTGGTGGAA TTCCATTGTG TTGGGGNCNC TTCTATGANT ANTNTTAGAT | 60 |
| CGCTCANACC TCACANCCTC CCNACNANGC CTATAANGAA NANNAATAGA NCTGTNCNNT | 120 |
| ATNTNTACNC TCATANNCCT CNNNACCCAC TCCCTCTTAA CCCNTACTGT GCCTATNGCN | 180 |
| TNNCTANTCT NTGCCGCCTN CNANCCACCN GTGGGCCNAC CNCNNGNATT CTCNATCTCC | 240 |
| TCNCCATNTN GCCTANANTA NGTNCATACC CTATACCTAC NCCAATGCTA NNNCTAANCN | 300 |
| TCCATNANTT ANNNTAACTA CCACTGACNT NGACTTTCNC ATNANCTCCT AATTTGAATC | 360 |
| TACTCTGACT CCCACNGCCT ANNNATTAGC ANCNTCCCCC NACNATNTCT CAACCAAATC | 420 |
| NTCAACAACC TATCTANCTG TTCNCCAACC NTTNCCTCCG ATCCCCNNAC AACCCCCCTC | 480 |
| CCAAATACCC NCCACCTGAC NCCTAACCCN CACCATCCCG GCAAGCCNAN GGNCATTTAN | 540 |
| CCACTGGAAT CACNATNGGA NAAAAAAAAC CCNAACTCTC TANCNCNNAT CTCCCTAANA | 600 |
| AATNCTCCTN NAATTTACTN NCANTNCCAT CAANCCCACN TGAAACNNAA CCCCTGTTTT | 660 |
| TANATCCCTT CTTTCGAAAA CCNACCCTTT ANNNCCCAAC CTTTNGGGCC CCCCCNCTNC | 720 |
| CCNAATGAAG GNCNCCCAAT CNANGAAACG NCCNTGAAAA ANCNAGGCNA ANANNNTCCG | 780 |
| CANATCCTAT CCCTTANTTN GGGGNCCCTT NCCCNGGGCC CC | 822 |

(2) INFORMATION FOR SEQ ID NO:30:

(i) SEQUENCE CHARACTERISTICS:
  (A) LENGTH: 787 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:30:

| | |
|---|---|
| CGGCCGCCTG CTCTGGCACA TGCCTCCTGA ATGGCATCAA AAGTGATGGA CTGCCCATTG | 60 |
| CTAGAGAAGA CCTTCTCTCC TACTGTCATT ATGGAGCCCT GCAGACTGAG GGCTCCCCTT | 120 |
| GTCTGCAGGA TTTGATGTCT GAAGTCGTGG AGTGTGGCTT GGAGCTCCTC ATCTACATNA | 180 |
| GCTGGAAGCC CTGGAGGGCC TCTCTCGCCA GCCTCCCCCT TCTCTCCACG CTCTCCANGG | 240 |
| ACACCAGGGG CTCCAGGCAG CCCATTATTC CCAGNANGAC ATGGTGTTTC TCCACGCGGA | 300 |
| CCCATGGGGC CTGNAAGGCC AGGGTCTCCT TTGACACCAT CTCTCCCGTC CTGCCTGGCA | 360 |
| GGCCGTGGGA TCCACTANTT CTANAACGGN CGCCACCNCG GTGGGAGCTC CAGCTTTTGT | 420 |
| TCCCNTTAAT GAAGGTTAAT TGCNCGCTTG GCGTAATCAT NGGTCANAAC TNTTTCCTGT | 480 |
| GTGAAATTGT TTNTCCCCTC NCNATTCCNC NCNACATACN AACCCGGAAN CATAAAGTGT | 540 |
| TAAAGCCTGG GGGTNGCCTN NNGAATNAAC TNAACTCAAT TAATTGCGTT GGCTCATGGC | 600 |
| CCGCTTTCCN TTCNGGAAAA CTGTCNTCCC CTGCNTTNNT GAATCGGCCA CCCCCCNGGG | 660 |

```
AAAAGCGGTT TGCNTTTTNG GGGGNTCCTT CCNCTTCCCC CCTCNCTAAN CCCTNCGCCT        720

CGGTCGTTNC NGGTNGCGGG GAANGGGNAT NNNCTCCCNC NAAGGGGGNG AGNNNGNTAT        780

CCCCAAA                                                                 787

(2) INFORMATION FOR SEQ ID NO:31:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

TTTTTTTTTT TTTTTTTGGC GATGCTACTG TTTAATTGCA GGAGGTGGGG GTGTGTGTAC         60

CATGTACCAG GGCTATTAGA AGCAAGAAGG AAGGAGGGAG GGCAGAGCGC CCTGCTGAGC        120

AACAAAGGAC TCCTGCAGCC TTCTCTGTCT GTCTCTTGGC GCAGGCACAT GGGGAGGCCT        180

CCCGCAGGGT GGGGGCCACC AGTCCAGGGG TGGGAGCACT ACANGGGGTG GGAGTGGGTG        240

GTGGCTGGTN CNAATGGCCT GNCACANATC CCTACGATTC TTGACACCTG GATTTCACCA        300

GGGGACCTTC TGTTCTCCCA NGGNAACTTC NTNNATCTCN AAAGAACACA ACTGTTTCTT        360

CNGCANTTCT GGCTGTTCAT GGAAAGCACA GGTGTCCNAT TTNGGCTGGG ACTTGGTACA        420

TATGGTTCCG GCCCACCTCT CCCNTCNAAN AAGTAATTCA CCCCCCCCCN CCNTCTNTTG        480

CCTGGGCCCT TAANTACCCA CACCGGAACT CANTTANTTA TTCATCTTNG GNTGGGCTTG        540

NTNATCNCCN CCTGAANGCG CCAAGTTGAA AGGCCACGCC GTNCCCNCTC CCCATAGNAN        600

NTTTTNNCNT CANCTAATGC CCCCCCNGGC AACNATCCAA TCCCCCCCCN TGGGGCCCC        660

AGCCCANGGC CCCCGNCTCG GGNNNCCNGN CNCGNANTCC CCAGGNTCTC CCANTCNGNC        720

CCNNNGCNCC CCCCGCACGCA GAACANAAGG NTNGAGCCNC CGCANNNNNN NGGTNNCNAC        780

CTCGCCCCCC CCNNCGNNG                                                    799

(2) INFORMATION FOR SEQ ID NO:32:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

TTTTTTTTTT TTTTTTTTTT TTTTTTTTTT TTTTTTTTTT TTTTTTTTTT TTTTTTTTTT         60

TTTTNCCNAG GGCAGGTTTA TTGACAACCT CNCGGACAC AANCAGGCTG GGACAGGAC          120

GGCAACAGGC TCCGGCGGCG GCGGCGGCGG CCCTACCTGC GGTACCAAAT NTGCAGCCTC        180

CGCTCCCGCT TGATNTTCCT CTGCAGCTGC AGGATGCCNT AAAACAGGGC CTCGGCCNTN        240

GGTGGGCACC CTGGGATTTN AATTTCCACG GCACAATGC GGTCGCANCC CCTCACCACC        300

NATTAGGAAT AGTGGTNTTA CCCNCCNCCG TTGGCNCACT CCCCNTGGAA ACCACTTNTC        360

GCGGCTCCGG CATCTGGTCT TAAACCTTGC AAACNCTGGG GCCCTCTTTT TGGTTANTNT        420

NCCNGCCACA ATCATNACTC AGACTGGCNC GGGCTGGCCC CAAAAAANCN CCCCAAAACC       480

GGNCCATGTC TTNNCGGGGT TGCTGCNATN TNCATCACCT CCCGGGCNCA NCAGGNCAAC       540
```

| | |
|---|---|
| CCAAAAGTTC TTGNGGCCCN CAAAAAANCT CCGGGGGGNC CCAGTTTCAA CAAAGTCATC | 600 |
| CCCCTTGGCC CCCAAATCCT CCCCCCGNTT NCTGGGTTTG GGAACCCACG CCTCTNNCTT | 660 |
| TGGNNGGCAA GNTGGNTCCC CCTTCGGGCC CCCGGTGGGC CCNNCTCTAA NGAAAACNCC | 720 |
| NTCCTNNNCA CCATCCCCCC NNGNNACGNC TANCAANGNA TCCCTTTTTT TANAAACGGG | 780 |
| CCCCCCNCG | 789 |

(2) INFORMATION FOR SEQ ID NO:33:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

| | |
|---|---|
| GACAGAACAT GTTGGATGGT GGAGCACCTT TCTATACGAC TTACAGGACA GCAGATGGGG | 60 |
| AATTCATGGC TGTTGGAGCA ATANAACCCC AGTTCTACGA GCTGCTGATC AAAGGACTTG | 120 |
| GACTAAAGTC TGATGAACTT CCCAATCAGA TGAGCATGGA TGATTGGCCA GAAATGAANA | 180 |
| AGAAGTTTGC AGATGTATTT GCAAAGAAGA CGAAGGCAGA GTGGTGTCAA ATCTTTGACG | 240 |
| GCACAGATGC CTGTGTGACT CCGGTTCTGA CTTTTGAGGA GGTTGTTCAT CATGATCACA | 300 |
| ACAANGAACG GGGCTCGTTT ATCACCANTG AGGAGCAGGA CGTGAGCCCC CGCCCTGCAC | 360 |
| CTCTGCTGTT AAACACCCCA GCCATCCCTT CTTTCAAAAG GGATCCACTA CTTCTAGAGC | 420 |
| GGNCGCCACC GCGGTGGAGC TCCAGCTTTT GTTCCCTTTA GTGAGGGTTA ATTGCGCGCT | 480 |
| TGGCGTAATC ATGGTCATAN CTGTTTCCTG TGTGAAATTG TTATCCGCTC ACAATTCCAC | 540 |
| ACAACATACG ANCCGGAAGC ATNAAATTTT AAAGCCTGGN GGTNGCCTAA TGANTGAACT | 600 |
| NACTCACATT AATTGGCTTT GCGCTCACTG CCCGCTTTCC AGTCCGGAAA ACCTGTCCTT | 660 |
| GCCAGCTGCC NTTAATGAAT CNGGCCACCC CCCGGGGAAA AGGCNGTTTG CTTNTTGGGG | 720 |
| CGCNCTTCCC GCTTTCTCGC TTCCTGAANT CCTTCCCCCC GGTCTTTCGG CTTGCGGCNA | 780 |
| ACGGTATCNA CCT | 793 |

(2) INFORMATION FOR SEQ ID NO:34:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

| | |
|---|---|
| GCCGCGACCG GCATGTACGA GCAACTCAAG GGCGAGTGGA ACCGTAAAAG CCCCAATCTT | 60 |
| ANCAAGTGCG GGGAANAGCT GGGTCGACTC AAGCTAGTTC TTCTGGAGCT CAACTTCTTG | 120 |
| CCAACCACAG GGACCAAGCT GACCAAACAG CAGCTAATTC TGGCCCGTGA CATACTGGAG | 180 |
| ATCGGGGCCC AATGGAGCAT CCTACGCAAN GACATCCCCT CCTTCGAGCG CTACATGGCC | 240 |
| CAGCTCAAAT GCTACTACTT TGATTACAAN GAGCAGCTCC CCGAGTCAGC CTATATGCAC | 300 |
| CAGCTCTTGG GCCTCAACCT CCTCTTCCTG CTGTCCCAGA ACCGGGTGGC TGANTNCCAC | 360 |
| ACGGANTTGG ANCGGCTGCC TGCCCAANGA CATACANACC AATGTCTACA TCNACCACCA | 420 |
| GTGTCCTGGA GCAATACTGA TGGANGGCAG CTACCNCAAA GTNTTCCTGG CCNAGGGTAA | 480 |

```
CATCCCCCGC CGAGAGCTAC ACCTTCTTCA TTGACATCCT GCTCGACACT ATCAGGGATG      540

AAAATCGCNG GGTTGCTCCA GAAAGGCTNC AANAANATCC TTTTCNCTGA AGGCCCCCGG      600

ATNCNCTAGT NCTAGAATCG GCCCGCCATC GCGGTGGANC CTCCAACCTT TCGTTNCCCT      660

TTACTGAGGG TTNATTGCCG CCCTTGGCGT TATCATGGTC ACNCCNGTTN CCTGTGTTGA      720

AATTNTTAAC CCCCCACAAT TCCACGCCNA CATTNG                                756

(2) INFORMATION FOR SEQ ID NO:35:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GGGGATCTCT ANATCNACCT GNATGCATGG TTGTCGGTGT GGTCGCTGTC GATGAANATG       60

AACAGGATCT TGCCCTTGAA GCTCTCGGCT GCTGTNTTTA AGTTGCTCAG TCTGCCGTCA      120

TAGTCAGACA CNCTCTTGGG CAAAAAAACAN CAGGATNTGA GTCTTGATTT CACCTCCAAT    180

AATCTTCNGG GCTGTCTGCT CGGTGAACTC GATGACNANG GGCAGCTGGT TGTGTNTGAT      240

AAANTCCANC ANGTTCTCCT TGGTGACCTC CCCTTCAAAG TTGTTCCGGC CTTCATCAAA     300

CTTCTNNAAN ANGANNANCC CANCTTTGTC GAGCTGGNAT TTGGANAACA CGTCACTGTT     360

GGAAACTGAT CCCAAATGGT ATGTCATCCA TCGCCTCTGC TGCCTGCAAA AAACTTGCTT    420

GGCNCAAATC CGACTCCCCN TCCTTGAAAG AAGCCNATCA CACCCCCCTC CCTGGACTCC     480

NNCAANGACT CTNCCGCTNC CCCNTCCNNG CAGGGTTGGT GGCANNCCGG GCCCNTGCGC     540

TTCTTCAGCC AGTTCACNAT NTTCATCAGC CCCTCTGCCA GCTGTTNTAT TCCTTGGGGG     600

GGAANCCGTC TCTCCCTTCC TGAANNAACT TTGACCGTNG GAATAGCCGC GCNTCNCCNT    660

ACNTNCTGGG CCGGGTTCAA ANTCCCTCCN TTGNCNNTCN CCTCGGGCCA TTCTGGATTT    720

NCCNAACTTT TTCCTTCCCC CNCCCCNCGG NGTTTGGNTT TTTCATNGGG CCCCAACTCT    780

GCTNTTGGCC ANTCCCCTGG GGGCNTNTAN CNCCCCCTNT GGTCCCNTNG GGCC           834

(2) INFORMATION FOR SEQ ID NO:36:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

CGGNCGCTTT CCNGCCGCGC CCCGTTTCCA TGACNAAGGC TCCCTTCANG TTAAATACNN       60

CCTAGNAAAC ATTAATGGGT TGCTCTACTA ATACATCATA CNAACCAGTA AGCCTGCCCA      120

NAACGCCAAC TCAGGCCATT CCTACCAAAG GAAGAAAGGC TGGTCTCTCC ACCCCCTGTA      180

GGAAAGGCCT GCCTTGTAAG ACACCACAAT NCGGCTGAAT CTNAAGTCTT GTGTTTTACT    240

AATGGAAAAA AAAAATAAAC AANAGGTTTT GTTCTCATGG CTGCCCACCG CAGCCTGGCA     300

CTAAAACANC CCAGCGCTCA CTTCTGCTTG GANAAATATT CTTTGCTCTT TTGGACATCA    360

GGCTTGATGG TATCACTGCC ACNTTCCAC CCAGCTGGGC NCCCTTCCCC CATNTTTGTC     420
```

| | |
|---|---|
| ANTGANCTGG AAGGCCTGAA NCTTAGTCTC CAAAAGTCTC NGCCCACAAG ACCGGCCACC | 480 |
| AGGGGANGTC NTTTNCAGTG GATCTGCCAA ANANTACCCN TATCATCNNT GAATAAAAAG | 540 |
| GCCCCTGAAC GANATGCTTC CANCANCCTT TAAGACCCAT AATCCTNGAA CCATGGTGCC | 600 |
| CTTCCGGTCT GATCCNAAAG GAATGTTCCT GGGTCCCANT CCCTCCTTTG TTNCTTACGT | 660 |
| TGTNTTGGAC CCNTGCTNGN ATNACCCAAN TGANATCCCC NGAAGCACCC TNCCCCTGGC | 720 |
| ATTTGANTTT CNTAAATTCT CTGCCCTACN NCTGAAAGCA CNATTCCCTN GGCNCCNAAN | 780 |
| GGNGAACTCA AGAAGGTCTN NGAAAAACCA CNCN | 814 |

(2) INFORMATION FOR SEQ ID NO:37:

(i) SEQUENCE CHARACTERISTICS:
        (A) LENGTH: 760 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

| | |
|---|---|
| GCATGCTGCT CTTCCTCAAA GTTGTTCTTG TTGCCATAAC AACCACCATA GGTAAAGCGG | 60 |
| GCGCAGTGTT CGCTGAAGGG GTTGTAGTAC CAGCGCGGGA TGCTCTCCTT GCAGAGTCCT | 120 |
| GTGTCTGGCA GGTCCACGCA ATGCCCTTTG TCACTGGGGA AATGGATGCG CTGGAGCTCG | 180 |
| TCNAANCCAC TCGTGTATTT TTCACANGCA GCCTCCTCCG AAGCNTCCGG GCAGTTGGGG | 240 |
| GTGTCGTCAC ACTCCACTAA ACTGTCGATN CANCAGCCCA TTGCTGCAGC GGAACTGGGT | 300 |
| GGGCTGACAG GTGCCAGAAC ACACTGGATN GGCCTTTCCA TGGAAGGGCC TGGGGGAAAT | 360 |
| CNCCTNANCC CAAACTGCCT CTCAAAGGCC ACCTTGCACA CCCCGACAGG CTAGAAATGC | 420 |
| ACTCTTCTTC CCAAAGGTAG TTGTTCTTGT TGCCCAAGCA NCCTCCANCA AACCAAAANC | 480 |
| TTGCAAAATC TGCTCCGTGG GGGTCATNNN TACCANGGTT GGGGAAANAA ACCCGGCNGN | 540 |
| GANCCNCCTT GTTTGAATGC NAAGGNAATA ATCCTCCTGT CTTGCTTGGG TGGAANAGCA | 600 |
| CAATTGAACT GTTAACNTTG GGCCGNGTTC CNCTNGGGTG GTCTGAAACT AATCACCGTC | 660 |
| ACTGGAAAAA GGTANGTGCC TTCCTTGAAT TCCCAAANTT CCCCTNGNTT TGGGTNNTTT | 720 |
| CTCCTCTNCC CTAAAAATCG TNTTCCCCCC CCNTANGGCG | 760 |

(2) INFORMATION FOR SEQ ID NO:38:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

| | |
|---|---|
| TTTTTTTTTT TTTTTTTTTT TTTTTTTTTT TTTTTAAAAA CCCCCTCCAT TGAATGAAAA | 60 |
| CTTCCNAAAT TGTCCAACCC CCTCNNCCAA ATNNCCATTT CCGGGGGGGG GTTCCAAACC | 120 |
| CAAATTAATT TTGGANTTTA AATTAAATNT TNATTNGGGG AANAANCCAA ATGTNAAGAA | 180 |
| AATTTAACCC ATTATNAACT TAAATNCCTN GAAACCCNTG GNTTCCAAAA ATTTTTAACC | 240 |
| CTTAAATCCC TCCGAAATTG NTAANGGAAA ACCAAATTCN CCTAAGGCTN TTTGAAGGTT | 300 |
| NGATTTAAAC CCCCTTNANT TNTTTTNACC CNNGNCTNAA NTATTTNGNT TCCGGTGTTT | 360 |
| TCCTNTTAAN CNTNGGTAAC TCCCGNTAAT GAANNNCCCT AANCCAATTA AACCGAATTT | 420 |

```
TTTTTGAATT GGAAATTCCN NGGGAATTNA CCGGGGTTTT TCCCNTTTGG GGGCCATNCC      480

CCCNCTTTCG GGGTTTGGGN NTAGGTTGAA TTTTTNNANG NCCCAAAAAA NCCCCCAANA      540

AAAAAACTCC CAAGNNTTAA TTNGAATNTC CCCCTTCCCA GGCCTTTTGG GAAAGGNGGG      600

TTTNTGGGGG CCNGGGANTT CNTTCCCCCN TTNCCNCCCC CCCCCCNGGT AAANGGTTAT      660

NGNNTTTGGT TTTTGGGCCC CTTNANGGAC CTTCCGGATN GAAATTAAAT CCCCGGGNCG      720

GCCG                                                                  724

(2) INFORMATION FOR SEQ ID NO:39:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TTTTTTTTTT TTTTCTTTG CTCACATTTA ATTTTTATTT TGATTTTTTT TAATGCTGCA        60

CAACACAATA TTTATTTCAT TTGTTTCTTT TATTTCATTT TATTTGTTTG CTGCTGCTGT      120

TTTATTTATT TTTACTGAAA GTGAGAGGGA ACTTTTGTGG CCTTTTTTCC TTTTTCTGTA      180

GGCCGCCTTA AGCTTTCTAA ATTTGGAACA TCTAAGCAAG CTGAANGGAA AAGGGGGTTT      240

CGCAAAATCA CTCGGGGGAA NGGAAAGGTT GCTTTGTTAA TCATGCCCTA TGGTGGGTGA      300

TTAACTGCTT GTACAATTAC NTTTCACTTT TAATTAATTG TGCTNAANGC TTTAATTANA      360

CTTGGGGGTT CCCTCCCCAN ACCAACCCCN CTGACAAAAA GTGCCNGCCC TCAAATNATG      420

TCCCGGCNNT CNTTGAAACA CACNGCNGAA NGTTCTCATT NTCCCCNCNC CAGGTNAAAA      480

TGAAGGGTTA CCATNTTTAA CNCCACCTCC ACNTGGCNNN GCCTGAATCC TCNAAAANCN      540

CCCTCAANCN AATTNCTNNG CCCCGGTCNC GCNTNNGTCC CNCCCGGGCT CCGGGAANTN      600

CACCCCCNGA ANNCNNTNNC NAACNAAATT CCGAAAATAT TCCCNNTCNC TCAATTCCCC      660

CNNAGACTNT CCTCNNCNAN CNCAATTTTC TTTTNNTCAC GAACNCGNNC CNNAAAATGN      720

NNNNCNCCTC CNCTNGTCCN NAATCNCCAN C                                    751

(2) INFORMATION FOR SEQ ID NO:40:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GTGGTATTTT CTGTAAGATC AGGTGTTCCT CCCTCGTAGG TTTAGAGGAA ACACCCTCAT       60

AGATGAAAAC CCCCCCGAGA CAGCAGCACT GCAACTGCCA AGCAGCCGGG GTAGGAGGGG      120

CGCCCTATGC ACAGCTGGGC CCTTGAGACA GCAGGGCTTC GATGTCAGGC TCGATGTCAA      180

TGGTCTGGAA GCGGCGGCTG TACCTGCGTA GGGGCACACC GTCAGGGCCC ACCAGGAACT      240

TCTCAAAGTT CCAGGCAACN TCGTTGCGAC ACACCGGAGA CCAGGTGATN AGCTTGGGGT      300

CGGTCATAAN CGCGGTGGCG TCGTCGCTGG GAGCTGGCAG GGCCTCCCGC AGGAAGGCNA      360

ATAAAAGGTG CGCCCCCGCA CCGTTCANCT CGCACTTCTC NAANACCATG ANGTTGGGCT      420
```

```
CNAACCCACC ACCANNCCGG ACTTCCTTGA NGGAATTCCC AAATCTCTTC GNTCTTGGGC      480

TTCTNCTGAT GCCCTANCTG GTTGCCCNGN ATGCCAANCA NCCCCAANCC CCGGGGTCCT      540

AAANCACCCN CCTCCTCNTT TCATCTGGGT TNTTNTCCCC GGACCNTGGT TCCTCTCAAG      600

GGANCCCATA TCTCNACCAN TACTCACCNT NCCCCCCCNT GNNACCCANC CTTCTANNGN      660

TTCCCNCCCG NCCTCTGGCC CNTCAAANAN GCTTNCACNA CCTGGGTCTG CCTTCCCCCC      720

TNCCCTATCT GNACCCCNCN TTTGTCTCAN TNT                                  753

(2) INFORMATION FOR SEQ ID NO:41:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:41:

ACTATATCCA TCACAACAGA CATGCTTCAT CCCATAGACT TCTTGACATA GCTTCAAATG       60

AGTGAACCCA TCCTTGATTT ATATACATAT ATGTTCTCAG TATTTTGGGA GCCTTTCCAC      120

TTCTTTAAAC CTTGTTCATT ATGAACACTG AAAATAGGAA TTTGTGAAGA GTTAAAAAGT     180

TATAGCTTGT TTACGTAGTA AGTTTTTGAA GTCTACATTC AATCCAGACA CTTAGTTGAG      240

TGTTAAACTG TGATTTTTAA AAAATATCAT TTGAGAATAT TCTTTCAGAG GTATTTTCAT      300

TTTTACTTTT TGATTAATTG TGTTTTATAT ATTAGGGTAG T                          341

(2) INFORMATION FOR SEQ ID NO:42:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:42:

ACTTACTGAA TTTAGTTCTG TGCTCTTCCT TATTTAGTGT TGTATCATAA ATACTTTGAT       60

GTTTCAAACA TTCTAAATAA ATAATTTTCA GTGGCTTCAT A                          101

(2) INFORMATION FOR SEQ ID NO:43:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo spiens (xi) SEQUENCE DESCRIPTION: SEQ ID NO:43:

ACATCTTTGT TACAGTCTAA GATGTGTTCT TAAATCACCA TTCCTTCCTG GTCCTCACCC       60

TCCAGGGTGG TCTCACACTG TAATTAGAGC TATTGAGGAG TCTTTACAGC AAATTAAGAT      120
```

```
TCAGATGCCT TGCTAAGTCT AGAGTTCTAG AGTTATGTTT CAGAAAGTCT AAGAAACCCA    180

CCTCTTGAGA GGTCAGTAAA GAGGACTTAA TATTTCATAT CTACAAAATG ACCACAGGAT    240

TGGATACAGA ACGAGAGTTA TCCTGGATAA CTCAGAGCTG AGTACCTGCC CGGGGGCCGC    300

TCGAA                                                                305
```

(2) INFORMATION FOR SEQ ID NO:44:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:44:

```
ACATAAATAT CAGAGAAAAG TAGTCTTTGA AATATTTACG TCCAGGAGTT CTTTGTTTCT     60

GATTATTTGG TGTGTGTTTT GGTTTGTGTC CAAAGTATTG GCAGCTTCAG TTTTCATTTT    120

CTCTCCATCC TCGGGCATTC TTCCCAAATT TATATACCAG TCTTCGTCCA TCCACACGCT    180

CCAGAATTTC TCTTTTGTAG TAATATCTCA TAGCTCGGCT GAGCTTTTCA TAGGTCATGC    240

TGCTGTTGTT CTTCTTTTTA CCCCATAGCT GAGCCACTGC CTCTGATTTC AAGAACCTGA    300

AGACGCCCTC AGATCGGTCT TCCCATTTTA TTAATCCTGG GTTCTTGTCT GGGTTCAAGA    360

GGATGTCGCG GATGAATTCC CATAAGTGAG TCCCTCTCGG GTTGTGCTTT TTGGTGTGGC    420

ACTTGGCAGG GGGGTCTTGC TCCTTTTTCA TATCAGGTGA CTCTGCAACA GGAAGGTGAC    480

TGGTGGTTGT CATGGAGATC TGAGCCCGGC AGAAAGTTTT GCTGTCCAAC AAATCTACTG    540

TGCTACCATA GTTGGTGTCA TATAAATAGT TCTNGTCTTT CCAGGTGTTC ATGATGGAAG    600

GCTCAGTTTG TTCAGTCTTG ACAATGACAT TGTGTGTGGA CTGGAACAGG TCACTACTGC    660

ACTGGCCGTT CCACTTCAGA TGCTGCAAGT TGCTGTAGAG GAGNTGCCCC GCCGTCCCTG    720

CCGCCCGGGT GAACTCCTGC AAACTCATGC TGCAAAGGTG CTCGCCGTTG ATGTCGAACT    780

CNTGGAAAGG GATACAATTG GCATCCAGCT GGTTGGTGTC CAGGAGGTGA TGGAGCCACT    840

CCCACACCTG GT                                                       852
```

(2) INFORMATION FOR SEQ ID NO:45:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:45:

```
ACAACAGACC CTTGCTCGCT AACGACCTCA TGCTCATCAA GTTGGACGAA TCCGTGTCCG     60

AGTCTGACAC CATCCGGAGC ATCAGCATTG CTTCGCAGTG CCCTACCGCG GGGAACTCTT    120

GCCTCGTTTC TGGCTGGGGT CTGCTGGCGA ACGGCAGAAT GCCTACCGTG CTGCAGTGCG    180

TGAACGTGTC GGTGGTGTCT GAGGAGGTCT GCAGTAAGCT CTATGACCCG CTGT          234
```

(2) INFORMATION FOR SEQ ID NO:46:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:46:

```
ACTTTTTATT TAAATGTTTA TAAGGCAGAT CTATGAGAAT GATAGAAAAC ATGGTGTGTA      60

ATTTGATAGC AATATTTTGG AGATTACAGA GTTTTAGTAA TTACCAATTA CACAGTTAAA     120

AAGAAGATAA TATATTCCAA GCANATACAA AATATCTAAT GAAAGATCAA GGCAGGAAAA     180

TGANTATAAC TAATTGACAA TGGAAAATCA ATTTTAATGT GAATTGCACA TTATCCTTTA     240

AAAGCTTTCA AAANAAANAA TTATTGCAGT CTANTTAATT CAAACAGTGT TAAATGGTAT     300

CAGGATAAAN AACTGAAGGG CANAAAGAAT TAATTTTCAC TTCATGTAAC NCACCCANAT     360

TTACAATGGC TTAAATGCAN GGAAAAAGCA GTGGAAGTAG GGAAGTANTC AAGGTCTTTC     420

TGGTCTCTAA TCTGCCTTAC TCTTTGGGTG TGGCTTTGAT CCTCTGGAGA CAGCTGCCAG     480

GGCTCCTGTT ATATCCACAA TCCCAGCAGC AAGATGAAGG GATGAAAAAG GACACATGCT     540

GCCTTCCTTT GAGGAGACTT CATCTCACTG GCCAACACTC AGTCACATGT                590
```

(2) INFORMATION FOR SEQ ID NO:47:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:47:

```
ACAAGGGGC ATAATGAAGG AGTGGGGANA GATTTTAAAG AAGGAAAAAA AACGAGGCCC       60

TGAACAGAAT TTTCCTGNAC AACGGGGCTT CAAAATAATT TTCTTGGGGA GGTTCAAGAC     120

GCTTCACTGC TTGAAACTTA AATGGATGTG GGACANAATT TTCTGTAATG ACCCTGAGGG     180

CATTACAGAC GGGACTCTGG GAGGAAGGAT AAACAGAAAG GGGACAAAGG CTAATCCCAA     240

AACATCAAAG AAAGGAAGGT GGCGTCATAC CTCCCAGCCT ACACAGTTCT CCAGGGCTCT     300

CCTCATCCCT GGAGGACGAC AGTGGAGGAA CAACTGACCA TGTCCCCAGG CTCCTGTGTG     360

CTGGCTCCTG GTCTTCAGCC CCCAGCTCTG GAAGCCCACC CTCTGCTGAT CCTGCGTGGC     420

CCACACTCCT TGAACACACA TCCCCAGGTT ATATTCCTGG ACATGGCTGA ACCTCCTATT     480

CCTACTTCCG AGATGCCTTG CTCCCTGCAG CCTGTCAAAA TCCCACTCAC CCTCCAAACC     540

ACGGCATGGG AAGCCTTTCT GACTTGCCTG ATTACTCCAG CATCTTGGAA CAATCCCTGA     600

TTCCCCACTC CTTAGAGGCA AGATAGGGTG GTTAAGAGTA GGGCTGGACC ACTTGGAGCC     660

AGGCTGCTGG CTTCAAATTN TGGCTCATTT ACGAGCTATG GGACCTTGGG CAAGTNATCT     720

TCACTTCTAT GGGCNTCATT TTGTTCTACC TGCAAAATGG GGGATAATAA TAGT           774
```

(2) INFORMATION FOR SEQ ID NO:48:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:48:

```
CANAAATTGA AATTTTATAA AAAGGCATTT TTCTCTTATA TCCATAAAAT GATATAATTT      60

TTGCAANTAT ANAAATGTGT CATAAATTAT AATGTTCCTT AATTACAGCT CAACGCAACT     120

TGGT                                                                 124
```

(2) INFORMATION FOR SEQ ID NO:49:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:49:

```
GCCGATGCTA CTATTTTATT GCAGGAGGTG GGGGTGTTTT TATTATTCTC TCAACAGCTT      60

TGTGGCTACA GGTGGTGTCT GACTGCATNA AAAANTTTTT TACGGGTGAT TGCAAAAATT     120

TTAGGGCACC CATATCCCAA GCANTGT                                        147
```

(2) INFORMATION FOR SEQ ID NO:50:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:50:

```
ACATTAAATT AATAAAAGGA CTGTTGGGGT TCTGCTAAAA CACATGGCTT GATATATTGC      60

ATGGTTTGAG GTTAGGAGGA GTTAGGCATA TGTTTTGGGA GAGGGGT                  107
```

(2) INFORMATION FOR SEQ ID NO:51:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:51:

| | |
|---|---|
| GTCCTAGGAA GTCTAGGGGA CACACGACTC TGGGGTCACG GGGCCGACAC ACTTGCACGG | 60 |
| CGGGAAGGAA AGGCAGAGAA GTGACACCGT CAGGGGGAAA TGACAGAAAG GAAAATCAAG | 120 |
| GCCTTGCAAG GTCAGAAAGG GGACTCAGGG CTTCCACCAC AGCCCTGCCC CACTTGGCCA | 180 |
| CCTCCCTTTT GGGACCAGCA ATGT | 204 |

(2) INFORMATION FOR SEQ ID NO:52:

(i) SEQUENCE CHARACTERISTICS:
        (A) LENGTH: 491 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:52:

| | |
|---|---|
| ACAAAGATAA CATTTATCTT ATAACAAAAA TTTGATAGTT TTAAAGGTTA GTATTGTGTA | 60 |
| GGGTATTTTC CAAAAGACTA AAGAGATAAC TCAGGTAAAA AGTTAGAAAT GTATAAAACA | 120 |
| CCATCAGACA GGTTTTTAAA AAACAACATA TTACAAAATT AGACAATCAT CCTTAAAAAA | 180 |
| AAAACTTCTT GTATCAATTT CTTTTGTTCA AAATGACTGA CTTAANTATT TTTAAATATT | 240 |
| TCANAAACAC TTCCTCAAAA ATTTTCAANA TGGTAGCTTT CANATGTNCC CTCAGTCCCA | 300 |
| ATGTTGCTCA GATAAATAAA TCTCGTGAGA ACTTACCACC CACCCACAAGC TTTCTGGGGC | 360 |
| ATGCAACAGT GTCTTTTCTT TNCTTTTTCT TTTTTTTTTT TTACAGGCAC AGAAACTCAT | 420 |
| CAATTTTATT TGGATAACAA AGGGTCTCCA AATTATATTG AAAAATAAAT CCAAGTTAAT | 480 |
| ATCACTCTTG T | 491 |

(2) INFORMATION FOR SEQ ID NO:53:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:53:

| | |
|---|---|
| ACATAATTTA GCAGGGCTAA TTACCATAAG ATGCTATTTA TTAANAGGTN TATGATCTGA | 60 |
| GTATTAACAG TTGCTGAAGT TTGGTATTTT TATGCAGCAT TTTCTTTTTG CTTTGATAAC | 120 |
| ACTACAGAAC CCTTAAGGAC ACTGAAAATT AGTAAGTAAA GTTCAGAAAC ATTAGCTGCT | 180 |
| CAATCAAATC TCTACATAAC ACTATAGTAA TTAAAACGTT AAAAAAAAGT GTTGAAATCT | 240 |
| GCACTAGTAT ANACCGCTCC TGTCAGGATA ANACTGCTTT GGAACAGAAA GGGAAAAANC | 300 |
| AGCTTTGANT TTCTTTGTGC TGATANGAGG AAAGGCTGAA TTACCTTGTT GCCTCTCCCT | 360 |
| AATGATTGGC AGGTCNGGTA AATNCCAAAA CATATTCCAA CTCAACACTT CTTTTCCNCG | 420 |
| TANCTTGANT CTGTGTATTC CAGGANCAGG CGGATGGAAT GGGCCAGCCC NCGGATGTTC | 480 |
| CANT | 484 |

(2) INFORMATION FOR SEQ ID NO:54:

(i) SEQUENCE CHARACTERISTICS:
    (A) LENGTH: 151 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:54:

```
ACTAAACCTC GTGCTTGTGA ACTCCATACA GAAAACGGTG CCATCCCTGA ACACGGCTGG      60

CCACTGGGTA TACTGCTGAC AACCGCAACA ACAAAAACAC AAATCCTTGG CACTGGCTAG     120

TCTATGTCCT CTCAAGTGCC TTTTTGTTTG T                                    151
```

(2) INFORMATION FOR SEQ ID NO:55:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:55:

```
ACCTGGCTTG TCTCCGGGTG GTTCCCGGCG CCCCCCACGG TCCCCAGAAC GGACACTTTC      60

GCCCTCCAGT GGATACTCGA GCCAAAGTGG T                                     91
```

(2) INFORMATION FOR SEQ ID NO:56:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:56:

```
GGCGGATGTG CGTTGGTTAT ATACAAATAT GTCATTTTAT GTAAGGGACT TGAGTATACT      60

TGGATTTTTG GTATCTGTGG GTTGGGGGGA CGGTCCAGGA ACCAATACCC CATGGATACC     120

AAGGGACAAC TGT                                                        133
```

(2) INFORMATION FOR SEQ ID NO:57:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:57:

```
ACTCTGGAGA ACCTGAGCCG CTGCTCCGCC TCTGGGATGA GGTGATGCAN GCNGTGGCGC      60
```

| GACTGGGAGC TGAGCCCTTC CCTTTGCGCC TGCCTCAGAG GATTGTTGCC GACNTGCANA | 120 |
| TCTCANTGGG CTGGATNCAT GCAGGGT | 147 |

(2) INFORMATION FOR SEQ ID NO:58:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:58:

| ACAGGGATAT AGGTTTNAAG TTATTGTNAT TGTAAAATAC ATTGAATTTT CTGTATACTC | 60 |
| TGATTACATA CATTTATCCT TTAAAAAAGA TGTAAATCTT AATTTTTATG CCATCTATTA | 120 |
| ATTTACCAAT GAGTTACCTT GTAAATGAGA AGTCATGATA GCACTGAATT TTAACTAGTT | 180 |
| TTGACTTCTA AGTTTGGT | 198 |

(2) INFORMATION FOR SEQ ID NO:59:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:59:

| ACAACAAATG GGTTGTGAGG AAGTCTTATC AGCAAAACTG GTGATGGCTA CTGAAAAGAT | 60 |
| CCATTGAAAA TTATCATTAA TGATTTTAAA TGACAAGTTA TCAAAAACTC ACTCAATTTT | 120 |
| CACCTGTGCT AGCTTGCTAA ATGGGAGTT AACTCTAGAG CAAATATAGT ATCTTCTGAA | 180 |
| TACAGTCAAT AAATGACAAA GCCAGGGCCT ACAGGTGGTT TCCAGACTTT CCAGACCCAG | 240 |
| CAGAAGGAAT CTATTTTATC ACATGGATCT CCGTCTGTGC TCAAAATACC TAATGATATT | 300 |
| TTTCGTCTTT ATTGGACTTC TTTGAAGAGT | 330 |

(2) INFORMATION FOR SEQ ID NO:60:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:60:

| ACCGTGGGTG CCTTCTACAT TCCTGACGGC TCCTTCACCA ACATCTGGTT CTACTTCGGC | 60 |
| GTCGTGGGCT CCTTCCTCTT CATCCTCATC CAGCTGGTGC TGCTCATCGA CTTTGCGCAC | 120 |
| TCCTGGAACC AGCGGTGGCT GGGCAAGGCC GAGGAGTGCG ATTCCCGTGC CTGGT | 175 |

(2) INFORMATION FOR SEQ ID NO:61:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:61:

```
ACCCCACTTT TCCTCCTGTG AGCAGTCTGG ACTTCTCACT GCTACATGAT GAGGGTGAGT      60

GGTTGTTGCT CTTCAACAGT ATCCTCCCCT TTCCGGATCT GCTGAGCCGG ACAGCAGTGC     120

TGGACTGCAC AGCCCCGGGG CTCCACATTG CTGT                                 154
```

(2) INFORMATION FOR SEQ ID NO:62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:62:

```
CGCTCGAGCC CTATAGTGAG TCGTATTAGA                                      30
```

(2) INFORMATION FOR SEQ ID NO:63:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:63:

```
ACAAGTCATT TCAGCACCCT TTGCTCTTCA AAACTGACCA TCTTTTATAT TTAATGCTTC      60

CTGTATGAAT AAAAATGGTT ATGTCAAGT                                       89
```

(2) INFORMATION FOR SEQ ID NO:64:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:64:

```
ACCGGAGTAA CTGAGTCGGG ACGCTGAATC TGAATCCACC AATAAATAAA GGTTCTGCAG      60

AATCAGTGCA TCCAGGATTG GTCCTTGGAT CTGGGGT                              97
```

(2) INFORMATION FOR SEQ ID NO:65:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:65:

```
ACAACAANAA NTCCCTTCTT TAGGCCACTG ATGGAAACCT GGAACCCCCT TTTGATGGCA    60

GCATGGCGTC CTAGGCCTTG ACACAGCGGC TGGGGTTTGG GCTNTCCCAA ACCGCACACC   120

CCAACCCTGG TCTACCCACA NTTCTGGCTA TGGGCTGTCT CTGCCACTGA ACATCAGGGT   180

TCGGTCATAA NATGAAATCC CAANGGGGAC AGAGGTCAGT AGAGGAAGCT CAATGAGAAA   240

GGTGCTGTTT GCTCAGCCAG AAAACAGCTG CCTGGCATTC GCCGCTGAAC TATGAACCCG   300

TGGGGGTGAA CTACCCCCAN GAGGAATCAT GCCTGGGCGA TGCAANGGTG CCAACAGGAG   360

GGGCGGGAGG AGCATGT                                                 377
```

(2) INFORMATION FOR SEQ ID NO:66:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:66:

```
ACGCCTTTCC CTCAGAATTC AGGGAAGAGA CTGTCGCCTG CCTTCCTCCG TTGTTGCGTG    60

AGAACCCGTG TGCCCCTTCC CACCATATCC ACCCTCGCTC CATCTTTGAA CTCAAACACG   120

AGGAACTAAC TGCACCCTGG TCCTCTCCCC AGTCCCCAGT TCACCCTCCA TCCCTCACCT   180

TCCTCCACTC TAAGGGATAT CAACACTGCC CAGCACAGGG GCCCTGAATT TATGTGGTTT   240

TTATATATTT TTTAATAAGA TGCACTTTAT GTCATTTTTT AATAAAGTCT GAAGAATTAC   300

TGTTT                                                              305
```

(2) INFORMATION FOR SEQ ID NO:67:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:67:

```
ACTACACACA CTCCACTTGC CCTTGTGAGA CACTTTGTCC CAGCACTTTA GGAATGCTGA    60

GGTCGGACCA GCCACATCTC ATGTGCAAGA TTGCCCAGCA GACATCAGGT CTGAGAGTTC   120

CCCTTTTAAA AAGGGGACT TGCTTAAAAA AGAAGTCTAG CCACGATTGT GTAGAGCAGC   180
```

TGTGCTGTGC TGGAGATTCA CTTTTGAGAG AGTTCTCCTC TGAGACCTGA TCTTTAGAGG          240

CTGGGCAGTC TTGCACATGA GATGGGGCTG GTCTGATCTC AGCACTCCTT AGTCTGCTTG          300

CCTCTCCCAG GGCCCCAGCC TGGCCACACC TGCTTACAGG GCACTCTCAG ATGCCCATAC          360

CATAGTTTCT GTGCTAGTGG ACCGT                                               385

(2) INFORMATION FOR SEQ ID NO:68:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:68:

ACTTAACCAG ATATATTTTT ACCCCAGATG GGGATATTCT TTGTAAAAAA TGAAAATAAA          60

GTTTTTTTAA TGG                                                             73

(2) INFORMATION FOR SEQ ID NO:69:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:69:

ACTAGTCCAG TGTGGTGGAA TTCCATTGTG TTGGGGGCTC TCACCCTCCT CTCCTGCAGC          60

TCCAGCTTTG TGCTCTGCCT CTGAGGAGAC CATGGCCCAG CATCTGAGTA CCCTGCTGCT         120

CCTGCTGGCC ACCCTAGCTG TGGCCCTGGC CTGGAGCCCC AAGGAGGAGG ATAGGATAAT         180

CCCGGGTGGC ATCTATAACG CAGACCTCAA TGATGAGTGG GTACAGCGTG CCCTTCACTT         240

CGCCATCAGC GAGTATAACA AGGCCACCAA AGATGACTAC TACAGACGTC CGCTGCGGGT         300

ACTAAGAGCC AGGCAACAGA CCGTTGGGGG GGTGAATTAC TTCTTCGACG TAGAGGTGGG         360

CCGAACCATA TGTACCAAGT CCCAGCCCAA CTTGGACACC TGTGCCTTCC ATGAACAGCC         420

AGAACTGCAG AAGAAACAGT TGTGCTCTTT CGAGATCTAC GAAGTTCCCT GGGGAGAACA         480

GAANGTCCCT GGGTGAAATC CAGGTGTCAA GAAATCCTAN GGATCTGTTG CCAGGC            536

(2) INFORMATION FOR SEQ ID NO:70:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:70:

```
ATGACCCCTA ACAGGGGCCC TCTCAGCCCT CCTAATGACC TCCGGCCTAG CCATGTGATT    60

TCACTTCCAC TCCATAACGC TCCTCATACT AGGCCTACTA ACCAACACAC TAACCATATA   120

CCAATGATGG CGCGATGTAA CACGAGAAAG CACATACCAA GGCCACCACA CACCACCTGT   180

CCAAAAAGGC CTTCGATACG GGATAATCCT ATTTATTACC TCAGAAGTTT TTTTCTTCGC   240

AGGGATTTTT CTGAGCCTTT TACCACTCCA GCCTAGCCCC TACCCCCCAA CTAGGAGGGC   300

ACTGGCCCCC AACAGGCATC ACCCCGCTAA ATCCCCTAGA AGTCCCACTC CTAAACACAT   360

CCGTATTACT CGCATCAGGA GTATCAATCA CCTGAGCTCA CCATAGTCTA ATAGAAAACA   420

ACCGAAACCA AATTATTCAA AGCACTGCTT ATTACAATTT TACTGGGTCT CTATTTT     477
```

(2) INFORMATION FOR SEQ ID NO:71:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:71:

```
AGAGCTATAG GTACAGTGTG ATCTCAGCTT TGCAAACACA TTTTCTACAT AGATAGTACT    60

AGGTATTAAT AGATATGTAA AGAAAGAAAT CACACCATTA ATAATGGTAA GATTGGTTTA   120

TGTGATTTTA GTGGTATTTT TGGCACCCTT ATATATGTTT TCCAAACTTT CAGCAGTGAT   180

ATTATTTCCA TAACTTAAAA AGTGAGTTTG AAAAAGAAAA TCTCCAGCAA GCATCTCATT   240

TAAATAAAGG TTTGTCATCT TTAAAAATAC AGCAATATGT GACTTTTTAA AAAAGCTGTC   300

AAATAGGTGT GACCCTACTA ATAATTATTA GAAATACATT TAAAAACATC GAGTACCTCA   360

AGTCAGTTTG CCTTGAAAAA TATCAAATAT AACTCTTAGA GAAATGTACA TAAAAGAATG   420

CTTCGTAATT TTGGAGTANG AGGTTCCCTC CTCAATTTTG TATTTTTAAA AAGTACATGG   480

TAAAAAAAAA AATTCACAAC AGTATATAAG GCTGTAAAAT GAAGAATTCT GCC          533
```

(2) INFORMATION FOR SEQ ID NO:72:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:72:

```
TATTACGGAA AAACACACCA CATAATTCAA CTANCAAAGA ANACTGCTTC AGGGCGTGTA    60

AAATGAAAGG CTTCCAGGCA GTTATCTGAT TAAAGAACAC TAAAAGAGGG ACAAGGCTAA   120

AAGCCGCAGG ATGTCTACAC TATANCAGGC GCTATTTGGG TTGGCTGGAG GAGCTGTGGA   180

AAACATGGAN AGATTGGTGC TGGANATCGC CGTGGCTATT CCTCATTGTT ATTACANAGT   240

GAGGTTCTCT GTGTGCCCAC TGGTTTGAAA ACCGTTCTNC AATAATGATA GAATAGTACA   300

CACATGAGAA CTGAAATGGC CCAAACCCAG AAAGAAAGCC CAACTAGATC CTCAGAAANAC   360

GCTTCTAGGG ACAATAACCG ATGAAGAAAA GATGGCCTCC TTGTGCCCCC GTCTGTTATG   420
```

```
ATTTCTCTCC ATTGCAGCNA NAAACCCGTT CTTCTAAGCA AACNCAGGTG ATGATGGCNA      480

AAATACACCC CCTCTTGAAG NACCNGGAGG A                                    511

(2) INFORMATION FOR SEQ ID NO:73:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:73:

CAGTGCCAGC ACTGGTGCCA GTACCAGTAC CAATAACAGT GCCAGTGCCA GTGCCAGCAC       60

CAGTGGTGGC TTCAGTGCTG GTGCCAGCCT GACCGCCACT CTCACATTTG GGCTCTTCGC      120

TGGCCTTGGT GGAGCTGGTG CCAGCACCAG TGGCAGCTCT GGTGCCTGTG GTTTCTCCTA      180

CAAGTGAGAT TTTAGATATT GTTAATCCTG CCAGTCTTTC TCTTCAAGCC AGGGTGCATC      240

CTCAGAAACC TACTCAACAC AGCACTCTAG GCAGCCACTA TCAATCAATT GAAGTTGACA      300

CTCTGCATTA AATCTATTTG CCATTTCTGA AAAAAAAAAA AAAAAAAGGG CGGCCGCTCG      360

ANTCTAGAGG GCCCGTTTAA ACCCGCTGAT CAGCCTCGAC TGTGCCTTCT ANTTGCCAGC      420

CATCTGTTGT TTGCCCCTCC CCCGNTGCCT TCCTTGACCC TGGAAAGTGC CACTCCCACT      480

GTCCTTTCCT AANTAAAAT                                                  499

(2) INFORMATION FOR SEQ ID NO:74:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:74:

TTTCATAGGA GAACACACTG AGGAGATACT TGAAGAATTT GGATTCAGCC GCGAAGAGAT       60

TTATCAGCTT AACTCAGATA AAATCATTGA AAGTAATAAG GTAAAAGCTA GTCTCTAACT      120

TCCAGGCCCA CGGCTCAAGT GAATTTGAAT ACTGCATTTA CAGTGTAGAG TAACACATAA      180

CATTGTATGC ATGGAAACAT GGAGGAACAG TATTACAGTG TCCTACCACT CTAATCAAGA      240

AAAGAATTAC AGACTCTGAT TCTACAGTGA TGATTGAATT CTAAAAATGG TAATCATTAG      300

GGCTTTTGAT TTATAANACT TTGGGTACTT ATACTAAATT ATGGTAGTTA TACTGCCTTC      360

CAGTTTGCTT GATATATTTG TTGATATTAA GATTCTTGAC TTATATTTTG AATGGGTTCT      420

ACTGAAAAAN GAATGATATA TTCTTGAAGA CATCGATATA CATTTATTTA CACTCTTGAT      480

TCTACAATGT AGAAAATGAA GGAAATGCCC CAAATTGTAT GGTGATAAAA GTCCCGT         537

(2) INFORMATION FOR SEQ ID NO:75:

(i) SEQUENCE CHARACTERISTICS:
        (A) LENGTH: 467 base pairs
        (B) TYPE: nucleic acid
```

```
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO:75:

CAAANACAAT TGTTCAAAAG ATGCAAATGA TACACTACTG CTGCAGCTCA CAAACACCTC      60

TGCATATTAC ACGTACCTCC TCCTGCTCCT CAAGTAGTGT GGTCTATTTT GCCATCATCA     120

CCTGCTGTCT GCTTAGAAGA ACGGCTTTCT GCTGCAANGG AGAGAAATCA TAACAGACGG     180

TGGCACAAGG AGGCCATCTT TTCCTCATCG GTTATTGTCC CTAGAAGCGT CTTCTGAGGA     240

TCTAGTTGGG CTTTCTTTCT GGGTTTGGGC CATTTCANTT CTCATGTGTG TACTATTCTA     300

TCATTATTGT ATAACGGTTT TCAAACCNGT GGGCACNCAG AGAACCTCAC TCTGTAATAA     360

CAATGAGGAA TAGCCACGGT GATCTCCAGC ACCAAATCTC TCCATGTTNT TCCAGAGCTC     420

CTCCAGCCAA CCCAAATAGC CGCTGCTATN GTGTAGAACA TCCCTGN                   467

(2) INFORMATION FOR SEQ ID NO:76:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO:76:

AAGCTGACAG CATTCGGGCC GAGATGTCTC GCTCCGTGGC CTTAGCTGTG CTCGCGCTAC      60

TCTCTCTTTC TGGCCTGGAG GCTATCCAGC GTACTCCAAA GATTCAGGTT TACTCACGTC     120

ATCCAGCAGA GAATGGAAAG TCAAATTTCC TGAATTGCTA TGTGTCTGGG TTTCATCCAT     180

CCGACATTGA AGTTGACTTA CTGAAGAATG GAGAGAGAAT TGAAAAAGTG GAGCATTCAG     240

ACTTGTCTTT CAGCAAGGAC TGGTCTTTCT ATCTCTTGTA CTACACTGAA TTCACCCCCA     300

CTGAAAAAGA TGAGTATGCC TGCCGTGTGA ACCATGTGAC TTTGTCACAG CCCAAGATNG     360

TTNAGTGGGA TCGANACATG TAAGCAGCAN CATGGGAGGT                           400

(2) INFORMATION FOR SEQ ID NO:77:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo Sapiens (xi) SEQUENCE DESCRIPTION: SEQ ID NO:77:

CTGGAGTGCC TTGGTGTTTC AAGCCCCTGC AGGAAGCAGA ATGCACCTTC TGAGGCACCT      60

CCAGCTGCCC CGGCGGGGGA TGCGAGGCTC GGAGCACCCT TGCCCGGCTG TGATTGCTGC     120

CAGGCACTGT TCATCTCAGC TTTTCTGTCC CTTTGCTCCC GGCAAGCGCT TCTGCTGAAA     180

GTTCATATCT GGAGCCTGAT GTCTTAACGA ATAAAGGTCC CATGCTCCAC CCGAAAAAAA     240
```

AAAAAAAA                                                         248

(2) INFORMATION FOR SEQ ID NO:78:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:78:

ACTAGTCCAG TGTGGTGGAA TTCCATTGTG TTGGGCCCAA CACAATGGCT ACCTTTAACA    60

TCACCCAGAC CCCGCCCTGC CCGTGCCCCA CGCTGCTGCT AACGACAGTA TGATGCTTAC   120

TCTGCTACTC GGAAACTATT TTTATGTAAT TAATGTATGC TTTCTTGTTT ATAAATGCCT   180

GATTTAAAAA AAAAAAAAAA A                                             201

(2) INFORMATION FOR SEQ ID NO:79:

(i) SEQUENCE CHARACTERISTICS:
        (A) LENGTH: 552 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:79:

TCCTTTTGTT AGGTTTTTGA GACAACCCTA GACCTAAACT GTGTCACAGA CTTCTGAATG    60

TTTAGGCAGT GCTAGTAATT TCCTCGTAAT GATTCTGTTA TTACTTTCCT ATTCTTTATT   120

CCTCTTTCTT CTGAAGATTA ATGAAGTTGA AAATTGAGGT GGATAAATAC AAAAAGGTAG   180

TGTGATAGTA TAAGTATCTA AGTGCAGATG AAAGTGTGTT ATATATATCC ATTCAAAATT   240

ATGCAAGTTA GTAATTACTC AGGGTTAACT AAATTACTTT AATATGCTGT TGAACCTACT   300

CTGTTCCTTG GCTAGAAAAA ATTATAAACA GGACTTTGTT AGTTTGGGAA GCCAAATTGA   360

TAATATTCTA TGTTCTAAAA GTTGGGCTAT ACATAAANTA TNAAGAAATA TGGAATTTTA   420

TTCCCAGGAA TATGGGGTTC ATTTATGAAT ANTACCCGGG ANAGAAGTTT TGANTNAAAC   480

CNGTTTTGGT TAATACGTTA ATATGTCCTN AATNAACAAG GCNTGACTTA TTTCCAAAAA   540

AAAAAAAAAA AA                                                       552

(2) INFORMATION FOR SEQ ID NO:80:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:80:

```
ACAGGGATTT GAGATGCTAA GGCCCCAGAG ATCGTTTGAT CCAACCCTCT TATTTTCAGA        60

GGGGAAAATG GGGCCTAGAA GTTACAGAGC ATCTAGCTGG TGCGCTGGCA CCCCTGGCCT       120

CACACAGACT CCCGAGTAGC TGGGACTACA GGCACACAGT CACTGAAGCA GGCCCTGTTT       180

GCAATTCACG TTGCCACCTC CAACTTAAAC ATTCTTCATA TGTGATGTCC TTAGTCACTA       240

AGGTTAAACT TTCCCACCCA GAAAAGGCAA CTTAGATAAA ATCTTAGAGT ACTTTCATAC       300

TCTTCTAAGT CCTCTTCCAG CCTCACTTTG AGTCCTCCTT GGGGGTTGAT AGGAANTNTC       360

TCTTGGCTTT CTCAATAAAA TCTCTATCCA TCTCATGTTT AATTTGGTAC GCNTAAAAAT       420

GCTGAAAAAA TTAAAATGTT CTGGTTTCNC TTTAAAAAAA AAAAAAAAAA AAAAAA          476

(2) INFORMATION FOR SEQ ID NO:81:

(i) SEQUENCE CHARACTERISTICS:
        (A) LENGTH: 232 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:81:

TTTTTTTTTG TATGCCNTCN CTGTGGNGTT ATTGTTGCTG CCACCCTGGA GGAGCCCAGT        60

TTCTTCTGTA TCTTTCTTTT CTGGGGATC TTCCTGGCTC TGCCCCTCCA TTCCCAGCCT        120

CTCATCCCCA TCTTGCACTT TTGCTAGGGT TGGAGGCGCT TTCCTGGTAG CCCCTCAGAG       180

ACTCAGTCAG CGGGAATAAG TCCTAGGGGT GGGGGGTGTG GCAAGCCGGC CT              232

(2) INFORMATION FOR SEQ ID NO:82:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:82:

AGGCGGGAGC AGAAGCTAAA GCCAAAGCCC AAGAAGAGTG GCAGTGCCAG CACTGGTGCC        60

AGTACCAGTA CCAATAACAT GCCAGTGCCA GTGCCAGCAC CAGTGGTGGC TTCAGTGCTG       120

GTGCCAGCCT GACCGCCACT CTCACATTTG GGCTCTTCGC TGGCCTTGGT GGAGCTGGTG       180

CCAGCACCAG TGGCAGCTCT GGTGCCTGTG GTTTCTCCTA CAAGTGAGAT TTTAGATATT       240

GTTAATCCTG CCAGTCTTTC TCTTCAAGCC AGGGTGCATC CTCAGAAACC TACTCAACAC       300

AGCACTCTNG GCAGCCACTA TCAATCAATT GAAGTTGACA CTCTGCATTA AATCTATTTG       360

CCATTTCAAA AAAAAAAAAA AAA                                              383

(2) INFORMATION FOR SEQ ID NO:83:

(i) SEQUENCE CHARACTERISTICS:
        (A) LENGTH: 494 base pairs
        (B) TYPE: nucleic acid
        (C) STRANDEDNESS: single
        (D) TOPOLOGY: linear
```

```
    (ii) MOLECULE TYPE: cDNA (vi) ORIGINAL SOURCE:
         (A) ORGANISM: Homo sapiens (xi) SEQUENCE DESCRIPTION: SEQ ID NO:83:

ACCGAATTGG GACCGCTGGC TTATAAGCGA TCATGTCCTC CAGTATTACC TCAACGAGCA      60

GGGAGATCGA GTCTATACGC TGAAGAAATT TGACCCGATG GGACAACAGA CCTGCTCAGC     120

CCATCCTGCT CGGTTCTCCC CAGATGACAA ATACTCTCGA CACCGAATCA CCATCAAGAA     180

ACGCTTCAAG GTGCTCATGA CCCAGCAACC GCGCCCTGTC CTCTGAGGGT CCTTAAACTG     240

ATGTCTTTTC TGCCACCTGT TACCCCTCGG AGACTCCGTA ACCAAACTCT TCGGACTGTG     300

AGCCCTGATG CCTTTTTGCC AGCCATACTC TTTGGCNTCC AGTCTCTCGT GGCGATTGAT     360

TATGCTTGTG TGAGGCAATC ATGGTGGCAT CACCCATNAA GGGAACACAT TTGANTTTTT     420

TTTCNCATAT TTTAAATTAC NACCAGAATA NTTCAGAATA AATGAATTGA AAAACTCTTA     480

AAAAAAAAAA AAAA                                                      494

(2) INFORMATION FOR SEQ ID NO:84:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO:84:

GCTGGTAGCC TATGGCGTGG CCACGGANGG GCTCCTGAGG CACGGGACAG TGACTTCCCA      60

AGTATCCTGC GCCGCGTCTT CTACCGTCCC TACCTGCAGA TCTTCGGGCA GATTCCCCAG     120

GAGGACATGG ACGTGGCCCT CATGGAGCAC AGCAACTGCT CGTCGGAGCC CGGCTTCTGG     180

GCACACCCTC CTGGGGCCCA GGCGGGCACC TGCGTCTCCC AGTATGCCAA CTGGCTGGTG     240

GTGCTGCTCC TCGTCATCTT CCTGCTCGTG GCCAACATCC TGCTGGTCAC TTGCTCATTG     300

CCATGTTCAG TTACACATTC GGCAAAGTAC AGGGCAACAG CNATCTCTAC TGGGAAGGCC     360

AGCGTTNCCG CCTCATCCGG                                                 380

(2) INFORMATION FOR SEQ ID NO:85:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO:85:

GAGTTAGCTC CTCCACAACC TTGATGAGGT CGTCTGCAGT GGCCTCTCGC TTCATACCGC      60

TNCCATCGTC ATACTGTAGG TTTGCCACCA CCTCCTGCAT CTTGGGGCGG CTAATATCCA     120

GGAAACTCTC AATCAAGTCA CCGTCNATNA AACCTGTGGC TGGTTCTGTC TTCCGCTCGG     180

TGTGAAAGGA TCTCCAGAAG GAGTGCTCGA TCTTCCCCAC ACTTTTGATG ACTTTATTGA     240
```

```
GTCGATTCTG CATGTCCAGC AGGAGGTTGT ACCAGCTCTC TGACAGTGAG GTCACCAGCC    300

CTATCATGCC NTTGAACGTG CCGAAGAACA CCGAGCCTTG TGTGGGGGGT GNAGTCTCAC    360

CCAGATTCTG CATTACCAGA NAGCCGTGGC AAAAGANATT GACAACTCGC CCAGGNNGAA    420

AAAGAACACC TCCTGGAAGT GCTNGCCGCT CCTCGTCCNT TGGTGGNNGC GCNTNCCTTT    480

T                                                                    481

(2) INFORMATION FOR SEQ ID NO:86:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:86:

AACATCTTCC TGTATAATGC TGTGTAATAT CGATCCGATN TTGTCTGCTG AGAATTCATT     60

ACTTGGAAAA GCAACTTNAA GCCTGGACAC TGGTATTAAA ATTCACAATA TGCAACACTT    120

TAAACAGTGT GTCAATCTGC TCCCTTACTT TGTCATCACC AGTCTGGGAA TAAGGGTATG    180

CCCTATTCAC ACCTGTTAAA AGGGCGCTAA GCATTTTTGA TTCAACATCT TTTTTTTTGA    240

CACAAGTCCG AAAAAAGCAA AAGTAAACAG TTNTTAATTT GTTAGCCAAT TCACTTTCTT    300

CATGGGACAG AGCCATTTGA TTTAAAAAGC AAATTGCATA ATATTGAGCT TTGGGAGCTG    360

ATATNTGAGC GGAAGANTAG CCTTTCTACT TCACCAGACA CAACTCCTTT CATATTGGGA    420

TGTTNACNAA AGTTATGTCT CTTACAGATG GGATGCTTTT GTGGCAATTC TG           472

(2) INFORMATION FOR SEQ ID NO:87:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:87:

AGAAACCAGT ATCTCTNAAA ACAACCTCTC ATACCTTGTG GACCTAATTT TGTGTGCGTG     60

TGTGTGTGCG CGCATATTAT ATAGACAGGC ACATCTTTTT TACTTTTGTA AAAGCTTATG    120

CCTCTTTGGT ATCTATATCT GTGAAAGTTT TAATGATCTG CCATAATGTC TTGGGGACCT    180

TTGTCTTCTG TGTAAATGGT ACTAGAGAAA ACACCTATNT TATGAGTCAA TCTAGTTNGT    240

TTTATTCGAC ATGAAGGAAA TTTCCAGATN ACAACACTNA CAAACTCTCC CTTGACTAGG    300

GGGGACAAAG AAAAGCANAA CTGAACATNA GAAACAATTN CCTGGTGAGA AATTNCATAA    360

ACAGAAATTG GGTNGTATAT TGAAANANNG CATCATTNAA ACGTTTTTTT TTT           413

(2) INFORMATION FOR SEQ ID NO:88:

(i) SEQUENCE CHARACTERISTICS:
        (A) LENGTH: 448 base pairs
        (B) TYPE: nucleic acid
        (C) STRANDEDNESS: single
```

(D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:88:

| | | | | | |
|---|---|---|---|---|---|
| CGCAGCGGGT | CCTCTCTATC | TAGCTCCAGC | CTCTCGCCTG | CCCCACTCCC | CGCGTCCCGC | 60 |
| GTCCTAGCCN | ACCATGGCCG | GGCCCCTGCG | CGCCCCGCTG | CTCCTGCTGG | CCATCCTGGC | 120 |
| CGTGGCCCTG | GCCGTGAGCC | CCGCGGCCGG | CTCCAGTCCC | GGCAAGCCGC | CGCGCCTGGT | 180 |
| GGGAGGCCCA | TGGACCCCGC | GTGGAAGAAG | AAGGTGTGCG | GCGTGCACTG | GACTTTGCCG | 240 |
| TCGGCNANTA | CAACAAACCC | GCAACNACTT | TTACCNAGCN | CGCGCTGCAG | GTTGTGCCGC | 300 |
| CCCAANCAAA | TTGTTACTNG | GGGTAANTAA | TTCTTGGAAG | TTGAACCTGG | GCCAAACNNG | 360 |
| TTTACCAGAA | CCNAGCCAAT | TNGAACAATT | NCCCCTCCAT | AACAGCCCCT | TTTAAAAAGG | 420 |
| GAANCANTCC | TGNTCTTTTC | CAAATTTT | | | | 448 |

(2) INFORMATION FOR SEQ ID NO:89:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:89:

| | | | | | |
|---|---|---|---|---|---|
| GAATTTTGTG | CACTGGCCAC | TGTGATGGAA | CCATTGGGCC | AGGATGCTTT | GAGTTTATCA | 60 |
| GTAGTGATTC | TGCCAAAGTT | GGTGTTGTAA | CATGAGTATG | TAAAATGTCA | AAAAATTAGC | 120 |
| AGAGGTCTAG | GTCTGCATAT | CAGCAGACAG | TTTGTCCGTG | TATTTTGTAG | CCTTGAAGTT | 180 |
| CTCAGTGACA | AGTTNNTTCT | GATGCGAAGT | TCTNATTCCA | GTGTTTTAGT | CCTTTGCATC | 240 |
| TTTNATGTTN | AGACTTGCCT | CTNTNAAATT | GCTTTTGTNT | TCTGCAGGTA | CTATCTGTGG | 300 |
| TTTAACAAAA | TAGAANNACT | TCTCTGCTTN | GAANATTTGA | ATATCTTACA | TCTNAAAATN | 360 |
| AATTCTCTCC | CCATANNAAA | ACCCANGCCC | TTGGGANAAT | TTGAAAAANG | GNTCCTTCNN | 420 |
| AATTCNNANA | ANTTCAGNTN | TCATACAACA | NAACNGGANC | CCC | | 463 |

(2) INFORMATION FOR SEQ ID NO:90:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:90:

| | | | | | |
|---|---|---|---|---|---|
| GGGGATTGAA | GGTCTNTTNT | ACTGTCGGAC | TGTTCANCCA | CCAACTCTAC | AAGTTGCTGT | 60 |
| CTTCCACTCA | CTGTCTGTAA | GCNTNTTAAC | CCAGACTGTA | TCTTCATAAA | TAGAACAAAT | 120 |
| TCTTCACCAG | TCACATCTTC | TAGGACCTTT | TTGGATTCAG | TTAGTATAAG | CTCTTCCACT | 180 |

```
TCCTTTGTTA AGACTTCATC TGGTAAAGTC TTAAGTTTTG TAGAAAGGAA TTTAATTGCT      240

CGTTCTCTAA CAATGTCCTC TCCTTGAAGT ATTTGGCTGA ACAACCCACC TNAAGTCCCT      300

TTGTGCATCC ATTTTAAATA TACTTAATAG GGCATTGGTN CACTAGGTTA AATTCTGCAA      360

GAGTCATCTG TCTGCAAAAG TTGCGTTAGT ATATCTGCCA                            400

(2) INFORMATION FOR SEQ ID NO:91:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:91:

GAGCTCGGAT CCAATAATCT TTGTCTGAGG GCAGCACACA TATNCAGTGC CATGGNAACT       60

GGTCTACCCC ACATGGGAGC AGCATGCCGT AGNTATATAA GGTCATTCCC TGAGTCAGAC      120

ATGCCTCTTT GACTACCGTG TGCCAGTGCT GGTGATTCTC ACACACCTCC NNCCGCTCTT      180

TGTGGAAAAA CTGGCACTTG NCTGAACTA GCAAGACATC ACTTACAAAT TCACCCACGA       240

GACACTTGAA AGGTGTAACA AAGCGACTCT TGCATTGCTT TTTGTCCCTC CGGCACCAGT      300

TGTCAATACT AACCCGCTGG TTTGCCTCCA TCACATTTGT GATCTGTAGC TCTGGATACA      360

TCTCCTGACA GTACTGAAGA ACTTCTTCTT TTGTTTCAAA AGCAACTCTT GGTGCCTGTT      420

NGATCAGGTT CCCATTTCCC AGTCCGAATG TTCACATGGC ATATNTTACT TCCCACAAAA      480

(2) INFORMATION FOR SEQ ID NO:92:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:92:

ATACAGCCCA NATCCCACCA CGAAGATGCG CTTGTTGACT GAGAACCTGA TGCGGTCACT       60

GGTCCCGCTG TAGCCCCAGC GACTCTCCAC CTGCTGGAAG CGGTTGATGC TGCACTCCTT      120

CCCACGCAGG CAGCAGCGGG GCCGGTCAAT GAACTCCACT CGTGGCTTGG GGTTGACGGT      180

TAANTGCAGG AAGAGGCTGA CCACCTCGCG GTCCACCAGG ATGCCCGACT GTGCGGGACC      240

TGCAGCGAAA CTCCTCGATG GTCATGAGCG GGAAGCGAAT GANGCCCAGG GCCTTGCCCA      300

GAACCTTCCG CCTGTTCTCT GGCGTCACCT GCAGCTGCTG CCGCTNACAC TCGGCCTCGG      360

ACCAGCGGAC AAACGGCGTT GAACAGCCGC ACCTCACGGA TGCCCANTGT GTCGCGCTCC      420

AGGAACGGCN CCAGCGTGTC CAGGTCAATG TCGGTGAANC CTCCGCGGGT AATGGCG         477

(2) INFORMATION FOR SEQ ID NO:93:

(i) SEQUENCE CHARACTERISTICS:
        (A) LENGTH: 377 base pairs
        (B) TYPE: nucleic acid
        (C) STRANDEDNESS: single
```

```
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:93:

GAACGGCTGG ACCTTGCCTC GCATTGTGCT GCTGGCAGGA ATACCTTGGC AAGCAGCTCC      60

AGTCCGAGCA GCCCCAGACC GCTGCCGCCC GAAGCTAAGC CTGCCTCTGG CCTTCCCCTC     120

CGCCTCAATG CAGAACCANT AGTGGGAGCA CTGTGTTTAG AGTTAAGAGT GAACACTGTN     180

TGATTTTACT TGGGAATTTC CTCTGTTATA TAGCTTTTCC CAATGCTAAT TTCCAAACAA     240

CAACAACAAA ATAACATGTT TGCCTGTTNA GTTGTATAAA AGTANGTGAT TCTGTATNTA     300

AAGAAAATAT TACTGTTACA TATACTGCTT GCAANTTCTG TATTTATTGG TNCTCTGGAA     360

ATAAATATAT TATTAAA                                                    377

(2) INFORMATION FOR SEQ ID NO:94:

(i) SEQUENCE CHARACTERISTICS:
            (A) LENGTH: 495 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:94:

CCCTTTGAGG GGTTAGGGTC CAGTTCCCAG TGGAAGAAAC AGGCCAGGAG AANTGCGTGC      60

CGAGCTGANG CAGATTTCCC ACAGTGACCC CAGAGCCCTG GGCTATAGTC TCTGACCCCT     120

CCAAGGAAAG ACCACCTTCT GGGGACATGG GCTGGAGGGC AGGACCTAGA GGCACCAAGG     180

GAAGGCCCCA TTCCGGGGCT GTTCCCCGAG GAGGAAGGGA AGGGGCTCTG TGTGCCCCCC     240

ACGAGGAANA GGCCCTGANT CCTGGGATCA NACACCCCTT CACGTGTATC CCCACACAAA     300

TGCAAGCTCA CCAAGGTCCC CTCTCAGTCC CTTCCCTACA CCCTGAACGG NCACTGGCCC     360

ACACCCACCC AGANCANCCA CCCGCCATGG GGAATGTNCT CAAGGAATCG CNGGGCAACG     420

TGGACTCTNG TCCCNNAAGG GGGCAGAATC TCCAATAGAN GGANNGAACC CTTGCTNANA     480

AAAAAAAANA AAAAA                                                     495

(2) INFORMATION FOR SEQ ID NO:95:

(i) SEQUENCE CHARACTERISTICS:
            (A) LENGTH: 472 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:95:

GGTTACTTGG TTTCATTGCC ACCACTTAGT GGATGTCATT TAGAACCATT TTGTCTGCTC      60

CCTCTGGAAG CCTTGCGCAG AGCGGACTTT GTAATTGTTG GAGAATAACT GCTGAATTTT     120

TAGCTGTTTT GAGTTGATTC GCACCACTGC ACCACAACTC AATATGAAAA CTATTTNACT     180
```

```
TATTTATTAT CTTGTGAAAA GTATACAATG AAAATTTTGT TCATACTGTA TTTATCAAGT      240

ATGATGAAAA GCAATAGATA TATATTCTTT TATTATGTTN AATTATGATT GCCATTATTA      300

ATCGGCAAAA TGTGGAGTGT ATGTTCTTTT CACAGTAATA TATGCCTTTT GTAACTTCAC      360

TTGGTTATTT TATTGTAAAT GAATTACAAA ATTCTTAATT TAAGAAAATG GTANGTTATA      420

TTTANTTCAN TAATTTCTTT CCTTGTTTAC GTTAATTTTG AAAAGAATGC AT              472

(2) INFORMATION FOR SEQ ID NO:96:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:96:

CTGAAGCATT TCTTCAAACT TNTCTACTTT TGTCATTGAT ACCTGTAGTA AGTTGACAAT       60

GTGGTGAAAT TTCAAAATTA TATGTAACTT CTACTAGTTT TACTTTCTCC CCCAAGTCTT      120

TTTTAACTCA TGATTTTTAC ACACACAATC CAGAACTTAT TATATAGCCT CTAAGTCTTT      180

ATTCTTCACA GTAGATGATG AAAGAGTCCT CCAGTGTCTT GNGCANAATG TTCTAGNTAT      240

AGCTGGATAC ATACNGTGGG AGTTCTATAA ACTCATACCT CAGTGGGACT NAACCAAAAT      300

TGTGTTAGTC TCAATTCCTA CCACACTGAG GGAGCCTCCC AAATCACTAT ATTCTTATCT      360

GCAGGTACTC CTCCAGAAAA ACNGACAGGG CAGGCTTGCA TGAAAAAGTN ACATCTGCGT      420

TACAAAGTCT ATCTTCCTCA NANGTCTGTN AAGGAACAAT TTAATCTTCT AGCTTT         476

(2) INFORMATION FOR SEQ ID NO:97:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:97:

ACTCTTTCTA ATGCTGATAT GATCTTGAGT ATAAGAATGC ATATGTCACT AGAATGGATA       60

AAATAATGCT GCAAACTTAA TGTTCTTATG CAAAATGGAA CGCTAATGAA ACACAGCTTA      120

CAATCGCAAA TCAAAACTCA CAAGTGCTCA TCTGTTGTAG ATTTAGTGTA ATAAGACTTA      180

GATTGTGCTC CTTCGGATAT GATTGTTTCT CANATCTTGG GCAATNTTCC TTAGTCAAAT      240

CAGGCTACTA GAATTCTGTT ATTGGATATN TGAGAGCATG AAATTTTTAA NAATACACTT      300

GTGATTATNA AATTAATCAC AAATTTCACT TATACCTGCT ATCAGCAGCT AGAAAAACAT      360

NTNNTTTTTA NATCAAGTA TTTTGTGTTT GGAANTGTNN AAATGAAATC TGAATGTGGG       420

TTCNATCTTA TTTTTTCCCN GACNACTANT TNCTTTTTTA GGGNCTATTC TGANCCATC      479

(2) INFORMATION FOR SEQ ID NO:98:

(i) SEQUENCE CHARACTERISTICS:
        (A) LENGTH: 461 base pairs
```

(B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:98:

```
AGTGACTTGT CCTCCAACAA AACCCCTTGA TCAAGTTTGT GGCACTGACA ATCAGACCTA      60

TGCTAGTTCC TGTCATCTAT TCGCTACTAA ATGCAGACTG GAGGGACCA AAAAGGGGCA      120

TCAACTCCAG CTGGATTATT TTGGAGCCTG CAAATCTATT CCTACTTGTA CGGACTTTGA     180

AGTGATTCAG TTTCCTCTAC GGATGAGAGA CTGGCTCAAG AATATCCTCA TGCAGCTTTA     240

TGAAGCCACT CTGAACACGC TGGTTATCTA GATGAGAACA GAGAAATAAA GTCAGAAAAT    300

TTACCTGGAG AAAAGAGGCT TTGGCTGGGG ACCATCCCAT TGAACCTTCT CTTAAGGACT    360

TTAAGAAAAA CTACCACATG TTGTGTATCC TGGTGCCGGC CGTTTATGAA CTGACCACCC     420

TTTGGAATAA TCTTGACGCT CCTGAACTTG CTCCTCTGCG A                          461
```

(2) INFORMATION FOR SEQ ID NO:99:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:99:

```
GTGGCCGCGC GCAGGTGTTT CCTCGTACCG CAGGGCCCCC TCCCTTCCCC AGGCGTCCCT      60

CGGCGCCTCT GCGGGCCCGA GGAGGAGCGG CTGGCGGGTG GGGGGAGTGT GACCCACCCT     120

CGGTGAGAAA AGCCTTCTCT AGCGATCTGA GAGGCGTGCC TTGGGGGTAC C               171
```

(2) INFORMATION FOR SEQ ID NO:100:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:100:

```
CGGCCGCAAG TGCAACTCCA GCTGGGGCCG TGCGGACGAA GATTCTGCCA GCAGTTGGTC      60

CGACTGCGAC GACGGCGGCG GCGACAGTCG CAGGTGCAGC GCGGGCGCCT GGGGTCTTGC     120

AAGGCTGAGC TGACGCCGCA GAGGTCGTGT CACGTCCCAC GACCTTGACG CCGTCGGGGA    180

CAGCCGGAAC AGAGCCCGGT GAAGCGGGAG GCCTCGGGGA GCCCCTCGGG AAGGGCGGCC    240

CGAGAGATAC GCAGGTGCAG GTGGCCGCC                                         269
```

(2) INFORMATION FOR SEQ ID NO:101:

(i) SEQUENCE CHARACTERISTICS:

```
        (A) LENGTH: 405 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:101:

TTTTTTTTTT TTTTGGAATC TACTGCGAGC ACAGCAGGTC AGCAACAAGT TTATTTTGCA      60

GCTAGCAAGG TAACAGGGTA GGGCATGGTT ACATGTTCAG GTCAACTTCC TTTGTCGTGG     120

TTGATTGGTT TGTCTTTATG GGGGCGGGGT GGGGTAGGGG AAACGAAGCA AATAACATGG     180

AGTGGGTGCA CCCTCCCTGT AGAACCTGGT TACAAAGCTT GGGGCAGTTC ACCTGGTCTG     240

TGACCGTCAT TTTCTTGACA TCAATGTTAT TAGAAGTCAG GATATCTTTT AGAGAGTCCA     300

CTGTTCTGGA GGGAGATTAG GGTTTCTTGC CAAATCCAAC AAAATCCACT GAAAAAGTTG     360

GATGATCAGT ACGAATACCG AGGCATATTC TCATATCGGT GGCCA                     405

(2) INFORMATION FOR SEQ ID NO:102:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:102:

TTTTTTTTTT TTTTTTTTTT TTTTTTTTTT TTTTTTTTTT TTTTTTTTTT TTTTTTTTTT      60

GGCACTTAAT CCATTTTTAT TCAAAATGT CTACAAATTT AATCCCATTA TACGGTATTT      120

TCAAAATCTA AATTATTCAA ATTAGCCAAA TCCTTACCAA ATAATACCCA AAAATCAAAA     180

ATATACTTCT TTCAGCAAAC TTGTTACATA AATTAAAAAA ATATATACGG CTGGTGTTTT     240

CAAAGTACAA TTATCTTAAC ACTGCAAACA TTTTAAGGAA CTAAAATAAA AAAAACACT      300

CCGCAAAGGT TAAAGGGAAC AACAAATTCT TTTACAACAC CATTATAAAA ATCATATCTC     360

AAATCTTAGG GGAATATATA CTTCACACGG GATCTTAACT TTTACTCACT TGTTTATTT      420

TTTTAAACCA TTGTTTGGGC CCAACACAAT GGAATCCCCC CTGGACTAGT                470

(2) INFORMATION FOR SEQ ID NO:103:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:103:

TTTTTTTTTT TTTTTTTTGA CCCCCCTCTT ATAAAAAACA AGTTACCATT TTATTTTACT      60

TACACATATT TATTTTATAA TTGGTATTAG ATATTCAAAA GGCAGCTTTT AAAATCAAAC     120

TAAATGGAAA CTGCCTTAGA TACATAATTC TTAGGAATTA GCTTAAAATC TGCCTAAAGT     180
```

```
GAAAATCTTC TCTAGCTCTT TTGACTGTAA ATTTTTGACT CTTGTAAAAC ATCCAAATTC      240

ATTTTTCTTG TCTTTAAAAT TATCTAATCT TTCCATTTTT TCCCTATTCC AAGTCAATTT      300

GCTTCTCTAG CCTCATTTCC TAGCTCTTAT CTACTATTAG TAAGTGGCTT TTTTCCTAAA      360

AGGGAAAACA GGAAGAGAAA TGGCACACAA AACAAACATT TTATATTCAT ATTTCTACCT      420

ACGTTAATAA AATAGCATTT TGTGAAGCCA GCTCAAAAGA AGGCTTAGAT CCTTTTATGT      480

CCATTTTAGT CACTAAACGA TATCAAAGTG CCAGAATGCA AAAGGTTTGT GAACATTTAT      540

TCAAAAGCTA ATATAAGATA TTTCACATAC TCATCTTTCT G                          581

(2) INFORMATION FOR SEQ ID NO:104:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:104:

TTTTTTTTTT TTTTTTTTTT TTTTTCTCTT CTTTTTTTTT GAAATGAGGA TCGAGTTTTT       60

CACTCTCTAG ATAGGGCATG AAGAAAACTC ATCTTTCCAG CTTTAAAATA ACAATCAAAT      120

CTCTTATGCT ATATCATATT TTAAGTTAAA CTAATGAGTC ACTGGCTTAT CTTCTCCTGA      180

AGGAAATCTG TTCATTCTTC TCATTCATAT AGTTATATCA AGTACTACCT TGCATATTGA      240

GAGGTTTTTC TTCTCTATTT ACACATATAT TTCCATGTGA ATTTGTATCA AACCTTTATT      300

TTCATGCAAA CTAGAAAATA ATGTTTCTTT TGCATAAGAG AAGAGAACAA TATAGCATTA      360

CAAAACTGCT CAAATTGTTT GTTAAGTTAT CCATTATAAT TAGTTGGCAG GAGCTAATAC      420

AAATCACATT TACGACAGCA ATAATAAAAC TGAAGTACCA GTTAAATATC CAAATAATT      480

AAAGGAACAT TTTTAGCCTG GGTATAATTA GCTAATTCAC TTTACAAGCA TTTATTAGAA      540

TGAATTCACA TGTTATTATT CCTAGCCCAA CACAATGG                              578

(2) INFORMATION FOR SEQ ID NO:105:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:105:

TTTTTTTTTT TTTTTCAGTA ATAATCAGAA CAATATTTAT TTTTATATTT AAAATTCATA       60

GAAAAGTGCC TTACATTTAA TAAAAGTTTG TTTCTCAAAG TGATCAGAGG AATTAGATAT      120

GTCTTGAACA CCAATATTAA TTTGAGGAAA ATACACCAAA ATACATTAAG TAAATTATTT      180

AAGATCATAG AGCTTGTAAG TGAAAAGATA AAATTTGACC TCAGAAACTC TGAGCATTAA      240

AAATCCACTA TTAGCAAATA AATTACTATG GACTTCTTGC TTTAATTTTG TGATGAATAT      300

GGGGTGTCAC TGGTAAACCA ACACATTCTG AAGGATACAT TACTTAGTGA TAGATTCTTA      360
```

```
TGTACTTTGC TAATACGTGG ATATGAGTTG ACAAGTTTCT CTTTCTTCAA TCTTTTAAGG        420

GGCGAGAAAT GAGGAAGAAA AGAAAAGGAT TACGCATACT GTTCTTTCTA TGGAAGGATT        480

AGATATGTTT CCTTTGCCAA TATTAAAAAA ATAATAATGT TTACTACTAG TGAAACCC         538
```

(2) INFORMATION FOR SEQ ID NO:106:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:106:

```
TTTTTTTTTT TTTTTTAGTC AAGTTTCTAT TTTTATTATA ATTAAAGTCT TGGTCATTTC         60

ATTTATTAGC TCTGCAACTT ACATATTTAA ATTAAAGAAA CGTTTTAGAC AACTGTACAA        120

TTTATAAATG TAAGGTGCCA TTATTGAGTA ATATATTCCT CCAAGAGTGG ATGTGTCCCT        180

TCTCCCACCA ACTAATGAAC AGCAACATTA GTTTAATTTT ATTAGTAGAT ATACACTGCT        240

GCAAACGCTA ATTCTCTTCT CCATCCCCAT GTGATATTGT GTATATGTGT GAGTTGGTAG        300

AATGCATCAC AATCTACAAT CAACAGCAAG ATGAAGCTAG GCTGGGCTTT CGGTGAAAAT        360

AGACTGTGTC TGTCTGAATC AAATGATCTG ACCTATCCTC GGTGGCAAGA ACTCTTCGAA        420

CCGCTTCCTC AAAGGCGCTG CCACATTTGT GGCTCTTTGC ACTTGTTTCA AAA              473
```

(2) INFORMATION FOR SEQ ID NO:107:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:107:

```
CGCCATGGCA CTGCAGGGCA TCTCGGTCAT GGAGCTGTCC GGCCTGGCCC CGGGCCCGTT         60

CTGTGCTATG GTCCTGGCTG ACTTCGGGGC GCGTGTGGTA CGCGTGGACC GGCCCGGCTC        120

CCGCTACGAC GTGAGCCGCT GGGCCGGGG CAAGCGCTCG CTAGTGCTGG ACCTGAAGCA         180

GCCGCGGGGA GCCGCCGTGC TGCGGCGTCT GTGCAAGCGG TCGGATGTGC TGCTGGAGCC        240

CTTCCGCCGC GGTGTCATGG AGAAACTCCA GCTGGGCCCA GAGATTCTGC AGCGGGAAAA        300

TCCAAGGCTT ATTTATGCCA GGCTGAGTGG ATTTGGCCAG TCAGGAAGCT TCTGCCGGTT        360

AGCTGGCCAC GATATCAACT ATTTGGCTTT GTCAGGTGTT CTCTCAAAAA TTGGCAGAAG        420

TGGTGAGAAT CCGTATGCCC CGCTGAATCT CCTGGCTGAC TTTGCTGGTG GTGGCCTTAT        480

GTGTGCACTG GCATTATAA TGGCTCTTTT TGACCGCACA CGCACTGACA AGGGTCAGGT         540

CATTGATGCA AATATGGTGG AAGGAACAGC ATATTTAAGT TCTTTTCTGT GGAAAACTCA        600

GAAATCGAGT CTGTGGGAAG CACCTCGAGG ACAGAACATG TTGGATGGTG GAGCACCTTT        660

CTATACGACT TACAGGACAG CAGATGGGGA ATTCATGGCT GTTGGAGCAA TAGAACCCCA        720

GTTCTACGAG CTGCTGATCA AAGGACTTGG ACTAAAGTCT GATGAACTTC CCAATCAGAT        780
```

```
GAGCATGGAT GATTGGCCAG AAATGAAGAA GAAGTTTGCA GATGTATTTG CAAAGAAGAC    840

GAAGGCAGAG TGGTGTCAAA TCTTTGACGG CACAGATGCC TGTGTGACTC CGGTTCTGAC    900

TTTTGAGGAG GTTGTTCATC ATGATCACAA CAAGGAACGG GGCTCGTTTA TCACCAGTGA    960

GGAGCAGGAC GTGAGCCCCC GCCCTGCACC TCTGCTGTTA AACACCCCAG CCATCCCTTC   1020

TTTCAAAAGG GATCCTTTCA TAGGAGAACA CACTGAGGAG ATACTTGAAG AATTTGGATT   1080

CAGCCGCGAA GAGATTTATC AGCTTAACTC AGATAAAATC ATTGAAAGTA ATAAGGTAAA   1140

AGCTAGTCTC TAACTTCCAG GCCCACGGCT CAAGTGAATT TGAATACTGC ATTTACAGTG   1200

TAGAGTAACA CATAACATTG TATGCATGGA AACATGGAGG AACAGTATTA CAGTGTCCTA   1260

CCACTCTAAT CAAGAAAAGA ATTACAGACT CTGATTCTAC AGTGATGATT GAATTCTAAA   1320

AATGGTTATC ATTAGGGCTT TTGATTTATA AAACTTTGGG TACTTATACT AAATTATGGT   1380

AGTTATTCTG CCTTCCAGTT TGCTTGATAT ATTTGTTGAT ATTAAGATTC TTGACTTATA   1440

TTTTGAATGG GTTCTAGTGA AAAAGGAATG ATATATTCTT GAAGACATCG ATATACATTT   1500

ATTTACACTC TTGATTCTAC AATGTAGAAA ATGAGGAAAT GCCACAAATT GTATGGTGAT   1560

AAAAGTCACG TGAAACAAAA AAAAAAAAAA AAAAAAAAAA AAAAAAAAAA AAAAAAAAA    1620

A                                                                  1621

(2) INFORMATION FOR SEQ ID NO:108:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:108:

Met Ala Leu Gln Gly Ile Ser Val Met Glu Leu Ser Gly Leu Ala Pro
1               5                   10                  15

Gly Pro Phe Cys Ala Met Val Leu Ala Asp Phe Gly Ala Arg Val Val
            20                  25                  30

Arg Val Asp Arg Pro Gly Ser Arg Tyr Asp Val Ser Arg Leu Gly Arg
        35                  40                  45

Gly Lys Arg Ser Leu Val Leu Asp Leu Lys Gln Pro Arg Gly Ala Ala
    50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Asp Lys
                165                 170                 175
```

```
Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
            195                 200                 205

Gly Gln Asn Met Leu Asp Gly Gly Ala Pro Phe Tyr Thr Thr Tyr Arg
            210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
            245                 250                 255

Asn Gln Met Ser Met Asp Asp Trp Pro Glu Met Lys Lys Lys Phe Ala
            260                 265                 270

Asp Val Phe Ala Lys Lys Thr Lys Ala Glu Trp Cys Gln Ile Phe Asp
            275                 280                 285

Gly Thr Asp Ala Cys Val Thr Pro Val Leu Thr Phe Glu Glu Val Val
            290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Leu Asn Thr Pro Ala
            325                 330                 335

Ile Pro Ser Phe Lys Arg Asp Pro Phe Ile Gly Glu His Thr Glu Glu
            340                 345                 350

Ile Leu Glu Glu Phe Gly Phe Ser Arg Glu Glu Ile Tyr Gln Leu Asn
            355                 360                 365

Ser Asp Lys Ile Ile Glu Ser Asn Lys Val Lys Ala Ser Leu
370                 375                 380

(2) INFORMATION FOR SEQ ID NO:109:

(i) SEQUENCE CHARACTERISTICS:
        (A) LENGTH: 1524 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:109:

GGCACGAGGC TGCGCCAGGG CCTGAGCGGA GGCGGGGGCA GCCTCGCCAG CGGGGGCCCC        60

GGGCCTGGCC ATGCCTCACT GAGCCAGCGC CTGCGCCTCT ACCTCGCCGA CAGCTGGAAC       120

CAGTGCGACC TAGTGGCTCT CACCTGCTTC CTCCTGGGCG TGGGCTGCCG GCTGACCCCG       180

GGTTTGTACC ACCTGGGCCG CACTGTCCTC TGCATCGACT TCATGGTTTT CACGGTGCGG       240

CTGCTTCACA TCTTCACGGT CAACAAACAG CTGGGGCCCA AGATCGTCAT CGTGAGCAAG       300

ATGATGAAGG ACGTGTTCTT CTTCCTCTTC TTCCTCGGCG TGTGGCTGGT AGCCTATGGC       360

GTGGCCACGG AGGGGCTCCT GAGGCCACGG GACAGTGACT TCCCAAGTAT CCTGCGCCGC       420

GTCTTCTACC GTCCCTACCT GCAGATCTTC GGGCAGATTC CCAGGAGGA CATGGACGTG        480

GCCCTCATGG AGCACAGCAA CTGCTCGTCG GAGCCCGGCT CTGGGCACA CCCTCCTGGG        540

GCCCAGGCGG CCACCTGCGT CTCCCAGTAT GCCAACTGGC TGGTGGTGCT GCTCCTCGTC       600

ATCTTCCTGC TCGTGGCCAA CATCCTGCTG GTCAACTTGC TCATTGCCAT GTTCAGTTAC       660

ACATTCGGCA AAGTACAGGG CAACAGCGAT CTCTACTGGA AGGCGCAGCG TTACCGCCTC       720
```

```
ATCCGGGAAT TCCACTCTCG GCCCGCGCTG GCCCCGCCCT TTATCGTCAT CTCCCACTTG        780

CGCCTCCTGC TCAGGCAATT GTGCAGGCGA CCCCGGAGCC CCCAGCCGTC CTCCCCGGCC        840

CTCGAGCATT TCCGGGTTTA CCTTTCTAAG GAAGCCGAGC GGAAGCTGCT AACGTGGGAA        900

TCGGTGCATA AGGAGAACTT TCTGCTGGCA CGCGCTAGGG ACAAGCGGGA GAGCGACTCC        960

GAGCGTCTGA AGCGCACGTC CCAGAAGGTG GACTTGGCAC TGAAACAGCT GGGACACATC       1020

CGCGAGTACG AACAGCGCCT GAAAGTGCTG GAGCGGGAGG TCCAGCAGTG TAGCCGCGTC       1080

CTGGGGTGGG TGGCCGAGGC CCTGAGCCGC TCTGCCTTGC TGCCCCCAGG TGGGCCGCCA       1140

CCCCCTGACC TGCCTGGGTC CAAAGACTGA GCCCTGCTGG CGGACTTCAA GGAGAAGCCC       1200

CCACAGGGGA TTTTGCTCCT AGAGTAAGGC TCATCTGGGC CTCGGCCCCC GCACCTGGTG       1260

GCCTTGTCCT TGAGGTGAGC CCCATGTCCA TCTGGGCCAC TGTCAGGACC ACCTTTGGGA       1320

GTGTCATCCT TACAAACCAC AGCATGCCCG GCTCCTCCCA GAACCAGTCC CAGCCTGGGA       1380

GGATCAAGGC CTGGATCCCG GGCCGTTATC CATCTGGAGG CTGCAGGGTC CTTGGGGTAA       1440

CAGGGACCAC AGACCCCTCA CCACTCACAG ATTCCTCACA CTGGGGAAAT AAAGCCATTT       1500

CAGAGGAAAA AAAAAAAAA AAAA                                              1524

(2) INFORMATION FOR SEQ ID NO:110:

(i) SEQUENCE CHARACTERISTICS:
        (A) LENGTH: 3410 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:110:

GGGAACCAGC CTGCACGCGC TGGCTCCGGG TGACAGCCGC GCGCCTCGGC CAGGATCTGA         60

GTGATGAGAC GTGTCCCCAC TGAGGTGCCC CACAGCAGCA GGTGTTGAGC ATGGGCTGAG        120

AAGCTGGACC GGCACCAAAG GGCTGGCAGA AATGGGCGCC TGGCTGATTC CTAGGCAGTT        180

GGCGGCAGCA AGGAGGAGAG GCCGCAGCTT CTGGAGCAGA GCCGAGACGA AGCAGTTCTG        240

GAGTGCCTGA ACGGCCCCCT GAGCCCTACC CGCCTGGCCC ACTATGGTCC AGAGGCTGTG        300

GGTGAGCCGC CTGCTGCGGC ACCGGAAAGC CCAGCTCTTG CTGGTCAACC TGCTAACCTT        360

TGGCCTGGAG GTGTGTTTGG CCGCAGGCAT CACCTATGTG CCGCCTCTGC TGCTGGAAGT        420

GGGGGTAGAG GAGAAGTTCA TGACCATGGT GCTGGGCATT GGTCCAGTGC TGGGCCTGGT        480

CTGTGTCCCG CTCCTAGGCT CAGCCAGTGA CCACTGGCGT GGACGCTATG GCCGCCGCCG        540

GCCCTTCATC TGGGCACTGT CCTTGGGCAT CCTGCTGAGC CTCTTTCTCA TCCCAAGGGC        600

CGGCTGGCTA GCAGGGCTGC TGTGCCCGGA TCCCAGGCCC CTGGAGCTGG CACTGCTCAT        660

CCTGGGCGTG GGGCTGCTGG ACTTCTGTGG CCAGGTGTGC TTCACTCCAC TGGAGGCCCT        720

GCTCTCTGAC CTCTTCCGGG ACCCGGACCA CTGTCGCCAG GCCTACTCTG TCTATGCCTT        780

CATGATCAGT CTTGGGGGCT GCCTGGGCTA CCTCCTGCCT GCCATTGACT GGGACACCAG        840

TGCCCTGGCC CCCTACCTGG GCACCCAGGA GGAGTGCCTC TTTGGCCTGC TCACCCTCAT        900

CTTCCTCACC TGCGTAGCAG CCACACTGCT GGTGGCTGAG GAGGCAGCGC TGGGCCCCAC        960

CGAGCCAGCA GAAGGGCTGT CGGCCCCCTC CTTGTCGCCC CACTGCTGTC CATGCCGGGC       1020
```

```
CCGCTTGGCT TTCCGGAACC TGGGCGCCCT GCTTCCCCGG CTGCACCAGC TGTGCTGCCG    1080

CATGCCCCGC ACCCTGCGCC GGCTCTTCGT GGCTGAGCTG TGCAGCTGGA TGGCACTCAT    1140

GACCTTCACG CTGTTTTACA CGGATTTCGT GGGCGAGGGG CTGTACCAGG GCGTGCCCAG    1200

AGCTGAGCCG GGCACCGAGG CCCGGAGACA CTATGATGAA GGCGTTCGGA TGGGCAGCCT    1260

GGGGCTGTTC CTGCAGTGCG CCATCTCCCT GGTCTTCTCT CTGGTCATGG ACCGGCTGGT    1320

GCAGCGATTC GGCACTCGAG CAGTCTATTT GGCCAGTGTG GCAGCTTTCC CTGTGGCTGC    1380

CGGTGCCACA TGCCTGTCCC ACAGTGTGGC CGTGGTGACA GCTTCAGCCG CCCTCACCGG    1440

GTTCACCTTC TCAGCCCTGC AGATCCTGCC CTACACACTG GCCTCCCTCT ACCACCGGGA    1500

GAAGCAGGTG TTCCTGCCCA AATACCGAGG GGACACTGGA GGTGCTAGCA GTGAGGACAG    1560

CCTGATGACC AGCTTCCTGC CAGGCCCTAA GCCTGGAGCT CCCTTCCCTA ATGGACACGT    1620

GGGTGCTGGA GGCAGTGGCC TGCTCCCACC TCCACCCGCG CTCTGCGGGG CCTCTGCCTG    1680

TGATGTCTCC GTACGTGTGG TGGTGGGTGA GCCCACCGAG GCCAGGGTGG TTCCGGGCCG    1740

GGGCATCTGC CTGGACCTCG CCATCCTGGA TAGTGCCTTC CTGCTGTCCC AGGTGGCCCC    1800

ATCCCTGTTT ATGGGCTCCA TTGTCCAGCT CAGCCAGTCT GTCACTGCCT ATATGGTGTC    1860

TGCCGCAGGC CTGGGTCTGG TCGCCATTTA CTTTGCTACA CAGGTAGTAT TTGACAAGAG    1920

CGACTTGGCC AAATACTCAG CGTAGAAAAC TTCCAGCACA TTGGGGTGGA GGGCCTGCCT    1980

CACTGGGTCC CAGCTCCCCG CTCCTGTTAG CCCCATGGGG CTGCCGGGCT GGCCGCCAGT    2040

TTCTGTTGCT GCCAAAGTAA TGTGGCTCTC TGCTGCCACC CTGTGCTGCT GAGGTGCGTA    2100

GCTGCACAGC TGGGGCTGG GGCGTCCCTC TCCTCTCTCC CCAGTCTCTA GGGCTGCCTG    2160

ACTGGAGGCC TTCCAAGGGG GTTTCAGTCT GGACTTATAC AGGGAGGCCA GAAGGGCTCC    2220

ATGCACTGGA ATGCGGGAC TCTGCAGGTG GATTACCCAG GCTCAGGGTT AACAGCTAGC    2280

CTCCTAGTTG AGACACACCT AGAGAAGGGT TTTTGGGAGC TGAATAAACT CAGTCACCTG    2340

GTTTCCCATC TCTAAGCCCC TTAACCTGCA GCTTCGTTTA ATGTAGCTCT TGCATGGGAG    2400

TTTCTAGGAT GAAACACTCC TCCATGGGAT TTGAACATAT GACTTATTTG TAGGGGAAGA    2460

GTCCTGAGGG GCAACACACA AGAACCAGGT CCCCTCAGCC ACAGCACTG TCTTTTTGCT     2520

GATCCACCCC CCTCTTACCT TTTATCAGGA TGTGGCCTGT TGGTCCTTCT GTTGCCATCA    2580

CAGAGACACA GGCATTTAAA TATTTAACTT ATTTATTTAA CAAAGTAGAA GGGAATCCAT    2640

TGCTAGCTTT TCTGTGTTGG TGTCTAATAT TTGGGTAGGG TGGGGATCC CCAACAATCA     2700

GGTCCCCTGA GATAGCTGGT CATTGGGCTG ATCATTGCCA GAATCTTCTT CTCCTGGGGT    2760

CTGGCCCCCC AAAATGCCTA ACCCAGGACC TTGGAAATTC TACTCATCCC AAATGATAAT    2820

TCCAAATGCT GTTACCCAAG GTTAGGGTGT TGAAGGAAGG TAGAGGGTGG GGCTTCAGGT    2880

CTCAACGGCT TCCCTAACCA CCCCTCTTCT CTTGGCCCAG CCTGGTTCCC CCCACTTCCA    2940

CTCCCCTCTA CTCTCTCTAG GACTGGGCTG ATGAAGGCAC TGCCCAAAAT TTCCCCTACC    3000

CCCAACTTTC CCCTACCCCC AACTTTCCCC ACCAGCTCCA CAACCCTGTT TGGAGCTACT    3060

GCAGGACCAG AAGCACAAAG TGCGGTTTCC CAAGCCTTTG TCCATCTCAG CCCCCAGAGT    3120

ATATCTGTGC TTGGGGAATC TCACACAGAA ACTCAGGAGC ACCCCTGCC TGAGCTAAGG     3180

GAGGTCTTAT CTCTCAGGGG GGGTTTAAGT GCCGTTTGCA ATAATGTCGT CTTATTTATT    3240

TAGCGGGGTG AATATTTTAT ACTGTAAGTG AGCAATCAGA GTATAATGTT TATGGTGACA    3300

AAATTAAAGG CTTTCTTATA TGTTTAAAAA AAAAAAAAA AAAAAAAAA AAAAAAAAA       3360

AAAAAAAARA AAAAAAAAA AAAAAAAAA AAAAAATAA AAAAAAAAA                   3410
```

(2) INFORMATION FOR SEQ ID NO:111:

(i) SEQUENCE CHARACTERISTICS:
        (A) LENGTH: 1289 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:111:

```
AGCCAGGCGT CCCTCTGCCT GCCCACTCAG TGGCAACACC CGGGAGCTGT TTTGTCCTTT    60
GTGGAGCCTC AGCAGTTCCC TCTTTCAGAA CTCACTGCCA AGAGCCCTGA ACAGGAGCCA   120
CCATGCAGTG CTTCAGCTTC ATTAAGACCA TGATGATCCT CTTCAATTTG CTCATCTTTC   180
TGTGTGGTGC AGCCCTGTTG GCAGTGGGCA TCTGGGTGTC AATCGATGGG GCATCCTTTC   240
TGAAGATCTT CGGGCCACTG TCGTCCAGTG CCATGCAGTT TGTCAACGTG GGCTACTTCC   300
TCATCGCAGC CGGCGTTGTG GTCTTTGCTC TTGGTTTCCT GGGCTGCTAT GGTGCTAAGA   360
CTGAGAGCAA GTGTGCCCTC GTGACGTTCT TCTTCATCCT CCTCCTCATC TTCATTGCTG   420
AGGTTGCAGC TGCTGTGGTC GCCTTGGTGT ACACCACAAT GGCTGAGCAC TTCCTGACGT   480
TGCTGGTAGT GCCTGCCATC AAGAAAGATT ATGGTTCCCA GGAAGACTTC ACTCAAGTGT   540
GGAACACCAC CATGAAAGGG CTCAAGTGCT GTGGCTTCAC CAACTATACG GATTTTGAGG   600
ACTCACCCTA CTTCAAAGAG AACAGTGCCT TTCCCCCATT CTGTTGCAAT GACAACGTCA   660
CCAACACAGC CAATGAAACC TGCACCAAGC AAAAGGCTCA CGACCAAAAA GTAGAGGGTT   720
GCTTCAATCA GCTTTTGTAT GACATCCGAA CTAATGCAGT CACCGTGGGT GGTGTGGCAG   780
CTGGAATTGG GGGCCTCGAG CTGGCTGCCA TGATTGTGTC CATGTATCTG TACTGCAATC   840
TACAATAAGT CCACTTCTGC CTCTGCCACT ACTGCTGCCA CATGGGAACT GTGAAGAGGC   900
ACCCTGGCAA GCAGCAGTGA TTGGGGGAGG GGACAGGATC TAACAATGTC ACTTGGGCCA   960
GAATGGACCT GCCCTTTCTG CTCCAGACTT GGGGCTAGAT AGGGACCACT CCTTTTAGCG  1020
ATGCCTGACT TTCCTTCCAT TGGTGGGTGG ATGGGTGGGG GGCATTCCAG AGCCTCTAAG  1080
GTAGCCAGTT CTGTTGCCCA TTCCCCCAGT CTATTAAACC CTTGATATGC CCCCTAGGCC  1140
TAGTGGTGAT CCCAGTGCTC TACTGGGGGA TGAGAGAAAG GCATTTTATA GCCTGGGCAT  1200
AAGTGAAATC AGCAGAGCCT CTGGGTGGAT GTGTAGAAGG CACTTCAAAA TGCATAAACC  1260
TGTTACAATG TTAAAAAAAA AAAAAAAA                                    1289
```

(2) INFORMATION FOR SEQ ID NO:112:

(i) SEQUENCE CHARACTERISTICS:
        (A) LENGTH: 315 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:112:

```
Met Val Phe Thr Val Arg Leu Leu His Ile Phe Thr Val Asn Lys Gln
1               5                   10                  15
```

-continued

```
Leu Gly Pro Lys Ile Val Ile Val Ser Lys Met Met Lys Asp Val Phe
             20              25              30

Phe Phe Leu Phe Phe Leu Gly Val Trp Leu Val Ala Tyr Gly Val Ala
         35              40              45

Thr Glu Gly Leu Leu Arg Pro Arg Asp Ser Asp Phe Pro Ser Ile Leu
     50              55              60

Arg Arg Val Phe Tyr Arg Pro Tyr Leu Gln Ile Phe Gly Gln Ile Pro
 65              70              75              80

Gln Glu Asp Met Asp Val Ala Leu Met Glu His Ser Asn Cys Ser Ser
             85              90              95

Glu Pro Gly Phe Trp Ala His Pro Pro Gly Ala Gln Ala Gly Thr Cys
            100             105             110

Val Ser Gln Tyr Ala Asn Trp Leu Val Val Leu Leu Val Ile Phe
            115             120             125

Leu Leu Val Ala Asn Ile Leu Leu Val Asn Leu Leu Ile Ala Met Phe
        130             135             140

Ser Tyr Thr Phe Gly Lys Val Gln Gly Asn Ser Asp Leu Tyr Trp Lys
145             150             155             160

Ala Gln Arg Tyr Arg Leu Ile Arg Glu Phe His Ser Arg Pro Ala Leu
            165             170             175

Ala Pro Pro Phe Ile Val Ile Ser His Leu Arg Leu Leu Leu Arg Gln
            180             185             190

Leu Cys Arg Arg Pro Arg Ser Pro Gln Pro Ser Ser Pro Ala Leu Glu
        195             200             205

His Phe Arg Val Tyr Leu Ser Lys Glu Ala Glu Arg Lys Leu Leu Thr
    210             215             220

Trp Glu Ser Val His Lys Glu Asn Phe Leu Leu Ala Arg Ala Arg Asp
225             230             235             240

Lys Arg Glu Ser Asp Ser Glu Arg Leu Lys Arg Thr Ser Gln Lys Val
            245             250             255

Asp Leu Ala Leu Lys Gln Leu Gly His Ile Arg Glu Tyr Glu Gln Arg
        260             265             270

Leu Lys Val Leu Glu Arg Glu Val Gln Gln Cys Ser Arg Val Leu Gly
    275             280             285

Trp Val Ala Glu Ala Leu Ser Arg Ser Ala Leu Leu Pro Pro Gly Gly
        290             295             300

Pro Pro Pro Pro Asp Leu Pro Gly Ser Lys Asp
305             310             315
```

(2) INFORMATION FOR SEQ ID NO:113:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:113:

```
Met Val Gln Arg Leu Trp Val Ser Arg Leu Leu Arg His Arg Lys Ala
 1               5              10              15

Gln Leu Leu Leu Val Asn Leu Leu Thr Phe Gly Leu Glu Val Cys Leu
             20              25              30
```

```
Ala Ala Gly Ile Thr Tyr Val Pro Pro Leu Leu Glu Val Gly Val
         35                  40                  45
Glu Glu Lys Phe Met Thr Met Val Leu Gly Ile Gly Pro Val Leu Gly
 50                  55                  60
Leu Val Cys Val Pro Leu Gly Ser Ala Ser Asp His Trp Arg Gly
 65                  70                  75                  80
Arg Tyr Gly Arg Arg Pro Phe Ile Trp Ala Leu Ser Leu Gly Ile
             85                  90                  95
Leu Leu Ser Leu Phe Leu Ile Pro Arg Ala Gly Trp Leu Ala Gly Leu
             100                 105                 110
Leu Cys Pro Asp Pro Arg Pro Leu Glu Leu Ala Leu Leu Ile Leu Gly
         115                 120                 125
Val Gly Leu Leu Asp Phe Cys Gly Gln Val Cys Phe Thr Pro Leu Glu
 130                 135                 140
Ala Leu Leu Ser Asp Leu Phe Arg Asp Pro Asp His Cys Arg Gln Ala
145                 150                 155                 160
Tyr Ser Val Tyr Ala Phe Met Ile Ser Leu Gly Gly Cys Leu Gly Tyr
             165                 170                 175
Leu Leu Pro Ala Ile Asp Trp Asp Thr Ser Ala Leu Ala Pro Tyr Leu
             180                 185                 190
Gly Thr Gln Glu Glu Cys Leu Phe Gly Leu Leu Thr Leu Ile Phe Leu
         195                 200                 205
Thr Cys Val Ala Ala Thr Leu Leu Val Ala Glu Glu Ala Ala Leu Gly
 210                 215                 220
Pro Thr Glu Pro Ala Glu Gly Leu Ser Ala Pro Ser Leu Ser Pro His
225                 230                 235                 240
Cys Cys Pro Cys Arg Ala Arg Leu Ala Phe Arg Asn Leu Gly Ala Leu
             245                 250                 255
Leu Pro Arg Leu His Gln Leu Cys Cys Arg Met Pro Arg Thr Leu Arg
             260                 265                 270
Arg Leu Phe Val Ala Glu Leu Cys Ser Trp Met Ala Leu Met Thr Phe
         275                 280                 285
Thr Leu Phe Tyr Thr Asp Phe Val Gly Glu Gly Leu Tyr Gln Gly Val
 290                 295                 300
Pro Arg Ala Glu Pro Gly Thr Glu Ala Arg Arg His Tyr Asp Glu Gly
305                 310                 315                 320
Val Arg Met Gly Ser Leu Gly Leu Phe Leu Gln Cys Ala Ile Ser Leu
             325                 330                 335
Val Phe Ser Leu Val Met Asp Arg Leu Val Gln Arg Phe Gly Thr Arg
             340                 345                 350
Ala Val Tyr Leu Ala Ser Val Ala Ala Phe Pro Val Ala Ala Gly Ala
         355                 360                 365
Thr Cys Leu Ser His Ser Val Ala Val Val Thr Ala Ser Ala Ala Leu
 370                 375                 380
Thr Gly Phe Thr Phe Ser Ala Leu Gln Ile Leu Pro Tyr Thr Leu Ala
385                 390                 395                 400
Ser Leu Tyr His Arg Glu Lys Gln Val Phe Leu Pro Lys Tyr Arg Gly
             405                 410                 415
Asp Thr Gly Gly Ala Ser Ser Glu Asp Ser Leu Met Thr Ser Phe Leu
             420                 425                 430
Pro Gly Pro Lys Pro Gly Ala Pro Phe Pro Asn Gly His Val Gly Ala
         435                 440                 445
```

```
Gly Gly Ser Gly Leu Leu Pro Pro Pro Ala Leu Cys Gly Ala Ser
    450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
                500                 505                 510

Ile Val Gln Leu Ser Gln Ser Val Thr Ala Tyr Met Val Ser Ala Ala
                515                 520                 525

Gly Leu Gly Leu Val Ala Ile Tyr Phe Ala Thr Gln Val Val Phe Asp
                530                 535                 540

Lys Ser Asp Leu Ala Lys Tyr Ser Ala
545                 550
```

(2) INFORMATION FOR SEQ ID NO:114:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:114:

```
Met Gln Cys Phe Ser Phe Ile Lys Thr Met Met Ile Leu Phe Asn Leu
1                   5                   10                  15

Leu Ile Phe Leu Cys Gly Ala Ala Leu Ala Val Gly Ile Trp Val
                20                  25                  30

Ser Ile Asp Gly Ala Ser Phe Leu Lys Ile Phe Gly Pro Leu Ser Ser
        35                  40                  45

Ser Ala Met Gln Phe Val Asn Val Gly Tyr Phe Leu Ile Ala Ala Gly
50                  55                  60

Val Val Val Phe Ala Leu Gly Phe Leu Gly Cys Tyr Gly Ala Lys Thr
65                  70                  75                  80

Glu Ser Lys Cys Ala Leu Val Thr Phe Phe Ile Leu Leu Leu Ile
                85                  90                  95

Phe Ile Ala Glu Val Ala Ala Ala Val Val Ala Leu Val Tyr Thr Thr
                100                 105                 110

Met Ala Glu His Phe Leu Thr Leu Leu Val Val Pro Ala Ile Lys Lys
                115                 120                 125

Asp Tyr Gly Ser Gln Glu Asp Phe Thr Gln Val Trp Asn Thr Thr Met
                130                 135                 140

Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
                165                 170                 175

Asp Asn Val Thr Asn Thr Ala Asn Glu Thr Cys Thr Lys Gln Lys Ala
                180                 185                 190

His Asp Gln Lys Val Glu Gly Cys Phe Asn Gln Leu Leu Tyr Asp Ile
                195                 200                 205

Arg Thr Asn Ala Val Thr Val Gly Gly Val Ala Ala Gly Ile Gly Gly
                210                 215                 220
```

```
Leu Glu Leu Ala Ala Met Ile Val Ser Met Tyr Leu Tyr Cys Asn Leu
225                 230                 235                 240
Gln
```

(2) INFORMATION FOR SEQ ID NO:115:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO:115:

```
GCTCTTTCTC TCCCCTCCTC TGAATTTAAT TCTTTCAACT TGCAATTTGC AAGGATTACA      60

CATTTCACTG TGATGTATAT TGTGTTGCAA AAAAAAAAAA GTGTCTTTGT TTAAAATTAC     120

TTGGTTTGTG AATCCATCTT GCTTTTTCCC CATTGGAACT AGTCATTAAC CCATCTCTGA     180

ACTGGTAGAA AAACATCTGA AGAGCTAGTC TATCAGCATC TGACAGGTGA ATTGGATGGT     240

TCTCAGAACC ATTTCACCCA GACAGCCTGT TTCTATCCTG TTTAATAAAT TAGTTTGGGT     300

TCTCTACATG CATAACAAAC CCTGCTCCAA TCTGTCACAT AAAAGTCTGT GACTTGAAGT     360

TTAGTC                                                                366
```

(2) INFORMATION FOR SEQ ID NO:116:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:116:

```
ACAAAGATGA ACCATTTCCT ATATTATAGC AAAATTAAAA TCTACCCGTA TTCTAATATT      60

GAGAAATGAG ATNAAACACA ATNTTATAAA GTCTACTTAG AGAAGATCAA GTGACCTCAA     120

AGACTTTACT ATTTTCATAT TTTAAGACAC ATGATTTATC CTATTTTAGT AACCTGGTTC     180

ATACGTTAAA CAAAGGATAA TGTGAACAGC AGAGAGGATT TGTTGGCAGA AAATCTATGT     240

TCAATCTNGA ACTATCTANA TCACAGACAT TTCTATTCCT TT                       282
```

(2) INFORMATION FOR SEQ ID NO:117:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:117:

```
ACACATGTCG CTTCACTGCC TTCTTAGATG CTTCTGGTCA ACATANAGGA ACAGGGACCA      60
```

-continued

```
TATTTATCCT CCCTCCTGAA ACAATTGCAA AATAANACAA AATATATGAA ACAATTGCAA        120

AATAAGGCAA AATATATGAA ACAACAGGTC TCGAGATATT GGAAATCAGT CAATGAAGGA        180

TACTGATCCC TGATCACTGT CCTAATGCAG GATGTGGGAA ACAGATGAGG TCACCTCTGT        240

GACTGCCCCA GCTTACTGCC TGTAGAGAGT TTCTANGCTG CAGTTCAGAC AGGGAGAAAT        300

TGGGT                                                                    305
```

(2) INFORMATION FOR SEQ ID NO:118:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:118:

```
ACCAAGGTGT NTGAATCTCT GACGTGGGGA TCTCTGATTC CCGCACAATC TGAGTGGAAA         60

AANTCCTGGG T                                                              71
```

(2) INFORMATION FOR SEQ ID NO:119:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:119:

```
ACTCCGGTTG GTGTCAGCAG CACGTGGCAT TGAACATNGC AATGTGGAGC CCAAACCACA         60

GAAAATGGGG TGAAATTGGC CAACTTTCTA TNAACTTATG TTGGCAANTT TGCCACCAAC        120

AGTAAGCTGG CCCTTCTAAT AAAAGAAAAT TGAAAGGTTT CTCACTAANC GGAATTAANT        180

AATGGANTCA AGANACTCCC AGGCCTCAGC GT                                      212
```

(2) INFORMATION FOR SEQ ID NO:120:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:120:

```
ACTCGTTGCA NATCAGGGGC CCCCCAGAGT CACCGTTGCA GGAGTCCTTC TGGTCTTGCC         60

CTCCGCCGGC GCAGAACATG CTGGGGTGGT                                          90
```

(2) INFORMATION FOR SEQ ID NO:121:

(i) SEQUENCE CHARACTERISTICS:
        (A) LENGTH: 218 base pairs

```
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:121:

TGTANCGTGA ANACGACAGA NAGGGTTGTC AAAAATGGAG AANCCTTGAA GTCATTTTGA        60

GAATAAGATT TGCTAAAAGA TTTGGGGCTA AAACATGGTT ATTGGGAGAC ATTTCTGAAG       120

ATATNCANGT AAATTANGGA ATGAATTCAT GGTTCTTTTG GGAATTCCTT TACGATNGCC       180

AGCATANACT TCATGTGGGG ATANCAGCTA CCCTTGTA                              218

(2) INFORMATION FOR SEQ ID NO:122:

(i) SEQUENCE CHARACTERISTICS:
            (A) LENGTH: 171 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:122:

TAGGGGTGTA TGCAACTGTA AGGACAAAAA TTGAGACTCA ACTGGCTTAA CCAATAAAGG        60

CATTTGTTAG CTCATGGAAC AGGAAGTCGG ATGGTGGGGC ATCTTCAGTG CTGCATGAGT       120

CACCACCCCG GCGGGGTCAT CTGTGCCACA GGTCCCTGTT GACAGTGCGG T                171

(2) INFORMATION FOR SEQ ID NO:123:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:123:

TGTAGCGTGA AGACNACAGA ATGGTGTGTG CTGTGCTATC CAGGAACACA TTTATTATCA        60

TTATCAANTA TTGTGT                                                       76

(2) INFORMATION FOR SEQ ID NO:124:

(i) SEQUENCE CHARACTERISTICS:
            (A) LENGTH: 131 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:124:

ACCTTTCCCC AAGGCCAATG TCCTGTGTGC TAACTGGCCG GCTGCAGGAC AGCTGCAATT        60
```

```
CAATGTGCTG GGTCATATGG AGGGGAGGAG ACTCTAAAAT AGCCAATTTT ATTCTCTTGG        120

TTAAGATTTG T                                                            131
```

(2) INFORMATION FOR SEQ ID NO:125:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:125:

```
ACTTTATCTA CTGGCTATGA AATAGATGGT GGAAAATTGC GTTACCAACT ATACCACTGG         60

CTTGAAAAAG AGGTGATAGC TCTTCAGAGG ACTTGTGACT TTTGCTCAGA TGCTGAAGAA        120

CTACAGTCTG CATTTGGCAG AAATGAAGAT GAATTTGGAT TAAATGAGGA TGCTGAAGAT        180

TTGCCTCACC AAACAAAAGT GAAACAACTG AGAGAAAATT TTCAGGAAAA AAGACAGTGG        240

CTCTTGAAGT ATCAGTCACT TTTGAGAATG TTTCTTAGTT ACTGCATACT TCATGGATCC        300

CATGGTGGGG GTCTTGCATC TGTAAGAATG GAATTGATTT TGCTTTTGCA AGAATCTCAG        360

CAGGAAACAT CAGAACCACT ATTTTCTAGC CCTCTGTCAG AGCAAACCTC AGTGCCTCTC        420

CTCTTTGCTT GT                                                           432
```

(2) INFORMATION FOR SEQ ID NO:126:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:126:

```
ACACAACTTG AATAGTAAAA TAGAAACTGA GCTGAAATTT CTAATTCACT TTCTAACCAT         60

AGTAAGAATG ATATTTCCCC CCAGGGATCA CCAAATATTT ATAAAAATTT GT                112
```

(2) INFORMATION FOR SEQ ID NO:127:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:127:

```
ACCACGAAAC CACAAACAAG ATGGAAGCAT CAATCCACTT GCCAAGCACA GCAG              54
```

(2) INFORMATION FOR SEQ ID NO:128:

(i) SEQUENCE CHARACTERISTICS:
        (A) LENGTH: 323 base pairs (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:128:

```
ACCTCATTAG TAATTGTTTT GTTGTTTCAT TTTTTTCTAA TGTCTCCCCT CTACCAGCTC      60

ACCTGAGATA ACAGAATGAA AATGGAAGGA CAGCCAGATT TCTCCTTTGC TCTCTGCTCA     120

TTCTCTCTGA AGTCTAGGTT ACCCATTTTG GGGACCCATT ATAGGCAATA AACACAGTTC     180

CCAAAGCATT TGGACAGTTT CTTGTTGTGT TTTAGAATGG TTTTCCTTTT TCTTAGCCTT     240

TTCCTGCAAA AGGCTCACTC AGTCCCTTGC TTGCTCAGTG GACTGGGCTC CCCAGGGCCT     300

AGGCTGCCTT CTTTTCCATG TCC                                             323
```

(2) INFORMATION FOR SEQ ID NO:129:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:129:

```
ACATACATGT GTGTATATTT TTAAATATCA CTTTTGTATC ACTCTGACTT TTTAGCATAC      60

TGAAAACACA CTAACATAAT TTNTGTGAAC CATGATCAGA TACAACCCAA ATCATTCATC     120

TAGCACATTC ATCTGTGATA NAAAGATAGG TGAGTTTCAT TTCCTTCACG TTGGCCAATG     180

GATAAACAAA GT                                                         192
```

(2) INFORMATION FOR SEQ ID NO:130:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:130:

```
CCCTTTTTTA TGGAATGAGT AGACTGTATG TTTGAANATT TANCCACAAC CTCTTTGACA      60

TATAATGACG CAACAAAAAG GTGCTGTTTA GTCCTATGGT TCAGTTTATG CCCCTGACAA     120

GTTTCCATTG TGTTTTGCCG ATCTTCTGGC TAATCGTGGT ATCCTCCATG TTATTAGTAA     180

TTCTGTATTC CATTTTGTTA ACGCCTGGTA GATGTAACCT GCTANGAGGC TAACTTTATA     240

CTTATTTAAA AGCTCTTATT TTGTGGTCAT TAAAATGGCA ATTTATGTGC AGCACTTTAT     300

TGCAGCAGGA AGCACGTGTG GGTTGGTTGT AAAGCTCTTT GCTAATCTTA AAAAGTAATG     360

GG                                                                    362
```

(2) INFORMATION FOR SEQ ID NO:131:

```
    (i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:131:

CTTTTTGAAA GATCGTGTCC ACTCCTGTGG ACATCTTGTT TTAATGGAGT TTCCCATGCA      60

GTANGACTGG TATGGTTGCA GCTGTCCAGA TAAAAACATT TGAAGAGCTC CAAAATGAGA     120

GTTCTCCCAG GTTCGCCCTG CTGCTCCAAG TCTCAGCAGC AGCCTCTTTT AGGAGGCATC     180

TTCTGAACTA GATTAAGGCA GCTTGTAAAT CTGATGTGAT TTGGTTTATT ATCCAACTAA     240

CTTCCATCTG TTATCACTGG AGAAAGCCCA GACTCCCCAN GACNGGTACG GATTGTGGGC     300

ATANAAGGAT TGGGTGAAGC TGGCGTTGTG GT                                   332

(2) INFORMATION FOR SEQ ID NO:132:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:132:

ACTTTTGCCA TTTTGTATAT ATAAACAATC TTGGGACATT CTCCTGAAAA CTAGGTGTCC      60

AGTGGCTAAG AGAACTCGAT TTCAAGCAAT TCTGAAAGGA AAACCAGCAT GACACAGAAT     120

CTCAAATTCC CAAACAGGGG CTCTGTGGGA AAAATGAGGG AGGACCTTTG TATCTCGGGT     180

TTTAGCAAGT TAAAATGAAN ATGACAGGAA AGGCTTATTT ATCAACAAAG AGAAGAGTTG     240

GGATGCTTCT AAAAAAAACT TGGTAGAGA AAATAGGAAT GCTNAATCCT AGGGAAGCCT      300

GTAACAATCT ACAATTGGTC CA                                              322

(2) INFORMATION FOR SEQ ID NO:133:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:133:

ACAAGCCTTC ACAAGTTTAA CTAAATTGGG ATTAATCTTT CTGTANTTAT CTGCATAATT      60

CTTGTTTTTC TTTCCATCTG GCTCCTGGGT TGACAATTTG TGGAAACAAC TCTATTGCTA     120

CTATTTAAAA AAAATCACAA ATCTTTCCCT TTAAGCTATG TTNAATTCAA ACTATTCCTG     180

CTATTCCTGT TTTGTCAAAG AAATTATATT TTTCAAAATA TGTNTATTTG TTTGATGGGT     240

CCCACGAAAC ACTAATAAAA ACCACAGAGA CCAGCCTG                             278
```

(2) INFORMATION FOR SEQ ID NO:134:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:134:

```
GTTTANAAAA CTTGTTTAGC TCCATAGAGG AAAGAATGTT AAACTTTGTA TTTTAAAACA      60
TGATTCTCTG AGGTTAAACT TGGTTTTCAA ATGTTATTTT TACTTGTATT TTGCTTTTGG     120
T                                                                    121
```

(2) INFORMATION FOR SEQ ID NO:135:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:135:

```
ACTTANAACC ATGCCTAGCA CATCAGAATC CCTCAAAGAA CATCAGTATA ATCCTATACC      60
ATANCAAGTG GTGACTGGTT AAGCGTGCGA CAAAGGTCAG CTGGCACATT ACTTGTGTGC     120
AAACTTGATA CTTTTGTTCT AAGTAGGAAC TAGTATACAG TNCCTAGGAN TGGTACTCCA     180
GGGTGCCCCC CAACTCCTGC AGCCGCTCCT CTGTGCCAGN CCCTGNAAGG AACTTTCGCT     240
CCACCTCAAT CAAGCCCTGG GCCATGCTAC CTGCAATTGG CTGAACAAAC GTTTGCTGAG     300
TTCCCAAGGA TGCAAAGCCT GGTGCTCAAC TCCTGGGGCG TCAACTCAGT                350
```

(2) INFORMATION FOR SEQ ID NO:136:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:136:

```
TGTACCGTGA AGACGACAGA AGTTGCATGG CAGGGACAGG GCAGGGCCGA GGCCAGGGTT      60
GCTGTGATTG TATCCGAATA NTCCTCGTGA GAAAAGATAA TGAGATGACG TGAGCAGCCT     120
GCAGACTTGT GTCTGCCTTC AANAAGCCAG ACAGGAAGGC CCTGCCTGCC TTGGCTCTGA     180
CCTGGCGGCC AGCCAGCCAG CCACAGGTGG GCTTCTTCCT TTTGTGGTGA CAACNCCAAG     240
AAAACTGCAG AGGCCCAGGG TCAGGTGTNA GTGGGTANGT GACCATAAAA CACCAGGTGC     300
TCCCAGGAAC CCGGGCAAAG GCCATCCCCA CCTACAGCCA GCATGCCCAC TGGCGTGATG     360
```

```
GGTGCAGANG GATGAAGCAG CCAGNTGTTC TGCTGTGGT                          399
```

(2) INFORMATION FOR SEQ ID NO:137:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:137:

```
ACTGGTGTGG TNGGGGGTGA TGCTGGTGGT ANAAGTTGAN GTGACTTCAN GATGGTGTGT    60

GGAGGAAGTG TGTGAACGTA GGGATGTAGA NGTTTTGGCC GTGCTAAATG AGCTTCGGGA   120

TTGGCTGGTC CCACTGGTGG TCACTGTCAT TGGTGGGGTT CCTGT                   165
```

(2) INFORMATION FOR SEQ ID NO:138:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:138:

```
ACTCACTGGA ATGCCACATT CACAACAGAA TCAGAGGTCT GTGAAAACAT TAATGGCTCC    60

TTAACTTCTC CAGTAAGAAT CAGGGACTTG AAATGGAAAC GTTAACAGCC ACATGCCCAA   120

TGCTGGGCAG TCTCCCATGC CTTCCACAGT GAAAGGGCTT GAGAAAAATC ACATCCAATG   180

TCATGTGTTT CCAGCCACAC CAAAAGGTGC TTGGGGTGGA GGGCTGGGGG CATANANGGT   240

CANGCCTCAG GAAGCCTCAA GTTCCATTCA GCTTTGCCAC TGTACATTCC CCATNTTTAA   300

AAAAACTGAT GCCTTTTTTT TTTTTTTTTG TAAAATTC                           338
```

(2) INFORMATION FOR SEQ ID NO:139:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:139:

```
GGGAATCTTG GTTTTGGCA TCTGGTTTGC CTATAGCCGA GGCCACTTTG ACAGAACAAA     60

GAAAGGGACT TCGAGTAAGA AGGTGATTTA CAGCCAGCCT AGTGCCCGAA GTGAAGGAGA   120

ATTCAAACAG ACCTCGTCAT TCCTGGTGTG AGCCTGGTCG GCTCACCGCC TATCATCTGC   180

ATTTGCCTTA CTCAGGTGCT ACCGGACTCT GGCCCCTGAT GTCTGTAGTT TCACAGGATG   240

CCTTATTTGT CTTCTACACC CCACAGGGCC CCTACTTCT TCGGATGTGT TTTTAATAAT    300

GTCAGCTATG TGCCCCATCC TCCTTCATGC CCTCCCTCCC TTTCCTACCA CTGCTGAGTG   360
```

```
GCCTGGAACT TGTTTAAAGT GT                                          382

(2) INFORMATION FOR SEQ ID NO:140:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:140:

ACCAAANCTT CTTTCTGTTG TGTTNGATTT TACTATAGGG GTTTNGCTTN TTCTAAANAT    60

ACTTTTCATT TAACANCTTT TGTTAAGTGT CAGGCTGCAC TTTGCTCCAT ANAATTATTG   120

TTTTCACATT TCAACTTGTA TGTGTTTGTC TCTTANAGCA TTGGTGAAAT CACATATTTT   180

ATATTCAGCA TAAAGGAGAA                                              200

(2) INFORMATION FOR SEQ ID NO:141:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:141:

ACTTTATTTT CAAAACACTC ATATGTTGCA AAAAACACAT AGAAAAATAA AGTTTGGTGG    60

GGGTGCTGAC TAAACTTCAA GTCACAGACT TTTATGTGAC AGATTGGAGC AGGGTTTGTT   120

ATGCATGTAG AGAACCCAAA CTAATTTATT AAACAGGATA GAAACAGGCT GTCTGGGTGA   180

AATGGTTCTG AGAACCATCC AATTCACCTG TCAGATGCTG ATANACTAGC TCTTCAGATG   240

TTTTTCTACC AGTTCAGAGA TNGGTTAATG ACTANTTCCA ATGGGAAAA AGCAAGATGG    300

ATTCACAAAC CAAGTAATTT TAAACAAAGA CACTT                             335

(2) INFORMATION FOR SEQ ID NO:142:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:142:

ACCAGGTTAA TATTGCCACA TATATCCTTT CCAATTGCGG GCTAAACAGA CGTGTATTTA    60

GGGTTGTTTA AAGACAACCC AGCTTAATAT CAAGAGAAAT TGTGACCTTT CATGGAGTAT   120

CTGATGGAGA AAACACTGAG TTTTGACAAA TCTTATTTTA TTCAGATAGC AGTCTGATCA   180

CACATGGTCC AACAACACTC AAATAATAAA TCAAATATNA TCAGATGTTA AAGATTGGTC   240
```

```
TTCAAACATC ATAGCCAATG ATGCCCCGCT TGCCTATAAT CTCTCCGACA TAAAACCACA    300

TCAACACCTC AGTGGCCACC AAACCATTCA GCACAGCTTC CTTAACTGTG AGCTGTTTGA    360

AGCTACCAGT CTGAGCACTA TTGACTATNT TTTTCANGCT CTGAATAGCT CTAGGGATCT    420

CAGCANGGGT GGGAGGAACC AGCTCAACCT TGGCGTANT                           459
```

(2) INFORMATION FOR SEQ ID NO:143:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:143:

```
ACATTTCCTT CCACCAAGTC AGGACTCCTG GCTTCTGTGG GAGTTCTTAT CACCTGAGGG     60

AAATCCAAAC AGTCTCTCCT AGAAAGGAAT AGTGTCACCA ACCCCACCCA TCTCCCTGAG    120

ACCATCCGAC TTCCCTGTGT                                                140
```

(2) INFORMATION FOR SEQ ID NO:144:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:144:

```
ACTTCAGTAA CAACATACAA TAACAACATT AAGTGTATAT TGCCATCTTT GTCATTTTCT     60

ATCTATACCA CTCTCCCTTC TGAAAACAAN AATCACTANC CAATCACTTA TACAAATTTG    120

AGGCAATTAA TCCATATTTG TTTTCAATAA GGAAAAAAAG ATGT                     164
```

(2) INFORMATION FOR SEQ ID NO:145:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:145:

```
ACGTAGACCA TCCAACTTTG TATTTGTAAT GGCAAACATC CAGNAGCAAT TCCTAAACAA     60

ACTGGAGGGT ATTTATACCC AATTATCCCA TTCATTAACA TGCCCTCCTC CTCAGGCTAT    120

GCAGGACAGC TATCATAAGT CGGCCCAGGC ATCCAGATAC TACCATTTGT ATAAACTTCA    180

GTAGGGGAGT CCATCCAAGT GACAGGTCTA ATCAAAGGAG GAAATGGAAC ATAAGCCCAG    240

TAGTAAAATN TTGCTTAGCT GAAACAGCCA CAAAAGACTT ACCGCCGTGG TGATTACCAT    300

CAA                                                                  303
```

(2) INFORMATION FOR SEQ ID NO:146:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:146:

```
ACTGCAGCTC AATTAGAAGT GGTCTCTGAC TTTCATCANC TTCTCCCTGG GCTCCATGAC      60

ACTGGCCTGG AGTGACTCAT TGCTCTGGTT GGTTGAGAGA GCTCCTTTGC CAACAGGCCT     120

CCAAGTCAGG GCTGGGATTT GTTTCCTTTC CACATTCTAG CAACAATATG CTGGCCACTT     180

CCTGAACAGG GAGGGTGGGA GGAGCCAGCA TGGAACAAGC TGCCACTTTC TAAAGTAGCC     240

AGACTTGCCC CTGGGCCTGT CACACCTACT GATGACCTTC TGTGCCTGCA GGATGGAATG     300

TAGGGGTGAG CTGTGTGACT CTATGGT                                        327
```

(2) INFORMATION FOR SEQ ID NO:147:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:147:

```
ACATTGTTTT TTTGAGATAA AGCATTGANA GAGCTCTCCT TAACGTGACA CAATGGAAGG      60

ACTGGAACAC ATACCCACAT CTTTGTTCTG AGGGATAATT TTCTGATAAA GTCTTGCTGT     120

ATATTCAAGC ACATATGTTA TATATTATTC AGTTCCATGT TTATAGCCTA GTT            173
```

(2) INFORMATION FOR SEQ ID NO:148:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:148:

```
ACAACCACTT TATCTCATCG AATTTTTAAC CCAAACTCAC TCACTGTGCC TTTCTATCCT      60

ATGGGATATA TTATTTGATG CTCCATTTCA TCACACATAT ATGAATAATA CACTCATACT     120

GCCCTACTAC CTGCTGCAAT AATCACATTC CCTTCCTGTC CTGACCCTGA AGCCATTGGG     180

GTGGTCCTAG TGGCCATCAG TCCANGCCTG CACCTTGAGC CCTTGAGCTC CATTGCTCAC     240

NCCANCCCAC CTCACCGACC CCATCCTCTT ACACAGCTAC CTCCTTGCTC TCTAACCCCA     300

TAGATTATNT CCAAATTCAG TCAATTAAGT TACTATTAAC ACTCTACCCG ACATGTCCAG     360
```

```
CACCACTGGT AAGCCTTCTC CAGCCAACAC ACACACACAC ACACNCACAC ACACACATAT      420

CCAGGCACAG GCTACCTCAT CTTCACAATC ACCCCTTTAA TTACCATGCT ATGGTGG         477
```

(2) INFORMATION FOR SEQ ID NO:149:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:149:

```
ACAGTTGTAT TATAATATCA AGAAATAAAC TTGCAATGAG AGCATTTAAG AGGGAAGAAC       60

TAACGTATTT TAGAGAGCCA AGGAAGGTTT CTGTGGGGAG TGGGATGTAA GGTGGGGCCT      120

GATGATAAAT AAGAGTCAGC CAGGTAAGTG GGTGGTGTGG TATGGGCACA GTGAAGAACA      180

TTTCAGGCAG AGGGAACAGC AGTGAAA                                         207
```

(2) INFORMATION FOR SEQ ID NO:150:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:150:

```
ACCTTGATTT CATTGCTGCT CTGATGGAAA CCCAACTATC TAATTTAGCT AAAACATGGG       60

CACTTAAATG TGGTCAGTGT TTGGACTTGT TAACTANTGG CATCTTTGGG T              111
```

(2) INFORMATION FOR SEQ ID NO:151:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:151:

```
AGCGCGGCAG GTCATATTGA ACATTCCAGA TACCTATCAT TACTCGATGC TGTTGATAAC       60

AGCAAGATGG CTTTGAACTC AGGGTCACCA CCAGCTATTG GACCTTACTA TGAAAACCAT      120

GGATACCAAC CGGAAAACCC CTATCCCGCA CAGCCCACTG TGGTCCCCAC TGTCTACGAG      180

GTGCATCCGG CTCAGT                                                     196
```

(2) INFORMATION FOR SEQ ID NO:152:

(i) SEQUENCE CHARACTERISTICS:
        (A) LENGTH: 132 base pairs
        (B) TYPE: nucleic acid
        (C) STRANDEDNESS: single (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:152:

ACAGCACTTT CACATGTAAG AAGGGAGAAA TTCCTAAATG TAGGAGAAAG ATAACAGAAC      60

CTTCCCCTTT TCATCTAGTG GTGGAAACCT GATGCTTTAT GTTGACAGGA ATAGAACCAG     120

GAGGGAGTTT GT                                                        132

(2) INFORMATION FOR SEQ ID NO:153:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:153:

ACAANACCCA NGANAGGCCA CTGGCCGTGG TGTCATGGCC TCCAAACATG AAAGTGTCAG      60

CTTCTGCTCT TATGTCCTCA TCTGACAACT CTTTACCATT TTTATCCTCG CTCAGCAGGA     120

GCACATCAAT AAAGTCCAAA GTCTTGGACT TGGCCTTGGC TTGGAGGAAG TCATCAACAC     180

CCTGGCTAGT GAGGGTGCGG CGCCGCTCCT GGATGACGGC ATCTGTGAAG TCGTGCACCA     240

GTCTGCAGGC CCTGTGGAAG CGCCGTCCAC ACGGAGTNAG GAATT                    285

(2) INFORMATION FOR SEQ ID NO:154:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:154:

ACCACAGTCC TGTTGGGCCA GGGCTTCATG ACCCTTTCTG TGAAAAGCCA TATTATCACC      60

ACCCCAAATT TTTCCTTAAA TATCTTTAAC TGAAGGGGTC AGCCTCTTGA CTGCAAAGAC     120

CCTAAGCCGG TTACACAGCT AACTCCCACT GGCCCTGATT TGTGAAATTG CTGCTGCCTG     180

ATTGGCACAG GAGTCGAAGG TGTTCAGCTC CCCTCCTCCG TGGAACGAGA CTCTGATTTG     240

AGTTTCACAA ATTCTCGGGC CACCTCGTCA TTGCTCCTCT GAAATAAAAT CCGGAGAATG     300

GTCAGGCCTG TCTCATCCAT ATGGATCTTC CGG                                 333

(2) INFORMATION FOR SEQ ID NO:155:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:155:

```
ACTGGAAATA ATAAAACCCA CATCACAGTG TTGTGTCAAA GATCATCAGG GCATGGATGG      60

GAAAGTGCTT TGGGAACTGT AAAGTGCCTA ACACATGATC GATGATTTTT GTTATAATAT     120

TTGAATCACG GTGCATACAA ACTCTCCTGC CTGCTCCTCC TGGGCCCCAG CCCCAGCCCC     180

ATCACAGCTC ACTGCTCTGT TCATCCAGGC CCAGCATGTA GTGGCTGATT CTTCTTGGCT     240

GCTTTTAGCC TCCANAAGTT TCTCTGAAGC CAACCAAACC TCTANGTGTA AGGCATGCTG     300

GCCCTGGT                                                              308
```

(2) INFORMATION FOR SEQ ID NO:156:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:156:

```
ACCTTGCTCG GTGCTTGGAA CATATTAGGA ACTCAAAATA TGAGATGATA ACAGTGCCTA      60

TTATTGATTA CTGAGAGAAC TGTTAGACAT TTAGTTGAAG ATTTTCTACA CAGGAACTGA     120

GAATAGGAGA TTATGTTTGG CCCTCATATT CTCTCCTATC CTCCTTGCCT CATTCTATGT     180

CTAATATATT CTCAATCAAA TAAGGTTAGC ATAATCAGGA AATCGACCAA ATACCAATAT     240

AAAACCAGAT GTCTATCCTT AAGATTTTCA ATAGAAAAC AAATTAACAG ACTAT           295
```

(2) INFORMATION FOR SEQ ID NO:157:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:157:

```
ACAAGTTTAA ATAGTGCTGT CACTGTGCAT GTGCTGAAAT GTGAAATCCA CCACATTTCT      60

GAAGAGCAAA ACAAATTCTG TCATGTAATC TCTATCTTGG GTCGTGGGTA TATCTGTCCC     120

CTTAGT                                                                126
```

(2) INFORMATION FOR SEQ ID NO:158:

(i) SEQUENCE CHARACTERISTICS:
        (A) LENGTH: 442 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:158:

```
ACCCACTGGT CTTGGAAACA CCCATCCTTA ATACGATGAT TTTTCTGTCG TGTGAAAATG      60

AANCCAGCAG GCTGCCCCTA GTCAGTCCTT CCTTCCAGAG AAAAAGAGAT TTGAGAAAGT     120

GCCTGGGTAA TTCACCATTA ATTTCCTCCC CCAAACTCTC TGAGTCTTCC CTTAATATTT     180

CTGGTGGTTC TGACCAAAGC AGGTCATGGT TTGTTGAGCA TTTGGGATCC CAGTGAAGTA     240

NATGTTTGTA GCCTTGCATA CTTAGCCCTT CCCACGCACA AACGGAGTGG CAGAGTGGTG     300

CCAACCCTGT TTTCCCAGTC CACGTAGACA GATTCACAGT GCGGAATTCT GGAAGCTGGA     360

NACAGACGGG CTCTTTGCAG AGCCGGGACT CTGAGANGGA CATGAGGGCC TCTGCCTCTG     420

TGTTCATTCT CTGATGTCCT GT                                              442
```

(2) INFORMATION FOR SEQ ID NO:159:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:159:

```
ACTTCCAGGT AACGTTGTTG TTTCCGTTGA GCCTGAACTG ATGGGTGACG TTGTAGGTTC      60

TCCAACAAGA ACTGAGGTTG CAGAGCGGGT AGGGAAGAGT GCTGTTCCAG TTGCACCTGG     120

GCTGCTGTGG ACTGTTGTTG ATTCCTCACT ACGGCCCAAG GTTGTGGAAC TGGCANAAAG     180

GTGTGTTGTT GGANTTGAGC TCGGGCGGCT GTGGTAGGTT GTGGGCTCTT CAACAGGGGC     240

TGCTGTGGTG CCGGGANGTG AANGTGTTGT GTCACTTGAG CTTGGCCAGC TCTGGAAAGT     300

ANTANATTCT TCCTGAAGGC CAGCGCTTGT GGAGCTGGCA NGGGTCANTG TTGTGTGTAA     360

CGAACCAGTG CTGCTGTGGG TGGGTGTANA TCCTCCACAA AGCCTGAAGT TATGGTGTCN     420

TCAGGTAANA ATGTGGTTTC AGTGTCCCTG GGCNGCTGTG GAAGGTTGTA NATTGTCACC     480

AAGGGAATAA GCTGTGGT                                                   498
```

(2) INFORMATION FOR SEQ ID NO:160:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:160:

```
ACCTGCATCC AGCTTCCCTG CCAAACTCAC AAGGAGACAT CAACCTCTAG ACAGGGAAAC      60

AGCTTCAGGA TACTTCCAGG AGACAGAGCC ACCAGCAGCA AAACAAATAT TCCCATGCCT     120

GGAGCATGGC ATAGAGGAAG CTGANAAATG TGGGGTCTGA GGAAGCCATT TGAGTCTGGC     180

CACTAGACAT CTCATCAGCC ACTTGTGTGA AGAGATGCCC CATGACCCCA GATGCCTCTC     240

CCACCCTTAC CTCCATCTCA CACACTTGAG CTTTCCACTC TGTATAATTC TAACATCCTG     300
```

```
GAGAAAAATG GCAGTTTGAC CGAACCTGTT CACAACGGTA GAGGCTGATT TCTAACGAAA      360

CTTGTAGAAT GAAGCCTGGA                                                 380

(2) INFORMATION FOR SEQ ID NO:161:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:161:

ACTCCACATC CCCTCTGAGC AGGCGGTTGT CGTTCAAGGT GTATTTGGCC TTGCCTGTCA       60

CACTGTCCAC TGGCCCCTTA TCCACTTGGT GCTTAATCCC TCGAAAGAGC ATGT           114

(2) INFORMATION FOR SEQ ID NO:162:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:162:

ACTTTCTGAA TCGAATCAAA TGATACTTAG TGTAGTTTTA ATATCCTCAT ATATATCAAA       60

GTTTTACTAC TCTGATAATT TTGTAAACCA GGTAACCAGA ACATCCAGTC ATACAGCTTT     120

TGGTGATATA TAACTTGGCA ATAACCCAGT CTGGTGATAC ATAAAACTAC TCACTGT        177

(2) INFORMATION FOR SEQ ID NO:163:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:163:

CATTTATACA GACAGGCGTG AAGACATTCA CGACAAAAAC GCGAAATTCT ATCCCGTGAC       60

CANAGAAGGC AGCTACGGCT ACTCCTACAT CCTGGCGTGG GTGGCCTTCG CCTGCACCTT     120

CATCAGCGGC ATGATGT                                                   137

(2) INFORMATION FOR SEQ ID NO:164:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
        (A) ORGANISM: Homo sapiens (xi) SEQUENCE DESCRIPTION: SEQ ID NO:164:

| | | | | | |
|---|---|---|---|---|---|
| CTTATCACAA | TGAATGTTCT | CCTGGGCAGC | GTTGTGATCT | TTGCCACCTT | CGTGACTTTA | 60 |
| TGCAATGCAT | CATGCTATTT | CATACCTAAT | GAGGGAGTTC | CAGGAGATTC | AACCAGGAAA | 120 |
| TGCATGGATC | TCAAAGGAAA | CAAACACCCA | ATAAACTCGG | AGTGGCAGAC | TGACAACTGT | 180 |
| GAGACATGCA | CTTGCTACGA | AACAGAAATT | TCATGTTGCA | CCCTTGTTTC | TACACCTGTG | 240 |
| GGTTATGACA | AAGACAACTG | CCAAAGAATC | TTCAAGAAGG | AGGACTGCAA | GTATATCGTG | 300 |
| GTGGAGAAGA | AGGACCCAAA | AAAGACCTGT | TCTGTCAGTG | AATGGATAAT | CTAATGTGCT | 360 |
| TCTAGTAGGC | ACAGGGCTCC | CAGGCCAGGC | CTCATTCTCC | TCTGGCCTCT | AATAGTCAAT | 420 |
| GATTGTGTAG | CCATGCCTAT | CAGTAAAAAG | ATNTTTGAGC | AAACACTTT | | 469 |

(2) INFORMATION FOR SEQ ID NO:165:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:165:

| | | | | | |
|---|---|---|---|---|---|
| ACAGTTTTTT | ATANATATCG | ACATTGCCGG | CACTTGTGTT | CAGTTTCATA | AAGCTGGTGG | 60 |
| ATCCGCTGTC | ATCCACTATT | CCTTGGCTAG | AGTAAAAATT | ATTCTTATAG | CCCATGTCCC | 120 |
| TGCAGGCCGC | CCGCCCGTAG | TTCTCGTTCC | AGTCGTCTTG | GCACACAGGG | TGCCAGGACT | 180 |
| TCCTCTGAGA | TGAGT | | | | | 195 |

(2) INFORMATION FOR SEQ ID NO:166:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:166:

| | | | | | |
|---|---|---|---|---|---|
| ACATCTTAGT | AGTGTGGCAC | ATCAGGGGGC | CATCAGGGTC | ACAGTCACTC | ATAGCCTCGC | 60 |
| CGAGGTCGGA | GTCCACACCA | CCGGTGTAGG | TGTGCTCAAT | CTTGGGCTTG | GCGCCCACCT | 120 |
| TTGGAGAAGG | GATATGCTGC | ACACACATGT | CCACAAAGCC | TGTGAACTCG | CCAAAGAATT | 180 |
| TTTGCAGACC | AGCCTGAGCA | AGGGGCGGAT | GTTCAGCTTC | AGCTCCTCCT | TCGTCAGGTG | 240 |
| GATGCCAACC | TCGTCTANGG | TCCGTGGGAA | GCTGGTGTCC | ACNTCACCTA | CAACCTGGGC | 300 |
| GANGATCTTA | TAAAGAGGCT | CCNAGATAAA | CTCCACGAAA | CTTCTCTGGG | AGCTGCTAGT | 360 |
| NGGGGCCTTT | TTGGTGAACT | TTC | | | | 383 |

(2) INFORMATION FOR SEQ ID NO:167:

(i) SEQUENCE CHARACTERISTICS:

(A) LENGTH: 247 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:167:

```
ACAGAGCCAG ACCTTGGCCA TAAATGAANC AGAGATTAAG ACTAAACCCC AAGTCGANAT    60

TGGAGCAGAA ACTGGAGCAA GAAGTGGGCC TGGGGCTGAA GTAGAGACCA AGGCCACTGC   120

TATANCCATA CACAGAGCCA ACTCTCAGGC CAAGGCNATG GTTGGGGCAG ANCCAGAGAC   180

TCAATCTGAN TCCAAAGTGG TGGCTGGAAC ACTGGTCATG ACANAGGCAG TGACTCTGAC   240

TGANGTC                                                             247
```

(2) INFORMATION FOR SEQ ID NO:168:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:168:

```
ACTTCTAAGT TTTCTAGAAG TGGAAGGATT GTANTCATCC TGAAAATGGG TTTACTTCAA    60

AATCCCTCAN CCTTGTTCTT CACNACTGTC TATACTGANA GTGTCATGTT TCCACAAAGG   120

GCTGACACCT GAGCCTGNAT TTTCACTCAT CCCTGAGAAG CCCTTTCCAG TAGGGTGGGC   180

AATTCCCAAC TTCCTTGCCA CAAGCTTCCC AGGCTTTCTC CCCTGGAAAA CTCCAGCTTG   240

AGTCCCAGAT ACACTCATGG GCTGCCCTGG GCA                                273
```

(2) INFORMATION FOR SEQ ID NO:169:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:169:

```
ACAGCCTTGG CTTCCCCAAA CTCCACAGTC TCAGTGCAGA AAGATCATCT TCCAGCAGTC    60

AGCTCAGACC AGGGTCAAAG GATGTGACAT CAACAGTTTC TGGTTTCAGA ACAGGTTCTA   120

CTACTGTCAA ATGACCCCCC ATACTTCCTC AAAGGCTGTG GTAAGTTTTG CACAGGTGAG   180

GGCAGCAGAA AGGGGGTANT TACTGATGGA CACCATCTTC TCTGTATACT CCACACTGAC   240

CTTGCCATGG GCAAAGGCCC CTACCACAAA AACAATAGGA TCACTGCTGG GCACCAGCTC   300

ACGCACATCA CTGACAACCG GGATGGAAAA AGAANTGCCA ACTTTCATAC ATCCAACTGG   360

AAAGTGATCT GATACTGGAT TCTTAATTAC CTTCAAAAGC TTCTGGGGGC CATCAGCTGC   420

TCGAACACTG A                                                        431
```

(2) INFORMATION FOR SEQ ID NO:170:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:170:

```
ACCTGTGGGC TGGGCTGTTA TGCCTGTGCC GGCTGCTGAA AGGGAGTTCA GAGGTGGAGC      60

TCAAGGAGCT CTGCAGGCAT TTTGCCAANC CTCTCCANAG CANAGGGAGC AACCTACACT     120

CCCCGCTAGA AAGACACCAG ATTGGAGTCC TGGGAGGGGG AGTTGGGGTG GGCATTTGAT     180

GTATACTTGT CACCTGAATG AANGAGCCAG AGAGGAANGA GACGAANATG ANATTGGCCT     240

TCAAAGCTAG GGGTCTGGCA GGTGGA                                         266
```

(2) INFORMATION FOR SEQ ID NO:171:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:171:

```
GGCAGCCAAA TCATAAACGG CGAGGACTGC AGCCCGCACT CGCAGCCCTG GCAGGCGGCA      60

CTGGTCATGG AAAACGAATT GTTCTGCTCG GGCGTCCTGG TGCATCCGCA GTGGGTGCTG     120

TCAGCCGCAC ACTGTTTCCA GAAGTGAGTG CAGAGCTCCT ACACCATCGG GCTGGGCCTG     180

CACAGTCTTG AGGCCGACCA AGAGCCAGGG AGCCAGATGG TGGAGGCCAG CCTCTCCGTA     240

CGGCACCCAG AGTACAACAG ACCCTTGCTC GCTAACGACC TCATGCTCAT CAAGTTGGAC     300

GAATCCGTGT CCGAGTCTGA CACCATCCGG AGCATCAGCA TTGCTTCGCA GTGCCCTACC     360

GCGGGGAACT CTTGCCTCGT TTCTGGCTGG GGTCTGCTGG CGAACGGCAG AATGCCTACC     420

GTGCTGCAGT GCGTGAACGT GTCGGTGGTG TCTGAGGAGG TCTGCAGTAA GCTCTATGAC     480

CCGCTGTACC ACCCCAGCAT GTTCTGCGCC GGCGGAGGGC AAGACCAGAA GGACTCCTGC     540

AACGGTGACT CTGGGGGGCC CCTGATCTGC AACGGGTACT GCAGGGCCT TGTGTCTTTC      600

GGAAAAGCCC CGTGTGGCCA AGTTGGCGTG CCAGGTGTCT ACACCAACCT CTGCAAATTC     660

ACTGAGTGGA TAGAGAAAAC CGTCCAGGCC AGTTAACTCT GGGGACTGGG AACCCATGAA     720

ATTGACCCCC AAATACATCC TGCGGAAGGA ATTCAGGAAT ATCTGTTCCC AGCCCCTCCT     780

CCCTCAGGCC CAGGAGTCCA GGCCCCCAGC CCCTCCTCCC TCAAACCAAG GGTACAGATC     840

CCCAGCCCCT CCTCCCTCAG ACCCAGGAGT CCAGACCCCC CAGCCCCTCC TCCCTCAGAC     900

CCAGGAGTCC AGCCCCTCCT CCCTCAGACC CAGGAGTCCA GACCCCCCAG CCCCTCCTCC     960

CTCAGACCCA GGGGTCCAGG CCCCCAACCC CTCCTCCCTC AGACTCAGAG GTCCAAGCCC    1020

CCAACCCNTC ATTCCCCAGA CCCAGAGGTC CAGGTCCCAG CCCCTCNTCC CTCAGACCCA    1080
```

```
GCGGTCCAAT GCCACCTAGA CTNTCCCTGT ACACAGTGCC CCCTTGTGGC ACGTTGACCC      1140

AACCTTACCA GTTGGTTTTT CATTTTTNGT CCCTTTCCCC TAGATCCAGA AATAAAGTTT      1200

AAGAGAAGNG CAAAAAAAAA AAAAAAAAAA AAAAAAAAAA AAAAAAAA                   1248
```

(2) INFORMATION FOR SEQ ID NO:172:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:172:

```
Met Val Glu Ala Ser Leu Ser Val Arg His Pro Glu Tyr Asn Arg Pro
1               5                  10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

(2) INFORMATION FOR SEQ ID NO:173:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:173:

```
GGCAGCCCGC ACTCGCAGCC CTGGCAGGCG GCACTGGTCA TGGAAAACGA ATTGTTCTGC      60

TCGGGCGTCC TGGTGCATCC GCAGTGGGTG CTGTCAGCCG CACACTGTTT CCAGAACTCC     120

TACACCATCG GCTGGGCCT GCACAGTCTT GAGGCCGACC AAGAGCCAGG GAGCCAGATG      180

GTGGAGGCCA GCCTCTCCGT ACGGCACCCA GAGTACAACA GACCCTTGCT CGCTAACGAC     240

CTCATGCTCA TCAAGTTGGA CGAATCCGTG TCCGAGTCTG ACACCATCCG GAGCATCAGC     300

ATTGCTTCGC AGTGCCCTAC CGCGGGGAAC TCTTGCCTCG TTTCTGGCTG GGGTCTGCTG     360
```

```
GCGAACGGTG AGCTCACGGG TGTGTGTCTG CCCTCTTCAA GGAGGTCCTC TGCCCAGTCG      420

CGGGGGCTGA CCCAGAGCTC TGCGTCCCAG GCAGAATGCC TACCGTGCTG CAGTGCGTGA      480

ACGTGTCGGT GGTGTCTGAG GAGGTCTGCA GTAAGCTCTA TGACCCGCTG TACCACCCCA      540

GCATGTTCTG CGCCGGCGGA GGGCAAGACC AGAAGGACTC CTGCAACGGT GACTCTGGGG      600

GGCCCCTGAT CTGCAACGGG TACTTGCAGG GCCTTGTGTC TTTCGGAAAA GCCCCGTGTG      660

GCCAAGTTGG CGTGCCAGGT GTCTACACCA ACCTCTGCAA ATTCACTGAG TGGATAGAGA      720

AAACCGTCCA GGCCAGTTAA CTCTGGGGAC TGGGAACCCA TGAAATTGAC CCCCAAATAC      780

ATCCTGCGGA AGGAATTCAG GAATATCTGT TCCCAGCCCC TCCTCCCTCA GGCCCAGGAG      840

TCCAGGCCCC CAGCCCCTCC TCCCTCAAAC CAAGGGTACA GATCCCCAGC CCCTCCTCCC      900

TCAGACCCAG GAGTCCAGAC CCCCAGCCC CTCCTCCCTC AGACCCAGGA GTCCAGCCCC      960

TCCTCCNTCA GACCCAGGAG TCCAGACCCC CCAGCCCCTC CTCCCTCAGA CCCAGGGGTT     1020

GAGGCCCCCA ACCCCTCCTC CTTCAGAGTC AGAGGTCCAA GCCCCCAACC CCTCGTTCCC     1080

CAGACCCAGA GGTNNAGGTC CCAGCCCCTC TTCCNTCAGA CCCAGNGGTC CAATGCCACC     1140

TAGATTTTCC CTGNACACAG TGCCCCCTTG TGGNANGTTG ACCCAACCTT ACCAGTTGGT     1200

TTTTCATTTT TNGTCCCTTT CCCCTAGATC CAGAAATAAA GTTAAGAGA NGNGCAAAAA     1260

AAAAA                                                                1265

(2) INFORMATION FOR SEQ ID NO:174:

(i) SEQUENCE CHARACTERISTICS:
        (A) LENGTH: 1459 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:174:

GGTCAGCCGC ACACTGTTTC CAGAAGTGAG TGCAGAGCTC CTACACCATC GGGCTGGGCC       60

TGCACAGTCT TGAGGCCGAC CAAGAGCCAG GGAGCCAGAT GGTGGAGGCC AGCCTCTCCG      120

TACGGCACCC AGAGTACAAC AGACCCTTGC TCGCTAACGA CCTCATGCTC ATCAAGTTGG      180

ACGAATCCGT GTCCGAGTCT GACACCATCC GGAGCATCAG CATTGCTTCG CAGTGCCCTA      240

CCGCGGGGAA CTCTTGCCTC GTTTCTGGCT GGGGTCTGCT GGCGAACGGT GAGCTCACGG      300

GTGTGTGTCT GCCCTCTTCA AGGAGGTCCT CTGCCCAGTC GCGGGGGCTG ACCCAGAGCT      360

CTGCGTCCCA GGCAGAATGC CTACCGTGCT GCAGTGCGTG AACGTGTCGG TGGTGTCTGA      420

NGAGGTCTGC ANTAAGCTCT ATGACCCGCT GTACCACCCC ANCATGTTCT GCGCCGGCGG      480

AGGGCAAGAC CAGAAGGACT CCTGCAACGT GAGAGAGGGG AAAGGGGAGG GCAGGCGACT      540

CAGGGAAGGG TGGAGAAGGG GGAGACAGAG ACACACAGGG CCGCATGGCG AGATGCAGAG      600

ATGGAGAGAC ACACAGGGAG ACAGTGACAA CTAGAGAGAG AAACTGAGAG AAACAGAGAA      660

ATAAACACAG GAATAAAGAG AAGCAAAGGA AGAGAGAAAC AGAAACAGAC ATGGGGAGGC      720

AGAAACACAC ACACATAGAA ATGCAGTTGA CCTTCCAACA GCATGGGGCC TGAGGGCGGT      780

GACCTCCACC CAATAGAAAA TCCTCTTATA ACTTTTGACT CCCCAAAAAC CTGACTAGAA      840

ATAGCCTACT GTTGACGGGG AGCCTTACCA ATAACATAAA TAGTCGATTT ATGCATACGT      900
```

```
TTTATGCATT CATGATATAC CTTTGTTGGA ATTTTTTGAT ATTTCTAAGC TACACAGTTC      960

GTCTGTGAAT TTTTTTAAAT TGTTGCAACT CTCCTAAAAT TTTTCTGATG TGTTTATTGA     1020

AAAAATCCAA GTATAAGTGG ACTTGTGCAT TCAAACCAGG GTTGTTCAAG GGTCAACTGT     1080

GTACCCAGAG GGAAACAGTG ACACAGATTC ATAGAGGTGA AACACGAAGA GAAACAGGAA     1140

AAATCAAGAC TCTACAAAGA GGCTGGGCAG GGTGGCTCAT GCCTGTAATC CCAGCACTTT     1200

GGGAGGCGAG GCAGGCAGAT CACTTGAGGT AAGGAGTTCA AGACCAGCCT GGCCAAAATG     1260

GTGAAATCCT GTCTGTACTA AAATACAAA AGTTAGCTGG ATATGGTGGC AGGCGCCTGT      1320

AATCCCAGCT ACTTGGGAGG CTGAGGCAGG AGAATTGCTT GAATATGGGA GGCAGAGGTT     1380

GAAGTGAGTT GAGATCACAC CACTATACTC CAGCTGGGGC AACAGAGTAA GACTCTGTCT     1440

CAAAAAAAAA AAAAAAAA                                                   1459

(2) INFORMATION FOR SEQ ID NO:175:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:175:

GCGCAGCCCT GGCAGGCGGC ACTGGTCATG GAAAACGAAT TGTTCTGCTC GGGCGTCCTG       60

GTGCATCCGC AGTGGGTGCT GTCAGCCGCA CACTGTTTCC AGAACTCCTA CACCATCGGG      120

CTGGGCCTGC ACAGTCTTGA GGCCGACCAA GAGCCAGGGA GCCAGATGGT GGAGGCCAGC      180

CTCTCCGTAC GGCACCCAGA GTACAACAGA CTCTTGCTCG CTAACGACCT CATGCTCATC      240

AAGTTGGACG AATCCGTGTC CGAGTCTGAC ACCATCCGGA GCATCAGCAT TGCTTCGCAG      300

TGCCCTACCG CGGGGAACTC TTGCCTCGTN TCTGGCTGGG GTCTGCTGGC GAACGGCAGA      360

ATGCCTACCG TGCTGCACTG CGTGAACGTG TCGGTGGTGT CTGAGGANGT CTGCAGTAAG      420

CTCTATGACC CGCTGTACCA CCCCAGCATG TTCTGCGCCG GCGGAGGGCA AGACCAGAAG      480

GACTCCTGCA ACGGTGACTC TGGGGGGCCC CTGATCTGCA ACGGGTACTT GCAGGGCCTT      540

GTGTCTTTCG GAAAAGCCCC GTGTGGCCAA CTTGGCGTGC CAGGTGTCTA CACCAACCTC      600

TGCAAATTCA CTGAGTGGAT AGAGAAAACC GTCCAGNCCA GTTAACTCTG GGGACTGGGA      660

ACCCATGAAA TTGACCCCCA AATACATCCT GCGGAANGAA TTCAGGAATA TCTGTTCCCA      720

GCCCCTCCTC CCTCAGGCCC AGGAGTCCAG GCCCCCAGCC CCTCCTCCCT CAAACCAAGG      780

GTACAGATCC CCAGCCCCTC CTCCCTCAGA CCCAGGAGTC CAGACCCCCC AGCCCCTCNT      840

CCNTCAGACC CAGGAGTCCA GCCCCTCCTC CNTCAGACGC AGGAGTCCAG ACCCCCCAGC      900

CCNTCNTCCG TCAGACCCAG GGGTGCAGGC CCCCAACCCC TCNTCCNTCA GAGTCAGAGG      960

TCCAAGCCCC CAACCCCTCG TTCCCCAGAC CCAGAGGTNC AGGTCCCAGC CCCTCCTCCC     1020

TCAGACCCAG CGGTCCAATG CCACCTAGAN TNTCCCTGTA CACAGTGCCC CCTTGTGGCA     1080

NGTTGACCCA ACCTTACCAG TTGGTTTTTC ATTTTTTGTC CCTTTCCCCT AGATCCAGAA     1140

ATAAAGTNTA AGAGAAGCGC AAAAAAA                                        1167

(2) INFORMATION FOR SEQ ID NO:176:
```

(i) SEQUENCE CHARACTERISTICS:
    (A) LENGTH: 205 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: Homo sapiens (xi) SEQUENCE DESCRIPTION: SEQ ID NO:176:

```
Met Glu Asn Glu Leu Phe Cys Ser Gly Val Leu Val His Pro Gln Trp
1               5                   10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
            35                  40                  45

Glu Ala Ser Leu Ser Val Arg His Pro Glu Tyr Asn Arg Leu Leu Leu
50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
                100                 105                 110

Pro Thr Val Leu His Cys Val Asn Val Ser Val Val Ser Glu Xaa Val
                115                 120                 125

Cys Ser Lys Leu Tyr Asp Pro Leu Tyr His Pro Ser Met Phe Cys Ala
130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
                180                 185                 190

Lys Phe Thr Glu Trp Ile Glu Lys Thr Val Gln Xaa Ser
                195                 200                 205
```

(2) INFORMATION FOR SEQ ID NO:177:

(i) SEQUENCE CHARACTERISTICS:
    (A) LENGTH: 1119 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:177:

```
GCGCACTCGC AGCCCTGGCA GGCGGCACTG GTCATGGAAA ACGAATTGTT CTGCTCGGGC     60

GTCCTGGTGC ATCCGCAGTG GGTGCTGTCA GCCGCACACT GTTTCCAGAA CTCCTACACC    120

ATCGGGCTGG GCCTGCACAG TCTTGAGGCC GACCAAGAGC CAGGGAGCCA GATGGTGGAG    180

GCCAGCCTCT CCGTACGGCA CCCAGAGTAC AACAGACCCT TGCTCGCTAA CGACCTCATG    240

CTCATCAAGT TGGACGAATC CGTGTCCGAG TCTGACACCA TCCGGAGCAT CAGCATTGCT    300

TCGCAGTGCC CTACCGCGGG GAACTCTTGC CTCGTTTCTG GCTGGGGTCT GCTGGCGAAC    360
```

-continued

```
GATGCTGTGA TTGCCATCCA GTCCCAGACT GTGGGAGGCT GGGAGTGTGA GAAGCTTTCC    420

CAACCCTGGC AGGGTTGTAC CATTTCGGCA ACTTCCAGTG CAAGGACGTC CTGCTGCATC    480

CTCACTGGGT GCTCACTACT GCTCACTGCA TCACCCGGAA CACTGTGATC AACTAGCCAG    540

CACCATAGTT CTCCGAAGTC AGACTATCAT GATTACTGTG TTGACTGTGC TGTCTATTGT    600

ACTAACCATG CCGATGTTTA GGTGAAATTA GCGTCACTTG GCCTCAACCA TCTTGGTATC    660

CAGTTATCCT CACTGAATTG AGATTTCCTG CTTCAGTGTC AGCCATTCCC ACATAATTTC    720

TGACCTACAG AGGTGAGGGA TCATATAGCT CTTCAAGGAT GCTGGTACTC CCCTCACAAA    780

TTCATTTCTC CTGTTGTAGT GAAAGGTGCG CCCTCTGGAG CCTCCCAGGG TGGGTGTGCA    840

GGTCACAATG ATGAATGTAT GATCGTGTTC CCATTACCCA AAGCCTTTAA ATCCCTCATG    900

CTCAGTACAC CAGGGCAGGT CTAGCATTTC TTCATTTAGT GTATGCTGTC CATTCATGCA    960

ACCACCTCAG GACTCCTGGA TTCTCTGCCT AGTTGAGCTC CTGCATGCTG CCTCCTTGGG   1020

GAGGTGAGGG AGAGGGCCCA TGGTTCAATG GGATCTGTGC AGTTGTAACA CATTAGGTGC   1080

TTAATAAACA GAAGCTGTGA TGTTAAAAAA AAAAAAAAA                          1119
```

(2) INFORMATION FOR SEQ ID NO:178:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:178:

```
Met Glu Asn Glu Leu Phe Cys Ser Gly Val Leu Val His Pro Gln Trp
1               5                   10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Pro Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Leu Thr Ala Ser
145                 150                 155                 160

Pro Gly Thr Leu
```

(2) INFORMATION FOR SEQ ID NO:179:

(i) SEQUENCE CHARACTERISTICS:

(A) LENGTH: 250 base pairs
        (B) TYPE: nucleic acid
        (C) STRANDEDNESS: single
        (D) TOPOLOGY: linear (xi) SEQUENCE DESCRIPTION: SEQ ID NO:179:

CTGGAGTGCC TTGGTGTTTC AAGCCCCTGC AGGAAGCAGA ATGCACCTTC TGAGGCACCT      60

CCAGCTGCCC CCGGCCGGGG GATGCGAGGC TCGGAGCACC CTTGCCCGGC TGTGATTGCT     120

GCCAGGCACT GTTCATCTCA GCTTTTCTGT CCCTTTGCTC CCGGCAAGCG CTTCTGCTGA     180

AAGTTCATAT CTGGAGCCTG ATGTCTTAAC GAATAAAGGT CCCATGCTCC ACCCGAAAAA     240

AAAAAAAAAA                                                            250

(2) INFORMATION FOR SEQ ID NO:180:

(i) SEQUENCE CHARACTERISTICS:
        (A) LENGTH: 202 base pairs
        (B) TYPE: nucleic acid
        (C) STRANDEDNESS: single
        (D) TOPOLOGY: linear (xi) SEQUENCE DESCRIPTION: SEQ ID NO:180:

ACTAGTCCAG TGTGGTGGAA TTCCATTGTG TTGGGCCCAA CACAATGGCT ACCTTTAACA      60

TCACCCAGAC CCCGCCCCTG CCCGTGCCCC ACGCTGCTGC TAACGACAGT ATGATGCTTA     120

CTCTGCTACT CGGAAACTAT TTTTATGTAA TTAATGTATG CTTTCTTGTT TATAAATGCC     180

TGATTTAAAA AAAAAAAAAA AA                                              202

(2) INFORMATION FOR SEQ ID NO:181:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (xi) SEQUENCE DESCRIPTION: SEQ ID NO:181:

TCCYTTTGKT NAGGTTTKKG AGACAMCCCK AGACCTWAAN CTGTGTCACA GACTTCYNGG      60

AATGTTTAGG CAGTGCTAGT AATTTCYTCG TAATGATTCT GTTATTACTT TCCTNATTCT     120

TTATTCCTCT TTCTTCTGAA GATTAATGAA GTTGAAAATT GAGGTGGATA AATACAAAAA     180

GGTAGTGTGA TAGTATAAGT ATCTAAGTGC AGATGAAAGT GTGTTATATA TATCCATTCA     240

AAATTATGCA AGTTAGTAAT TACTCAGGGT TAACTAAATT ACTTTAATAT GCTGTTGAAC     300

CTACTCTGTT CCTTGGCTAG AAAAAATTAT AAACAGGACT TTGTTAGTTT GGGAAGCCAA     360

ATTGATAATA TTCTATGTTC TAAAAGTTGG GCTATACATA AATTATTAAG AAATATGGAW     420

TTTTATTCCC AGGAATATGG KGTTCATTTT ATGAATATTA CSCRGGATAG AWGTWTGAGT     480

AAAAYCAGTT TTGGTWAATA YGTWAATATG TCMTAAATAA ACAAKGCTTT GACTTATTTC     540

CAAAAAAAAA AAAAAAAA                                                   558

(2) INFORMATION FOR SEQ ID NO:182:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (xi) SEQUENCE DESCRIPTION: SEQ ID NO:182:

ACAGGGWTTK GRGGATGCTA AGSCCCCRGA RWTYGTTTGA TCCAACCCTG GCTTWTTTTC      60

| | | | | | |
|---|---|---|---|---|---|
|AGAGGGGAAA|ATGGGGCCTA|GAAGTTACAG|MSCATYTAGY|TGGTGCGMTG|GCACCCCTGG|120|
|CSTCACACAG|ASTCCCGAGT|AGCTGGGACT|ACAGGCACAC|AGTCACTGAA|GCAGGCCCTG|180|
|TTWGCAATTC|ACGTTGCCAC|CTCCAACTTA|AACATTCTTC|ATATGTGATG|TCCTTAGTCA|240|
|CTAAGGTTAA|ACTTTCCCAC|CCAGAAAAGG|CAACTTAGAT|AAAATCTTAG|AGTACTTTCA|300|
|TACTMTTCTA|AGTCCTCTTC|CAGCCTCACT|KKGAGTCCTM|CYTGGGGGTT|GATAGGAANT|360|
|NTCTCTTGGC|TTTCTCAATA|AARTCTCTAT|YCATCTCATG|TTTAATTTGG|TACGCATARA|420|
|AWTGSTGARA|AAATTAAAAT|GTTCTGGTTY|MACTTTAAAA|ARAAAAAAAA|AAAAAAAA|479|

(2) INFORMATION FOR SEQ ID NO:183:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (xi) SEQUENCE DESCRIPTION: SEQ ID NO:183:

| | | | | | |
|---|---|---|---|---|---|
|AGGCGGGAGC|AGAAGCTAAA|GCCAAAGCCC|AAGAAGAGTG|GCAGTGCCAG|CACTGGTGCC|60|
|AGTACCAGTA|CCAATAACAG|TGCCAGTGCC|AGTGCCAGCA|CCAGTGGTGG|CTTCAGTGCT|120|
|GGTGCCAGCC|TGACCGCCAC|TCTCACATTT|GGGCTCTTCG|CTGGCCTTGG|TGGAGCTGGT|180|
|GCCAGCACCA|GTGGCAGCTC|TGGTGCCTGT|GGTTTCTCCT|ACAAGTGAGA|TTTTAGATAT|240|
|TGTTAATCCT|GCCAGTCTTT|CTCTTCAAGC|CAGGGTGCAT|CCTCAGAAAC|CTACTCAACA|300|
|CAGCACTCTA|GGCAGCCACT|ATCAATCAAT|TGAAGTTGAC|ACTCTGCATT|ARATCTATTT|360|
|GCCATTTCAA|AAAAAAAAAA|AAAA| | | |384|

(2) INFORMATION FOR SEQ ID NO:184:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (xi) SEQUENCE DESCRIPTION: SEQ ID NO:184:

| | | | | | |
|---|---|---|---|---|---|
|ACCGAATTGG|GACCGCTGGC|TTATAAGCGA|TCATGTYYNT|CCRGTATKAC|CTCAACGAGC|60|
|AGGGAGATCG|AGTCTATACG|CTGAAGAAAT|TTGACCCGAT|GGGACAACAG|ACCTGCTCAG|120|
|CCCATCCTGC|TCGGTTCTCC|CCAGATGACA|AATACTCTSG|ACACCGAATC|ACCATCAAGA|180|
|AACGCTTCAA|GGTGCTCATG|ACCCAGCAAC|CGCGCCCTGT|CCTCTGAGGG|TCCCTTAAAC|240|
|TGATGTCTTT|TCTGCCACCT|GTTACCCCTC|GGAGACTCCG|TAACCAAACT|CTTCGGACTG|300|
|TGAGCCCTGA|TGCCTTTTTG|CCAGCCATAC|TCTTTGGCAT|CCAGTCTCTC|GTGGCGATTG|360|
|ATTATGCTTG|TGTGAGGCAA|TCATGGTGGC|ATCACCCATA|AAGGGAACAC|ATTTGACTTT|420|
|TTTTTCTCAT|ATTTTAAATT|ACTACMAGAW|TATTWMAGAW|WAAATGAWTT|GAAAAACTST|480|
|TAAAAAAAAA|AAAAAA| | | | |496|

(2) INFORMATION FOR SEQ ID NO:185:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (xi) SEQUENCE DESCRIPTION: SEQ ID NO:185:

```
GCTGGTAGCC TATGGCGKGG CCCACGGAGG GGCTCCTGAG GCCACGGRAC AGTGACTTCC        60

CAAGTATCYT GCGCSGCGTC TTCTACCGTC CCTACCTGCA GATCTTCGGG CAGATTCCCC       120

AGGAGGACAT GGACGTGGCC CTCATGGAGC ACAGCAACTG YTCGTCGGAG CCCGGCTTCT       180

GGGCACACCC TCCTGGGGCC CAGGCGGGCA CCTGCGTCTC CCAGTATGCC AACTGGCTGG       240

TGGTGCTGCT CCTCGTCATC TTCCTGCTCG TGGCCAACAT CCTGCTGGTC AACTTGCTCA       300

TTGCCATGTT CAGTTACACA TTCGGCAAAG TACAGGGCAA CAGCGATCTC TACTGGGAAG       360

GCGCAGCGTT ACCGCCTCAT CCGG                                              384

(2) INFORMATION FOR SEQ ID NO:186:

(i) SEQUENCE CHARACTERISTICS:
        (A) LENGTH: 577 base pairs
        (B) TYPE: nucleic acid
        (C) STRANDEDNESS: single
        (D) TOPOLOGY: linear (xi) SEQUENCE DESCRIPTION: SEQ ID NO:186:

GAGTTAGCTC CTCCACAACC TTGATGAGGT CGTCTGCAGT GGCCTCTCGC TTCATACCGC        60

TNCCATCGTC ATACTGTAGG TTTGCCACCA CYTCCTGGCA TCTTGGGGCG GCNTAATATT       120

CCAGGAAACT CTCAATCAAG TCACCGTCGA TGAAACCTGT GGGCTGGTTC TGTCTTCCGC       180

TCGGTGTGAA AGGATCTCCC AGAAGGAGTG CTCGATCTTC CCCACACTTT TGATGACTTT       240

ATTGAGTCGA TTCTGCATGT CCAGCAGGAG GTTGTACCAG CTCTCTGACA GTGAGGTCAC       300

CAGCCCTATC ATGCCGTTGA MCGTGCCGAA GARCACCGAG CCTTGTGTGG GGGKKGAAGT       360

CTCACCCAGA TTCTGCATTA CCAGAGAGCC GTGGCAAAAG ACATTGACAA ACTCGCCCAG       420

GTGGAAAAAG AMCAMCTCCT GGARGTGCTN GCCGCTCCTC GTCMGTTGGT GGCAGCGCTW       480

TCCTTTTGAC ACACAAACAA GTTAAAGGCA TTTTCAGCCC CCAGAAANTT GTCATCATCC       540

AAGATNTCGC ACAGCACTNA TCCAGTTGGG ATTAAAT                                577

(2) INFORMATION FOR SEQ ID NO:187:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (xi) SEQUENCE DESCRIPTION: SEQ ID NO:187:

AACATCTTCC TGTATAATGC TGTGTAATAT CGATCCGATN TTGTCTGSTG AGAATYCATW        60

ACTKGGAAAA GMAACATTAA AGCCTGGACA CTGGTATTAA AATTCACAAT ATGCAACACT       120

TTAAACAGTG TGTCAATCTG CTCCCYYNAC TTTGTCATCA CCAGTCTGGG AAKAAGGGTA       180

TGCCCTATTC ACACCTGTTA AAAGGGCGCT AAGCATTTTT GATTCAACAT CTTTTTTTTT       240

GACACAAGTC CGAAAAAAGC AAAAGTAAAC AGTTATYAAT TTGTTAGCCA ATTCACTTTC       300

TTCATGGGAC AGAGCCATYT GATTTAAAAA GCAAATTGCA TAATATTGAG CTTYGGGAGC       360

TGATATTTGA GCGGAAGAGT AGCCTTTCTA CTTCACCAGA CACAACTCCC TTTCATATTG       420

GGATGTTNAC NAAAGTWATG TCTCTWACAG ATGGGATGCT TTTGTGGCAA TTCTGTTCTG       480

AGGATCTCCC AGTTTATTTA CCACTTGCAC AAGAAGGCGT TTTCTTCCTC AGGC             534

(2) INFORMATION FOR SEQ ID NO:188:

(i) SEQUENCE CHARACTERISTICS:
```

```
        (A) LENGTH: 761 base pairs
        (B) TYPE: nucleic acid
        (C) STRANDEDNESS: single
        (D) TOPOLOGY: linear (xi) SEQUENCE DESCRIPTION: SEQ ID NO:188:

AGAAACCAGT ATCTCTNAAA ACAACCTCTC ATACCTTGTG GACCTAATTT TGTGTGCGTG      60

TGTGTGTGCG CGCATATTAT ATAGACAGGC ACATCTTTTT TACTTTTGTA AAAGCTTATG     120

CCTCTTTGGT ATCTATATCT GTGAAAGTTT TAATGATCTG CCATAATGTC TTGGGGACCT     180

TTGTCTTCTG TGTAAATGGT ACTAGAGAAA ACACCTATNT TATGAGTCAA TCTAGTTNGT     240

TTTATTCGAC ATGAAGGAAA TTTCCAGATN ACAACACTNA CAAACTCTCC CTKGACKARG     300

GGGGACAAAG AAAAGCAAAA CTGAMCATAA RAAACAATWA CCTGGTGAGA ARTTGCATAA     360

ACAGAAATWR GGTAGTATAT TGAARNACAG CATCATTAAA RMGTTWTKTT WTTCTCCCTT     420

GCAAAAAACA TGTACNGACT TCCCGTTGAG TAATGCCAAG TTGTTTTTTT TATNATAAAA     480

CTTGCCCTTC ATTACATGTT TNAAAGTGGT GTGGTGGGCC AAAATATTGA AATGATGGAA     540

CTGACTGATA AAGCTGTACA AATAAGCAGT GTGCCTAACA AGCAACACAG TAATGTTGAC     600

ATGCTTAATT CACAAATGCT AATTTCATTA TAAATGTTTG CTAAAATACA CTTTGAACTA     660

TTTTTCTGTN TTCCCAGAGC TGAGATNTTA GATTTTATGT AGTATNAAGT GAAAAANTAC     720

GAAAATAATA ACATTGAAGA AAAANANAAA AAANAAAAAA A                        761

(2) INFORMATION FOR SEQ ID NO:189:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (xi) SEQUENCE DESCRIPTION: SEQ ID NO:189:

TTTTTTTTTT TTTGCCGATN CTACTATTTT ATTGCAGGAN GTGGGGTGT ATGCACCGCA       60

CACCGGGGCT ATNAGAAGCA AGAAGGAAGG AGGGAGGGCA CAGCCCCTTG CTGAGCAACA     120

AAGCCGCCTG CTGCCTTCTC TGTCTGTCTC CTGGTGCAGG CACATGGGGA GACCTTCCCC     180

AAGGCAGGGG CCACCAGTCC AGGGGTGGGA ATACAGGGGG TGGGANGTGT GCATAAGAAG     240

TGATAGGCAC AGGCCACCCG GTACAGACCC CTCGGCTCCT GACAGGTNGA TTTCGACCAG     300

GTCATTGTGC CCTGCCCAGG CACAGCGTAN ATCTGGAAAA GACAGAATGC TTTCCTTTTC     360

AAATTTGGCT NGTCATNGAA NGGGCANTTT TCCAANTTNG GCTNGGTCTT GGTACNCTTG     420

GTTCGGCCCA GCTCCNCGTC CAAAAANTAT TCACCCNNCT CCNAATTGCT TGCNGGNCCC     480

CC                                                                   482

(2) INFORMATION FOR SEQ ID NO:190:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (xi) SEQUENCE DESCRIPTION: SEQ ID NO:190:

TTTTTTTTTT TTTTAAAACA GTTTTTCACA ACAAAATTTA TTAGAAGAAT AGTGGTTTTG      60

AAAACTCTCG CATCCAGTGA GAACTACCAT ACACCACATT ACAGCTNGGA ATGTNCTCCA     120

AATGTCTGGT CAAATGATAC AATGGAACCA TTCAATCTTA CACATGCACG AAAGAACAAG    180
```

| CGCTTTTGAC | ATACAATGCA | CAAAAAAAAA | AGGGGGGGGG | GACCACATGG | ATTAAAATTT | 240 |
| TAAGTACTCA | TCACATACAT | TAAGACACAG | TTCTAGTCCA | GTCNAAAATC | AGAACTGCNT | 300 |
| TGAAAAATTT | CATGTATGCA | ATCCAACCAA | AGAACTTNAT | TGGTGATCAT | GANTNCTCTA | 360 |
| CTACATCNAC | CTTGATCATT | GCCAGGAACN | AAAAGTTNAA | ANCACNCNGT | ACAAAAANAA | 420 |
| TCTGTAATTN | ANTTCAACCT | CCGTACNGAA | AAATNTTNNT | TATACACTCC | C | 471 |

(2) INFORMATION FOR SEQ ID NO:191:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO:191:

| GAGGGATTGA | AGGTCTGTTC | TASTGTCGGM | CTGTTCAGCC | ACCAACTCTA | ACAAGTTGCT | 60 |
| GTCTTCCACT | CACTGTCTGT | AAGCTTTTTA | ACCCAGACWG | TATCTTCATA | AATAGAACAA | 120 |
| ATTCTTCACC | AGTCACATCT | TCTAGGACCT | TTTTGGATTC | AGTTAGTATA | AGCTCTTCCA | 180 |
| CTTCCTTTGT | TAAGACTTCA | TCTGGTAAAG | TCTTAAGTTT | TGTAGAAAGG | AATTYAATTG | 240 |
| CTCGTTCTCT | AACAATGTCC | TCTCCTTGAA | GTATTTGGCT | GAACAACCCA | CCTAAAGTCC | 300 |
| CTTTGTGCAT | CCATTTTAAA | TATACTTAAT | AGGGCATTGK | TNCACTAGGT | TAAATTCTGC | 360 |
| AAGAGTCATC | TGTCTGCAAA | AGTTGCGTTA | GTATATCTGC | CA | | 402 |

(2) INFORMATION FOR SEQ ID NO:192:

(i) SEQUENCE CHARACTERISTICS:
        (A) LENGTH: 601 base pairs
        (B) TYPE: nucleic acid
        (C) STRANDEDNESS: single
        (D) TOPOLOGY: linear (xi) SEQUENCE DESCRIPTION: SEQ ID NO:192:

| GAGCTCGGAT | CCAATAATCT | TTGTCTGAGG | GCAGCACACA | TATNCAGTGC | CATGGNAACT | 60 |
| GGTCTACCCC | ACATGGGAGC | AGCATGCCGT | AGNTATATAA | GGTCATTCCC | TGAGTCAGAC | 120 |
| ATGCYTYTTT | GAYTACCGTG | TGCCAAGTGC | TGGTGATTCT | YAACACACYT | CCATCCCGYT | 180 |
| CTTTTGTGGA | AAAACTGGCA | CTTKTCTGGA | ACTAGCARGA | CATCACTTAC | AAATTCACCC | 240 |
| ACGAGACACT | TGAAAGGTGT | AACAAAGCGA | YTCTTGCATT | GCTTTTTGTC | CCTCCGGCAC | 300 |
| CAGTTGTCAA | TACTAACCCG | CTGGTTTGCC | TCCATCACAT | TTGTGATCTG | TAGCTCTGGA | 360 |
| TACATCTCCT | GACAGTACTG | AAGAACTTCT | TCTTTTGTTT | CAAAAGCARC | TCTTGGTGCC | 420 |
| TGTTGGATCA | GGTTCCCATT | TCCCAGTCYG | AATGTTCACA | TGGCATATTT | WACTTCCCAC | 480 |
| AAAACATTGC | GATTTGAGGC | TCAGCAACAG | CAAATCCTGT | TCCGGCATTG | GCTGCAAGAG | 540 |
| CCTCGATGTA | GCCGGCCAGC | GCCAAGGCAG | GCGCCGTGAG | CCCCACCAGC | AGCAGAAGCA | 600 |
| G | | | | | | 601 |

(2) INFORMATION FOR SEQ ID NO:193:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (xi) SEQUENCE DESCRIPTION: SEQ ID NO:193:

```
ATACAGCCCA NATCCCACCA CGAAGATGCG CTTGTTGACT GAGAACCTGA TGCGGTCACT          60

GGTCCCGCTG TAGCCCCAGC GACTCTCCAC CTGCTGGAAG CGGTTGATGC TGCACTCYTT         120

CCCAACGCAG GCAGMAGCGG GSCCGGTCAA TGAACTCCAY TCGTGGCTTG GGGTKGACGG         180

TKAAGTGCAG GAAGAGGCTG ACCACCTCGC GGTCCACCAG GATGCCCGAC TGTGCGGGAC         240

CTGCAGCGAA ACTCCTCGAT GGTCATGAGC GGGAAGCGAA TGAGGCCCAG GGCCTTGCCC         300

AGAACCTTCC GCCTGTTCTC TGGCGTCACC TGCAGCTGCT GCCGCTGACA CTCGGCCTCG         360

GACCAGCGGA CAAACGGCRT TGAACAGCCG CACCTCACGG ATGCCCAGTG TGTCGCGCTC         420

CAGGAMMGSC ACCAGCGTGT CCAGGTCAAT GTCGGTGAAG CCCTCCGCGG GTRATGGCGT         480

CTGCAGTGTT TTTGTCGATG TTCTCCAGGC ACAGGCTGGC CAGCTGCGGT TCATCGAAGA         540

GTCGCGCCTG CGTGAGCAGC ATGAAGGCGT TGTCGGCTCG CAGTTCTTCT TCAGGAACTC         600

CACGCAAT                                                                 608

(2) INFORMATION FOR SEQ ID NO:194:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (xi) SEQUENCE DESCRIPTION: SEQ ID NO:194:

GAACGGCTGG ACCTTGCCTC GCATTGTGCT TGCTGGCAGG GAATACCTTG GCAAGCAGYT          60

CCAGTCCGAG CAGCCCCAGA CCGCTGCCGC CCGAAGCTAA GCCTGCCTCT GGCCTTCCCC         120

TCCGCCTCAA TGCAGAACCA GTAGTGGGAG CACTGTGTTT AGAGTTAAGA GTGAACACTG         180

TTTGATTTTA CTTGGGAATT TCCTCTGTTA TATAGCTTTT CCCAATGCTA ATTTCCAAAC         240

AACAACAACA AAATAACATG TTTGCCTGTT AAGTTGTATA AAAGTAGGTG ATTCTGTATT         300

TAAAGAAAAT ATTACTGTTA CATATACTGC TTGCAATTTC TGTATTTATT GKTNCTSTGG         360

AAATAAATAT AGTTATTAAA GGTTGTCANT CC                                      392

(2) INFORMATION FOR SEQ ID NO:195:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (xi) SEQUENCE DESCRIPTION: SEQ ID NO:195:

CCSTTKGAGG GGTKAGGKYC CAGTTYCCGA GTGGAAGAAA CAGGCCAGGA GAAGTGCGTG          60

CCGAGCTGAG GCAGATGTTC CCACAGTGAC CCCCAGAGCC STGGGSTATA GTYTCTGACC         120

CCTCNCAAGG AAAGACCACS TTCTGGGGAC ATGGGCTGGA GGGCAGGACC TAGAGGCACC         180

AAGGGAAGGC CCCATTCCGG GGSTGTTCCC CGAGGAGGAA GGGAAGGGGC TCTGTGTGCC         240

CCCCASGAGG AAGAGGCCCT GAGTCCTGGG ATCAGACACC CCTTCACGTG TATCCCCACA         300

CAAATGCAAG CTCACCAAGG TCCCCTCTCA GTCCCCTTCC STACACCCTG AMCGGCCACT         360

GSCSCACACC CACCCAGAGC ACGCCACCCG CCATGGGGAR TGTGCTCAAG GARTCGCNGG         420

GCARCGTGGA CATCTNGTCC CAGAAGGGGG CAGAATCTCC AATAGANGGA CTGARCMSTT         480

GCTNANAAAA AAAAANAAAA AA                                                 502

(2) INFORMATION FOR SEQ ID NO:196:
```

-continued (i) SEQUENCE CHARACTERISTICS:
    (A) LENGTH: 665 base pairs
    (B) TYPE: nucleic acid
    (C) STRANDEDNESS: single
    (D) TOPOLOGY: linear (xi) SEQUENCE DESCRIPTION: SEQ ID NO:196:

| | | | | | |
|---|---|---|---|---|---|
| GGTTACTTGG | TTTCATTGCC | ACCACTTAGT | GGATGTCATT | TAGAACCATT | TTGTCTGCTC | 60 |
| CCTCTGGAAG | CCTTGCGCAG | AGCGGACTTT | GTAATTGTTG | GAGAATAACT | GCTGAATTTT | 120 |
| WAGCTGTTTK | GAGTTGATTS | GCACCACTGC | ACCCACAACT | TCAATATGAA | AACYAWTTGA | 180 |
| ACTWATTTAT | TATCTTGTGA | AAAGTATAAC | AATGAAAATT | TTGTTCATAC | TGTATTKATC | 240 |
| AAGTATGATG | AAAAGCAAWA | GATATATATT | CTTTTATTAT | GTTAAATTAT | GATTGCCATT | 300 |
| ATTAATCGGC | AAAATGTGGA | GTGTATGTTC | TTTTCACAGT | AATATATGCC | TTTTGTAACT | 360 |
| TCACTTGGTT | ATTTTATTGT | AAATGARTTA | CAAAATTCTT | AATTTAAGAR | AATGGTATGT | 420 |
| WATATTTATT | TCATTAATTT | CTTTCCTKGT | TTACGTWAAT | TTTGAAAAGA | WTGCATGATT | 480 |
| TCTTGACAGA | AATCGATCTT | GATGCTGTGG | AAGTAGTTTG | ACCCACATCC | CTATGAGTTT | 540 |
| TTCTTAGAAT | GTATAAAGGT | TGTAGCCCAT | CNAACTTCAA | AGAAAAAAAT | GACCACATAC | 600 |
| TTTGCAATCA | GGCTGAAATG | TGGCATGCTN | TTCTAATTCC | AACTTTATAA | ACTAGCAAAN | 660 |
| AAGTG | | | | | | 665 |

(2) INFORMATION FOR SEQ ID NO:197:

(i) SEQUENCE CHARACTERISTICS:
    (A) LENGTH: 492 base pairs
    (B) TYPE: nucleic acid
    (C) STRANDEDNESS: single
    (D) TOPOLOGY: linear (xi) SEQUENCE DESCRIPTION: SEQ ID NO:197:

| | | | | | |
|---|---|---|---|---|---|
| TTTTNTTTTT | TTTTTTTTGC | AGGAAGGATT | CCATTTATTG | TGGATGCATT | TTCACAATAT | 60 |
| ATGTTTATTG | GAGCGATCCA | TTATCAGTGA | AAAGTATCAA | GTGTTTATAA | NATTTTTAGG | 120 |
| AAGGCAGATT | CACAGAACAT | GCTNGTCNGC | TTGCAGTTTT | ACCTCGTANA | GATNACAGAG | 180 |
| AATTATAGTC | NAACCAGTAA | ACNAGGAATT | TACTTTTCAA | AAGATTAAAT | CCAAACTGAA | 240 |
| CAAAATTCTA | CCCTGAAACT | TACTCCATCC | AAATATTGGA | ATAANAGTCA | GCAGTGATAC | 300 |
| ATTCTCTTCT | GAACTTTAGA | TTTTCTAGAA | AAATATGTAA | TAGTGATCAG | GAAGAGCTCT | 360 |
| TGTTCAAAAG | TACAACNAAG | CAATGTTCCC | TTACCATAGG | CCTTAATTCA | AACTTTGATC | 420 |
| CATTTCACTC | CCATCACGGG | AGTCAATGCT | ACCTGGGACA | CTTGTATTTT | GTTCATNCTG | 480 |
| ANCNTGGCTT | AA | | | | | 492 |

(2) INFORMATION FOR SEQ ID NO:198:

(i) SEQUENCE CHARACTERISTICS:
    (A) LENGTH: 478 base pairs
    (B) TYPE: nucleic acid
    (C) STRANDEDNESS: single
    (D) TOPOLOGY: linear (xi) SEQUENCE DESCRIPTION: SEQ ID NO:198:

| | | | | | |
|---|---|---|---|---|---|
| TTTNTTTTGN | ATTTCANTCT | GTANNAANTA | TTTTCATTAT | GTTTATTANA | AAAATATNAA | 60 |
| TGTNTCCACN | ACAAATCATN | TTACNTNAGT | AAGAGGCCAN | CTACATTGTA | CAACATACAC | 120 |
| TGAGTATATT | TTGAAAAGGA | CAAGTTTAAA | GTANACNCAT | ATTGCCGANC | ATANCACATT | 180 |
| TATACATGGC | TTGATTGATA | TTTAGCACAG | CANAAACTGA | GTGAGTTACC | AGAAANAAAT | 240 |

```
NATATATGTC AATCNGATTT AAGATACAAA ACAGATCCTA TGGTACATAN CATCNTGTAG    300

GAGTTGTGGC TTTATGTTTA CTGAAAGTCA ATGCAGTTCC TGTACAAAGA GATGGCCGTA    360

AGCATTCTAG TACCTCTACT CCATGGTTAA GAATCGTACA CTTATGTTTA CATATGTNCA    420

GGGTAAGAAT TGTGTTAAGT NAANTTATGG AGAGGTCCAN GAGAAAAATT TGATNCAA     478
```

(2) INFORMATION FOR SEQ ID NO:199:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (xi) SEQUENCE DESCRIPTION: SEQ ID NO:199:

```
AGTGACTTGT CCTCCAACAA AACCCCTTGA TCAAGTTTGT GGCACTGACA ATCAGACCTA     60

TGCTAGTTCC TGTCATCTAT TCGCTACTAA ATGCAGACTG GAGGGACCA AAAAGGGGCA    120

TCAACTCCAG CTGGATTATT TTGGAGCCTG CAAATCTATT CCTACTTGTA CGGACTTTGA    180

AGTGATTCAG TTTCCTCTAC GGATGAGAGA CTGGCTCAAG AATATCCTCA TGCAGCTTTA    240

TGAAGCCNAC TCTGAACACG CTGGTTATCT NAGATGAGAA NCAGAGAAAT AAAGTCNAGA    300

AAATTTACCT GGANGAAAAG AGGCTTTNGG CTGGGGACCA TCCCATTGAA CCTTCTCTTA    360

ANGGACTTTA AGAANAAACT ACCACATGTN TGTNGTATCC TGGTGCCNGG CCGTTTANTG    420

AACNTNGACN NCACCCTTNT GGAATANANT CTTGACNGCN TCCTGAACTT GCTCCTCTGC    480

GA                                                                  482
```

(2) INFORMATION FOR SEQ ID NO:200:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (xi) SEQUENCE DESCRIPTION: SEQ ID NO:200:

```
CGGCCGCAAG TGCAACTCCA GCTGGGGCCG TGCGGACGAA GATTCTGCCA GCAGTTGGTC     60

CGACTGCGAC GACGGCGGCG GCGACAGTCG CAGGTGCAGC GCGGGCGCCT GGGGTCTTGC    120

AAGGCTGAGC TGACGCCGCA GAGGTCGTGT CACGTCCCAC GACCTTGACG CCGTCGGGGA    180

CAGCCGGAAC AGAGCCCGGT GAANGCGGGA GGCCTCGGGG AGCCCCTCGG GAAGGGCGGC    240

CCGAGAGATA CGCAGGTGCA GGTGGCCGCC                                    270
```

(2) INFORMATION FOR SEQ ID NO:201:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (xi) SEQUENCE DESCRIPTION: SEQ ID NO:201:

```
TTTTTTTTTT TTTTGGAATC TACTGCGAGC ACAGCAGGTC AGCAACAAGT TTATTTTGCA     60

GCTAGCAAGG TAACAGGGTA GGGCATGGTT ACATGTTCAG GTCAACTTCC TTTGTCGTGG    120

TTGATTGGTT TGTCTTTATG GGGGCGGGGT GGGGTAGGGG AAANCGAAGC ANAANTAACA    180

TGGAGTGGGT GCACCCTCCC TGTAGAACCT GGTTACNAAA GCTTGGGGCA GTTCACCTGG    240

TCTGTGACCG TCATTTTCTT GACATCAATG TTATTAGAAG TCAGGATATC TTTTAGAGAG    300
```

```
TCCACTGTNT CTGGAGGGAG ATTAGGGTTT CTTGCCAANA TCCAANCAAA ATCCACNTGA    360

AAAAGTTGGA TGATNCANGT ACNGAATACC GANGGCATAN TTCTCATANT CGGTGGCCA     419
```

(2) INFORMATION FOR SEQ ID NO:202:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (xi) SEQUENCE DESCRIPTION: SEQ ID NO:202:

```
TTTNTTTTTT TTTTTTTTTT TTTTTTTTTT TTTTTTTTTT TTTTTTTTTT TTTTTTTTTT    60

TGGCACTTAA TCCATTTTTA TTTCAAAATG TCTACAAANT TTNAATNCNC CATTATACNG    120

GTNATTTTNC AAAATCTAAA NNTTATTCAA ATNTNAGCCA AANTCCTTAC NCAAATNNAA    180

TACNCNCAAA AATCAAAAAT ATACNTNTCT TTCAGCAAAC TTNGTTACAT AAATTAAAAA    240

AATATATACG GCTGGTGTTT TCAAAGTACA ATTATCTTAA CACTGCAAAC ATNTTTNNAA    300

GGAACTAAAA TAAAAAAAAA CACTNCCGCA AAGGTTAAAG GGAACAACAA ATTCNTTTTA    360

CAACANCNNC NATTATAAAA ATCATATCTC AAATCTTAGG GGAATATATA CTTCACACNG    420

GGATCTTAAC TTTTACTNCA CTTTGTTTAT TTTTTTANAA CCATTGTNTT GGGCCCAACA    480

CAATGGNAAT NCCNCCNCNC TGGACTAGT                                      509
```

(2) INFORMATION FOR SEQ ID NO:203:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (xi) SEQUENCE DESCRIPTION: SEQ ID NO:203:

```
TTTTTTTTTT TTTTTTTTGA CCCCCCTCTT ATAAAAAACA AGTTACCATT TTATTTTACT    60

TACACATATT TATTTTATAA TTGGTATTAG ATATTCAAAA GGCAGCTTTT AAAATCAAAC    120

TAAATGGAAA CTGCCTTAGA TACATAATTC TTAGGAATTA GCTTAAAATC TGCCTAAAGT    180

GAAAATCTTC TCTAGCTCTT TTGACTGTAA ATTTTTGACT CTTGTAAAAC ATCCAAATTC    240

ATTTTTCTTG TCTTTAAAAT TATCTAATCT TTCCATTTTT TCCCTATTCC AAGTCAATTT    300

GCTTCTCTAG CCTCATTTCC TAGCTCTTAT CTACTATTAG TAAGTGGCTT TTTTCCTAAA    360

AGGGAAAACA GGAAGAGANA ATGGCACACA AAACAAACAT TTTATATTCA TATTTCTACC    420

TACGTTAATA AAATAGCATT TTGTGAAGCC AGCTCAAAAG AAGGCTTAGA TCCTTTTATG    480

TCCATTTTAG TCACTAAACG ATATCNAAAG TGCCAGAATG CAAAAGGTTT GTGAACATTT    540

ATTCAAAAGC TAATATAAGA TATTTCACAT ACTCATCTTT CTG                      583
```

(2) INFORMATION FOR SEQ ID NO:204:

(i) SEQUENCE CHARACTERISTICS:
        (A) LENGTH: 589 base pairs
        (B) TYPE: nucleic acid
        (C) STRANDEDNESS: single
        (D) TOPOLOGY: linear (xi) SEQUENCE DESCRIPTION: SEQ ID NO:204:

```
TTTTTTTTNT TTTTTTTTTT TTTTTTNCTC TTCTTTTTTT TTGANAATGA GGATCGAGTT    60

TTTCACTCTC TAGATAGGGC ATGAAGAAAA CTCATCTTTC CAGCTTTAAA ATAACAATCA    120
```

| | |
|---|---|
| AATCTCTTAT GCTATATCAT ATTTTAAGTT AAACTAATGA GTCACTGGCT TATCTTCTCC | 180 |
| TGAAGGAAAT CTGTTCATTC TTCTCATTCA TATAGTTATA TCAAGTACTA CCTTGCATAT | 240 |
| TGAGAGGTTT TTCTTCTCTA TTTACACATA TATTTCCATG TGAATTTGTA TCAAACCTTT | 300 |
| ATTTTCATGC AAACTAGAAA ATAATGTNTT CTTTTGCATA AGAGAAGAGA ACAATATNAG | 360 |
| CATTACAAAA CTGCTCAAAT TGTTTGTTAA GNTTATCCAT TATAATTAGT TNGGCAGGAG | 420 |
| CTAATACAAA TCACATTTAC NGACNAGCAA TAATAAAACT GAAGTACCAG TTAAATATCC | 480 |
| AAAATAATTA AAGGAACATT TTTAGCCTGG GTATAATTAG CTAATTCACT TTACAAGCAT | 540 |
| TTATTNAGAA TGAATTCACA TGTTATTATT CCNTAGCCCA ACACAATGG | 589 |

(2) INFORMATION FOR SEQ ID NO:205:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (xi) SEQUENCE DESCRIPTION: SEQ ID NO:205:

| | |
|---|---|
| TTTTTNTTTT TTTTTTCAGT AATAATCAGA ACAATATTTA TTTTTATATT TAAAATTCAT | 60 |
| AGAAAAGTGC CTTACATTTA ATAAAAGTTT GTTTCTCAAA GTGATCAGAG GAATTAGATA | 120 |
| TNGTCTTGAA CACCAATATT AATTTGAGGA AAATACACCA AAATACATTA AGTAAATTAT | 180 |
| TTAAGATCAT AGAGCTTGTA AGTGAAAAGA TAAAATTTGA CCTCAGAAAC TCTGAGCATT | 240 |
| AAAAATCCAC TATTAGCAAA TAAATTACTA TGGACTTCTT GCTTTAATTT TGTGATGAAT | 300 |
| ATGGGGTGTC ACTGGTAAAC CAACACATTC TGAAGGATAC ATTACTTAGT GATAGATTCT | 360 |
| TATGTACTTT GCTANATNAC GTGGATATGA GTTGACAAGT TTCTCTTTCT TCAATCTTTT | 420 |
| AAGGGGCNGA NGAAATGAGG AAGAAAAGAA AAGGATTACG CATACTGTTC TTTCTATNGG | 480 |
| AAGGATTAGA TATGTTTCCT TTGCCAATAT TAAAAAAATA ATAATGTTTA CTACTAGTGA | 540 |
| AACCC | 545 |

(2) INFORMATION FOR SEQ ID NO:206:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:206:

| | |
|---|---|
| TTTTTTTTTT TTTTTTAGTC AAGTTTCTNA TTTTTATTAT AATTAAAGTC TTGGTCATTT | 60 |
| CATTTATTAG CTCTGCAACT TACATATTTA AATTAAAGAA ACGTTNTTAG ACAACTGTNA | 120 |
| CAATTTATAA ATGTAAGGTG CCATTATTGA GTANATATAT TCCTCCAAGA GTGGATGTGT | 180 |
| CCCTTCTCCC ACCAACTAAT GAANCAGCAA CATTAGTTTA ATTTTATTAG TAGATNATAC | 240 |
| ACTGCTGCAA ACGCTAATTC TCTTCTCCAT CCCCATGTNG ATATTGTGTA TATGTGTGAG | 300 |
| TTGGTNAGAA TGCATCANCA ATCTNACAAT CAACAGCAAG ATGAAGCTAG GCNTGGGCTT | 360 |
| TCGGTGAAAA TAGACTGTGT CTGTCTGAAT CAAATGATCT GACCTATCCT CGGTGGCAAG | 420 |
| AACTCTTCGA ACCGCTTCCT CAAAGGCNGC TGCCACATTT GTGGCNTCTN TTGCACTTGT | 480 |
| TTCAAAA | 487 |

(2) INFORMATION FOR SEQ ID NO:207:

(i) SEQUENCE CHARACTERISTICS:
      (A) LENGTH: 332 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:207:

```
TGAATTGGCT AAAAGACTGC ATTTTTANAA CTAGCAACTC TTATTTCTTT CCTTTAAAAA        60

TACATAGCAT TAAATCCCAA ATCCTATTTA AAGACCTGAC AGCTTGAGAA GGTCACTACT       120

GCATTTATAG GACCTTCTGG TGGTTCTGCT GTTACNTTTG AANTCTGACA ATCCTTGANA       180

ATCTTTGCAT GCAGAGGAGG TAAAAGGTAT TGGATTTTCA CAGAGGAANA ACACAGCGCA       240

GAAATGAAGG GGCCAGGCTT ACTGAGCTTG TCCACTGGAG GGCTCATGGG TGGGACATGG       300

AAAAGAAGGC AGCCTAGGCC CTGGGGAGCC CA                                     332
```

(2) INFORMATION FOR SEQ ID NO:208:

(i) SEQUENCE CHARACTERISTICS:
      (A) LENGTH: 524 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:208:

```
AGGGCGTGGT GCGGAGGGCG TTACTGTTTT GTCTCAGTAA CAATAAATAC AAAAAGACTG        60

GTTGTGTTCC GGCCCCATCC AACCACGAAG TTGATTTCTC TTGTGTGCAG AGTGACTGAT       120

TTTAAAGGAC ATGGAGCTTG TCACAATGTC ACAATGTCAC AGTGTGAAGG GCACACTCAC       180

TCCCGCGTGA TTCACATTTA GCAACCAACA ATAGCTCATG AGTCCATACT TGTAAATACT       240

TTTGGCAGAA TACTTNTTGA AACTTGCAGA TGATAACTAA GATCCAAGAT ATTTCCCAAA       300

GTAAATAGAA GTGGGTCATA ATATTAATTA CCTGTTCACA TCAGCTTCCA TTTACAAGTC       360

ATGAGCCCAG ACACTGACAT CAAACTAAGC CCACTTAGAC TCCTCACCAC CAGTCTGTCC       420

TGTCATCAGA CAGGAGGCTG TCACCTTGAC CAAATTCTCA CCAGTCAATC ATCTATCCAA       480

AAACCATTAC CTGATCCACT TCCGGTAATG CACCACCTTG GTGA                        524
```

(2) INFORMATION FOR SEQ ID NO:209:

(i) SEQUENCE CHARACTERISTICS:
      (A) LENGTH: 159 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:209:

```
GGGTGAGGAA ATCCAGAGTT GCCATGGAGA AAATTCCAGT GTCAGCATTC TTGCTCCTTG        60

TGGCCCTCTC CTACACTCTG GCCAGAGATA CCACAGTCAA ACCTGGAGCC AAAAAGGACA       120

CAAAGGACTC TCGACCCAAA CTGCCCCAGA CCCTCTCCA                              159
```

(2) INFORMATION FOR SEQ ID NO:210:

(i) SEQUENCE CHARACTERISTICS:
      (A) LENGTH: 256 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:210:

ACTCCCTGGC AGACAAAGGC AGAGGAGAGA GCTCTGTTAG TTCTGTGTTG TTGAACTGCC     60

ACTGAATTTC TTTCCACTTG GACTATTACA TGCCANTTGA GGGACTAATG GAAAAACGTA    120

TGGGGAGATT TTANCCAATT TANGTNTGTA AATGGGGAGA CTGGGGCAGG CGGGAGAGAT    180

TTGCAGGGTG NAAATGGGAN GGCTGGTTTG TTANATGAAC AGGGACATAG GAGGTAGGCA    240

CCAGGATGCT AAATCA                                                    256

(2) INFORMATION FOR SEQ ID NO:211:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:211:

ACATTGTTTT TTTGAGATAA AGCATTGAGA GAGCTCTCCT TAACGTGACA CAATGGAAGG     60

ACTGGAACAC ATACCCACAT CTTTGTTCTG AGGGATAATT TTCTGATAAA GTCTTGCTGT    120

ATATTCAAGC ACATATGTTA TATATTATTC AGTTCCATGT TTATAGCCTA GTTAAGGAGA    180

GGGGAGATAC ATTCNGAAAG AGGACTGAAA GAAATACTCA AGTNGGAAAA CAGAAAAAGA    240

AAAAAAGGAG CAAATGAGAA GCCT                                           264

(2) INFORMATION FOR SEQ ID NO:212:

(i) SEQUENCE CHARACTERISTICS:
        (A) LENGTH: 328 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:212:

ACCCAAAAAT CCAATGCTGA ATATTTGGCT TCATTATTCC CANATTCTTT GATTGTCAAA     60

GGATTTAATG TTGTCTCAGC TTGGGCACTT CAGTTAGGAC CTAAGGATGC CAGCCGGCAG    120

GTTTATATAT GCAGCAACAA TATTCAAGCG CGACAACAGG TTATTGAACT TGCCCGCCAG    180

TTNAATTTCA TTCCCATTGA CTTGGGATCC TTATCATCAG CCAGAGAGAT TGAAAATTTA    240

CCCCTACNAC TCTTTACTCT CTGGANAGGG CCAGTGGTGG TAGCTATAAG CTTGGCCACA    300

TTTTTTTTTC CTTTATTCCT TTGTCAGA                                       328

(2) INFORMATION FOR SEQ ID NO:213:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:213:

| | |
|---|---|
| ACTTATGAGC AGAGCGACAT ATCCNAGTGT AGACTGAATA AAACTGAATT CTCTCCAGTT | 60 |
| TAAAGCATTG CTCACTGAAG GGATAGAAGT GACTGCCAGG AGGGAAAGTA AGCCAAGGCT | 120 |
| CATTATGCCA AAGGANATAT ACATTTCAAT TCTCCAAACT TCTTCCTCAT TCCAAGAGTT | 180 |
| TTCAATATTT GCATGAACCT GCTGATAANC CATGTTAANA AACAAATATC TCTCTNACCT | 240 |
| TCTCATCGGT | 250 |

(2) INFORMATION FOR SEQ ID NO:214:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:214:

| | |
|---|---|
| ACCCAGAATC CAATGCTGAA TATTTGGCTT CATTATTCCC AGATTCTTTG ATTGTCAAAG | 60 |
| GATTTAATGT TGTCTCAGCT TGGGCACTTC AGTTAGGACC TAAGGATGCC AGCCGGCAGG | 120 |
| TTTATATATG CAGCAACAAT ATTCAAGCGC GACAACAGGT TATTGAACTT GCCCGCCAGT | 180 |
| TGAATTTCAT TCCCATTGAC TTGGGATCCT TATCATCAGC CANAGAGATT GAAAATTTAC | 240 |
| CCCTACGACT CTTTACTCTC TGGAGAGGGC CAGTGGTGGT AGCTATAAGC TTGGCCACAT | 300 |
| TTTTTTTTCC TTTATTCCTT TGTCAGAGAT GCGATTCATC CATATGCTAN AAACCAACAG | 360 |
| AGTGACTTTT ACAAAATTCC TATAGANATT GTGAATAAAA CCTTACCTAT AGTTGCCATT | 420 |
| ACTTTGCTCT CCCTAATATA CCTC | 444 |

(2) INFORMATION FOR SEQ ID NO:215:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:215:

| | |
|---|---|
| ACTTATGAGC AGAGCGACAT ATCCAAGTGT ANACTGAATA AAACTGAATT CTCTCCAGTT | 60 |
| TAAAGCATTG CTCACTGAAG GGATAGAAGT GACTGCCAGG AGGGAAAGTA AGCCAAGGCT | 120 |
| CATTATGCCA AAGGANATAT ACATTTCAAT TCTCCAAACT TCTTCCTCAT TCCAAGAGTT | 180 |
| TTCAATATTT GCATGAACCT GCTGATAAGC CATGTTGAGA AACAAATATC TCTCTGACCT | 240 |
| TCTCATCGGT AAGCAGAGGC TGTAGGCAAC ATGGACCATA GCGAANAAAA AACTTAGTAA | 300 |
| TCCAAGCTGT TTTCTACACT GTAACCAGGT TTCCAACCAA GGTGGAAATC TCCTATACTT | 360 |
| GGTGCC | 366 |

(2) INFORMATION FOR SEQ ID NO:216:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:216:

| | |
|---|---|
| CTGTATAAAC AGAACTCCAC TGCANGAGGG AGGGCCGGGC CAGGAGAATC TCCGCTTGTC | 60 |

```
CAAGACAGGG GCCTAAGGAG GGTCTCCACA CTGCTNNTAA GGGCTNTTNC ATTTTTTTAT      120

TAATAAAAAG TNNAAAAGGC CTCTTCTCAA CTTTTTTCCC TTNGGCTGGA AAATTTAAAA      180

ATCAAAAATT TCCTNAAGTT NTCAAGCTAT CATATATACT NTATCCTGAA AAAGCAACAT      240

AATTCTTCCT TCCCTCCTTT                                                  260

(2) INFORMATION FOR SEQ ID NO:217:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:217:

ACCTACGTGG GTAAGTTTAN AAATGTTATA ATTTCAGGAA NAGGAACGCA TATAATTGTA       60

TCTTGCCTAT AATTTTCTAT TTTAATAAGG AAATAGCAAA TTGGGGTGGG GGGAATGTAG      120

GGCATTCTAC AGTTTGAGCA AAATGCAATT AAATGTGGAA GGACAGCACT GAAAAATTTT      180

ATGAATAATC TGTATGATTA TATGTCTCTA GAGTAGATTT ATAATTAGCC ACTTACCCTA      240

ATATCCTTCA TGCTTGTAAA GT                                              262

(2) INFORMATION FOR SEQ ID NO:218:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:218:

ACCAAGGTGG TGCATTACCG GAANTGGATC AANGACACCA TCGTGGCCAA CCCCTGAGCA       60

CCCCTATCAA CTCCCTTTTG TAGTAAACTT GGAACCTTGG AAATGACCAG GCCAAGACTC      120

AGGCCTCCCC AGTTCTACTG ACCTTTGTCC TTANGTNTNA NGTCCAGGGT TGCTAGGAAA      180

ANAAATCAGC AGACACAGGT GTAAA                                           205

(2) INFORMATION FOR SEQ ID NO:219:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:219:

TACTGTTTTG TCTCAGTAAC AATAAATACA AAAAGACTGG TTGTGTTCCG GCCCCATCCA       60

ACCACGAAGT TGATTTCTCT TGTGTGCAGA GTGACTGATT TTAAAGGACA TGGA            114

(2) INFORMATION FOR SEQ ID NO:220:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:220:

| | |
|---|---|
| ACTAGCCAGC ACAAAAGGCA GGGTAGCCTG AATTGCTTTC TGCTCTTTAC ATTTCTTTTA | 60 |
| AAATAAGCAT TTAGTGCTCA GTCCCTACTG AGT | 93 |

(2) INFORMATION FOR SEQ ID NO:221:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:221:

| | |
|---|---|
| ACTANGTGCA GGTGCGCACA AATATTTGTC GATATTCCCT TCATCTTGGA TTCCATGAGG | 60 |
| TCTTTTGCCC AGCCTGTGGC TCTACTGTAG TAAGTTTCTG CTGATGAGGA GCCAGNATGC | 120 |
| CCCCCACTAC CTTCCCTGAC GCTCCCCANA AATCACCCAA CCTCTGT | 167 |

(2) INFORMATION FOR SEQ ID NO:222:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:222:

| | |
|---|---|
| AGGGCGTGGT GCGGAGGGCG GTACTGACCT CATTAGTAGG AGGATGCATT CTGGCACCCC | 60 |
| GTTCTTCACC TGTCCCCCAA TCCTTAAAAG GCCATACTGC ATAAAGTCAA CAACAGATAA | 120 |
| ATGTTTGCTG AATTAAAGGA TGGATGAAAA AAATTAATAA TGAATTTTTG CATAATCCAA | 180 |
| TTTTCTCTTT TATATTTCTA GAAGAAGTTT CTTTGAGCCT ATTAGATCCC GGGAATCTTT | 240 |
| TAGGTGAGCA TGATTAGAGA GCTTGTAGGT TGCTTTTACA TATATCTGGC ATATTTGAGT | 300 |
| CTCGTATCAA AACAATAGAT TGGTAAAGGT GGTATTATTG TATTGATAAG T | 351 |

(2) INFORMATION FOR SEQ ID NO:223:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO:223:

| | |
|---|---|
| AAAACAAACA AACAAAAAAA ACAATTCTTC ATTCAGAAAA ATTATCTTAG GGACTGATAT | 60 |
| TGGTAATTAT GGTCAATTTA ATWRTRTTKT GGGGCATTTC CTTACATTGT CTTGACAAGA | 120 |
| TTAAAATGTC TGTGCCAAAA TTTTGTATTT TATTTGGAGA CTTCTTATCA AAAGTAATGC | 180 |
| TGCCAAAGGA AGTCTAAGGA ATTAGTAGTG TTCCCMTCAC TTGTTTGGAG TGTGCTATTC | 240 |
| TAAAAGATTT TGATTTCCTG GAATGACAAT TATATTTTAA CTTTGGTGGG GGAAANAGTT | 300 |
| ATAGGACCAC AGTCTTCACT TCTGATACTT GTAAATTAAT CTTTTATTGC ACTTGTTTTG | 360 |
| ACCATTAAGC TATATGTTTA AAA | 383 |

(2) INFORMATION FOR SEQ ID NO:224:

-continued

```
    (i) SEQUENCE CHARACTERISTICS:
        (A) LENGTH: 320 base pairs
        (B) TYPE: nucleic acid
        (C) STRANDEDNESS: single
        (D) TOPOLOGY: linear (xi) SEQUENCE DESCRIPTION: SEQ ID NO:224:

CCCCTGAAGG CTTCTTGTTA GAAAATAGTA CAGTTACAAC CAATAGGAAC AACAAAAAGA      60

AAAAGTTTGT GACATTGTAG TAGGGAGTGT GTACCCCTTA CTCCCCATCA AAAAAAAAAT     120

GGATACATGG TTAAAGGATA RAAGGGCAAT ATTTTATCAT ATGTTCTAAA AGAGAAGGAA     180

GAGAAAATAC TACTTTCTCR AAATGGAAGC CCTTAAAGGT GCTTTGATAC TGAAGGACAC     240

AAATGTGGCC GTCCATCCTC CTTTARAGTT GCATGACTTG GACACGGTAA CTGTTGCAGT     300

TTTARACTCM GCATTGTGAC                                                 320
```